(12) United States Patent
Pease et al.

(10) Patent No.: US 10,369,513 B2
(45) Date of Patent: Aug. 6, 2019

(54) METHODS FOR METHANE PURIFICATION

(71) Applicant: ALCHEM ENVIRONMENTAL IP LLC, Salt Lake City, UT (US)

(72) Inventors: John R. Pease, Salt Lake City, UT (US); John F. Blatnick, Salt Lake City, UT (US)

( * ) Notice: Subject to any disclaimer, the term of this patent is extended or adjusted under 35 U.S.C. 154(b) by 136 days.

(21) Appl. No.: 15/696,946

(22) Filed: Sep. 6, 2017

(65) Prior Publication Data

US 2018/0078895 A1 Mar. 22, 2018

Related U.S. Application Data

(60) Division of application No. 14/867,524, filed on Sep. 28, 2015, now Pat. No. 9,757,683, which is a
(Continued)

(51) Int. Cl.
*B01D 53/18* (2006.01)
*B01F 5/00* (2006.01)
(Continued)

(52) U.S. Cl.
CPC .......... *B01D 53/18* (2013.01); *B01D 53/1462* (2013.01); *B01F 3/02* (2013.01);
(Continued)

(58) Field of Classification Search
CPC .... B01D 53/18; B01D 53/1462; B01F 3/0446
See application file for complete search history.

(56) References Cited

U.S. PATENT DOCUMENTS

| 809,383 A | 1/1906 | Lowe |
| 1,799,684 A | 4/1931 | Gilbert et al. |
| (Continued) | | |

FOREIGN PATENT DOCUMENTS

| GB | 794060 | 4/1958 |
| JP | 2004357561 | 12/2004 |
| WO | WO 2014/027993 | 2/2014 |

OTHER PUBLICATIONS

International Search Report and Written Opinion for PCT/US2012/050623 dated Oct. 26, 2012, 22 pages.
(Continued)

*Primary Examiner* — Robert A Hopkins
(74) *Attorney, Agent, or Firm* — Workman Nydegger

(57) ABSTRACT

Ancillary embodiments and modifications to a homogenizer unit ("PPH"), and methods of use directed to purification of biogas or other raw methane streams. The apparatus includes a homogenizer body, one or more stream inlets (for the raw methane), one or more chilled water inlets, a mixing zone where the water stream is commingled with the raw methane stream, and a venturi immediately downstream from the mixing zone such that the commingled streams are pulled into the venturi resulting in homogenization. The PPH components are insulated to maintain the chilled water of the various streams at a cooled, below ambient temperature, increasing dissolution of the contaminant gases into the chilled water, and producing a purified methane stream including little or no $H_2S$ and $CO_2$.

18 Claims, 15 Drawing Sheets

Related U.S. Application Data continuation-in-part of application No. 13/584,580, filed on Aug. 13, 2012, now Pat. No. 9,144,205, which is a continuation-in-part of application No. 12/573,327, filed on Oct. 5, 2009, now Pat. No. 8,241,410.

(60) Provisional application No. 61/106,256, filed on Oct. 17, 2008.

(51) Int. Cl.

| | | |
|---|---|---|
| B01F 3/04 | (2006.01) | |
| C10L 3/10 | (2006.01) | |
| C07C 7/11 | (2006.01) | |
| C01B 17/02 | (2006.01) | |
| B01D 53/14 | (2006.01) | |
| B01F 5/04 | (2006.01) | |
| C01B 32/50 | (2017.01) | |
| B01F 5/06 | (2006.01) | |
| B01F 3/02 | (2006.01) | |
| A01G 31/00 | (2018.01) | |

(52) U.S. Cl.
CPC ...... *B01F 3/04063* (2013.01); *B01F 3/04503* (2013.01); *B01F 5/043* (2013.01); *B01F 5/0415* (2013.01); *B01F 5/0604* (2013.01); *B01F 5/0606* (2013.01); *B01F 5/0647* (2013.01); *B01F 5/0655* (2013.01); *B01F 5/0695* (2013.01); *C01B 17/021* (2013.01); *C01B 32/50* (2017.08); *C07C 7/11* (2013.01); *C10L 3/103* (2013.01); *C10L 3/104* (2013.01); *A01G 31/00* (2013.01); *B01F 2005/0436* (2013.01); *C10L 2290/541* (2013.01); *Y02C 10/06* (2013.01); *Y02P 20/582* (2015.11)

(56) References Cited

U.S. PATENT DOCUMENTS

| | | | |
|---|---|---|---|
| 1,874,990 | A | 8/1932 | Hawley |
| 2,127,571 | A | 8/1938 | Pardee, Jr. |
| 2,489,893 | A | 11/1949 | Johnson |
| 2,658,735 | A | 11/1953 | Ybarrondo |
| 2,935,375 | A | 5/1960 | Boucher |
| 3,367,402 | A | 2/1968 | Cross, Jr. et al. |
| 3,369,344 | A | 2/1968 | Jackson et al. |
| 3,562,349 | A | 2/1971 | Pawloski et al. |
| 3,667,193 | A | 6/1972 | McKenzie |
| 3,736,797 | A | 6/1973 | Brown |
| 3,881,898 | A | 5/1975 | Darby et al. |
| 3,884,653 | A | 5/1975 | Capulli et al. |
| 4,023,938 | A | 5/1977 | Guth et al. |
| 4,124,660 | A | 11/1978 | Sterlini |
| 4,136,976 | A | 1/1979 | Leffelman |
| 4,204,775 | A | 5/1980 | Speer |
| 5,938,328 | A | 8/1999 | Pinto et al. |
| 6,001,155 | A | 12/1999 | Pease |
| 6,132,629 | A | 10/2000 | Boley |
| 6,209,856 | B1 | 4/2001 | Kojima |
| 6,391,100 | B1 | 5/2002 | Hogan |
| 6,395,175 | B1 | 5/2002 | Gao et al. |
| 6,485,548 | B1 | 11/2002 | Hogan |
| 6,500,804 | B2 | 12/2002 | Demuth et al. |
| 6,890,905 | B2 | 5/2005 | Demuth et al. |
| 7,132,104 | B1 | 11/2006 | von Horsten et al. |
| 7,435,420 | B2 | 10/2008 | von Hoersten et al. |
| 8,241,410 | B1 | 8/2012 | Pease et al. |
| 9,144,205 | B2 | 9/2015 | Pease et al. |
| 9,757,683 | B1 | 9/2017 | Pease et al. |
| 10,173,165 | B2 * | 1/2019 | Heirman ............... B01D 53/14 |
| 2004/0113288 | A1 | 6/2004 | Korzeniowski |
| 2010/0242346 | A1 | 9/2010 | Bunning et al. |
| 2011/0023359 | A1 | 2/2011 | Raring |
| 2011/0114548 | A1 | 5/2011 | Gillette |

OTHER PUBLICATIONS

U.S. Appl. No. 12/573,327, filed Sep. 23, 2011, Office Action.
U.S. Appl. No. 12/573,327, filed Feb. 16, 2012, Notice of Allowance.
U.S. Appl. No. 13/584,580, filed May 28, 2015, Notice of Allowance.
U.S. Appl. No. 14/867,572, filed Apr. 28, 2017, Notice of Allowance.
U.S. Appl. No. 14/867,572, filed Apr. 12, 2017, Notice of Allowance.

* cited by examiner

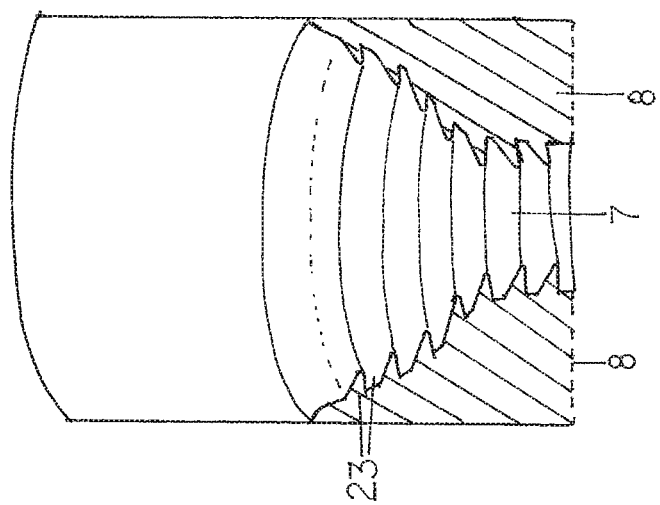
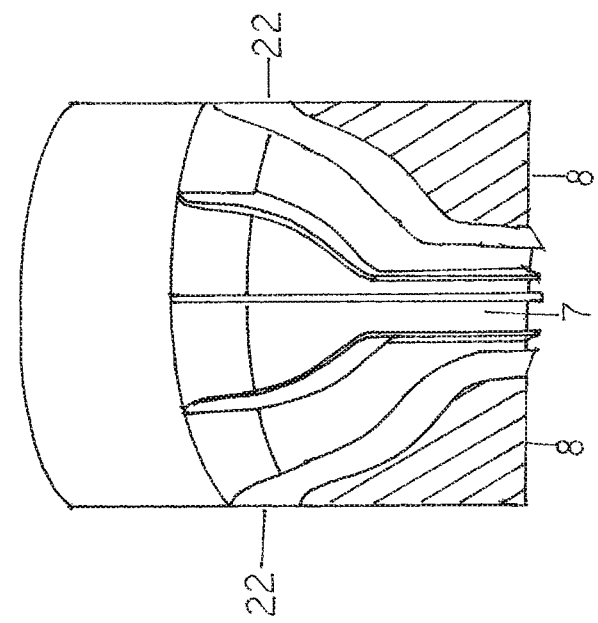
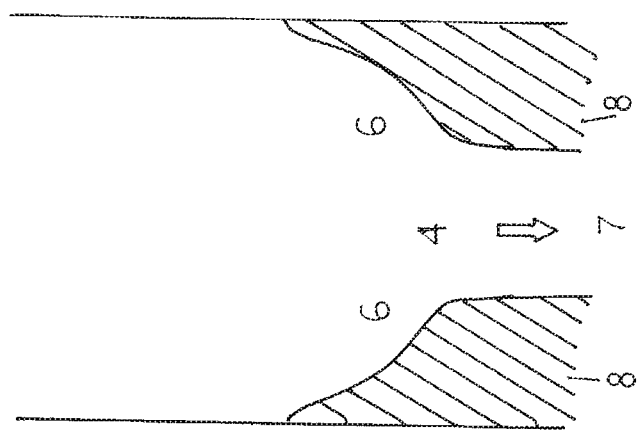

METHODS FOR METHANE PURIFICATION

CROSS-REFERENCE TO RELATED APPLICATIONS

This application is a divisional of U.S. patent application Ser. No. 14/867,524, filed on Sep. 28, 2015, entitled "Polyphasic Pressurized Homogenizer (PPH) and Methods for Methane Purification," which issued as U.S. Pat. No. 9,757,683, on Sep. 12, 2017, which is a continuation in part of U.S. patent application Ser. No. 13/584,580, filed on Aug. 13, 2012, entitled "Hydroponics Applications and Ancillary Modifications to a Polyphasic Pressurized Homogenizer," which issued as U.S. Pat. No. 9,144,205, on Sep. 29, 2015, which is a continuation in part of U.S. patent application Ser. No. 12/573,327, filed on Oct. 5, 2009, which issued as U.S. Pat. No. 8,241,410, on Aug. 14, 2012, which claims the benefit of U.S. Provisional Patent Application Ser. No. 61/106,256, filed on Oct. 17, 2008. The disclosure of each of the above patents and applications is herein incorporated by reference in its entirety.

1. FIELD OF THE INVENTION

The present ancillary modifications and embodiments significantly enhance the effectiveness of the extant invention, U.S. Pat. No. 6,001,155 (incorporated herein by reference), so as to enable the device to include chemical and physico-chemical reactions beyond that of the original intentions. Included within these reactions, but not limited to them, are the substitution of anions of the alkali and alkali-earth metals, ammonia, and other metallic and non-metallic elements and compounds.

The invention and the ancillary embodiments and modifications also have the ability to isolate, recombine, and cause reactions to occur between or among a wide variety of air-borne or liquid-borne gases, liquids, and particulates, either singly or in some combination. These reactions will immediately or eventually yield either commercially viable and/or environmentally neutral products and compounds.

The invention and ancillary embodiments also control heat by absorbing thermal energy into the aqueous or liquid phase of the various solvents used to further other reactions. The term "solvent" is used broadly and does not require that the solvent actually solubilize the material. For example, the "solvent" may simply be a carrier in which the material to be removed is not soluble, but is simply carried in some fashion by the "solvent" so as to facilitate its removal. This thermal energy may be from an outside source such as an exhaust stream, ambient air, or reaction heat (endothermic and exothermic heat production and absorption).

The ancillary device or devices serve to pre-mix a polluted stream or stream with a suitable gas or gases, solvent or solvents so as to have a uniform mixture thereby assuring that treatment of the now-mixed reactants have more uniform chemical behavior and characteristics than one encounters in a less homogeneous stream or streams.

2. RELATED APPLICATIONS

Air cleansing by removing gaseous, liquid, or particulate pollutants, either singly or in some combination from an air or exhaust stream.

Affecting and accelerating reactions between ionic and/or non-ionic compounds and/or elements within the confines of the homogenizer unit and/or within the ancillary devices attached to the homogenizer unit.

Ameliorating harmful impingements such as excess moisture removal, heat entrainment, or pollutant removal and mineralization from an exhaust stream.

Serving as a mixing device for air-borne Volatile Organic Compounds (VOCs) within an aqueous medium, thereby rendering the mixture amenable to VOC recovery, oxidation, or biodegradation.

Preparing compounds of benefit to the growth and metabolism of algae and other biota, such as plants grown under hydroponic conditions.

Enhancing the growth and metabolism of algae and other biota by circulating the culture or growth medium and/or relieving this medium of oxygen (which is toxic to most of the algae and higher plant species) while entraining carbon dioxide and ammonia as well as selected metabolites thereby allowing for the dissolution of these metabolites into the growth medium.

Serving as a mixing-agitating device to leach, bleach, wet, or otherwise modify a variety of mineral and non-mineral products for industrial processes including mineral recovery.

1. Removing radon gas from buildings.
2. Removing carbon monoxide gas from buildings.
3. Heat absorption from external as well as internal sources.

Note: A much more extensive list of homogenizer applications is attached.

3. BACKGROUND

At the time of the inception of the homogenizer unit, no other system(s), other than mechanical mixing, sparging, filtration, electrostatic precipitation, or pressurizing vessels were available to mix disparate pollutants in liquid, air, or gas streams. Also, no methods were available to mix air-particulate or air-gas-particulate streams that were of a polluting nature that caused such streams to be entrained in an aqueous medium or matrix under pressure that were intended for biodegradation. Although one could consider atmospheric discharge as a means of treating these streams, in reality, the transfer was simply a matter of diluting these streams with air. The problems of dealing with these same streams were avoided by transferring the pollutants to another medium with no treatment (venting pollutants to the atmosphere, etc.).

Operation of the invention indicated that certain types or categories of air-borne pollutants or reactants were not being adequate prepared for a complete chemical or physico-chemical reaction or reactions with a variety of other reactants within the homogenizer unit and required additional mixing and/or recycling through the homogenizer unit. The ancillary embodiments referred to in the descriptions ensure relatively much more rapid and thorough mixing of pollutants with suitable reactants and more uniform reactions occurring within the homogenizer unit.

Problems relating to tank design (as being important to reactions) were also much reduced since the blending or mixing within the homogenizer unit or units occurs largely within these units and is no longer dependent upon the tank or reservoir design (in whole or in part) to complete certain reactions. The tanks were relegated to serve as reservoirs for the solvents and mixed solutions. Agitators and special tank designs were therefore not required since one only has to direct the reactant solution or mixture to the pumping device so as to allow the mixture to be re-circulated, if need be. The homogenizer unit proved to be so effective at mixing that a reactant in solution could be pumped from one vessel, thence through the homogenizer unit and then to an equalizer or holding tank where the liquid was stored. Little or no recirculation was required if saturation limits were achieved in a single cycle.

Also, pollutants that required wetting, especially those there were recalcitrant to wetting (hydrophobic) became fully 'wetted' by being placed in intimate contact with a surfactant and thence being passed through the venturi or venturis within a homogenizer unit. The same basic principle applied to oleophobic (oil-resisting) matter that required 'wetting' so as to become soluble or suspended in an aqueous matrix. Once wetted, both the hydrophobic and oleophobic matter could be subjected to reactants or could be biodegraded, as intended or desired.

Certain pollutants didn't require degradation in any form, rather, they could simply be retained until a volume of a mixed matrix of solvent and pollutants was collected. Disposition by flushing to a common sewer was then suitable and possible.

Hazardous gas or gases, liquid droplets, and particulates were also readily entrained and recovered for further treatment or neutralized to reduce or eliminate their innate hazardous properties.

Most notably, the homogenizer unit or units allow(s) for a variety of chemical reactions to occur between ionic compounds. Many such reactions, especially substitutions of one anion for another, are noted on the SOLUBILITY CHART (CHART 1). In some instances, oxidation reactions are possible without dangerous effects occurring because the oxidations occur in an aqueous matrix. Other reactions, such as combining acids or bases with an aqueous matrix are done safely due to their being contained with the homogenizer unit while being buffered by water that both contains any out-gassing or heat generation. The heat common to these reactions was dispersed throughout the aqueous matrix (diluted), thus no overheating occurred. In practice, introducing flammable or explosive reactants can be completed safely due to the fact that such reactions occur while being diluted and cooled with surrounding liquid and the vessel walls as well as the homogenizer unit or units.

Many other practical chemical reactions are presented on CHART 1. Products that may produce an explosive situation such as wood and metal dust or other dusts as are found in grain silos and similar environs as well as lint from paper and fabric production, sugar dust, and solvent vapors, smoke, grease and oil aerosols are transferred from the atmosphere into an aqueous matrix and rendered harmless.

4. OTHER SOLUTIONS, IF ANY

One solution that has been used with limited success involves subjecting a receiving vessel, its contents, and the exiting matter to pressure (3-5 bars) with the intent of utilizing Boyle's Law regarding the inverse solubility of a gas or gases under pressure in liquids.

A common solution related to increasing oxygen dissolution in water while purging ammonia and carbon dioxide is 'air-sparging'. This practice requires a gas stream or streams to be forced downward through a conduit and are thence released at some depth into a liquid. The released air forms bubbles that enlarge as they rise through the water column. The intent is to have some portion of a selected gas dissolve at some rate in the liquid matrix.

Mixing by various means such as paddles, recycling via pumping, and shaking may require specially designed mixing vessels to prevent isolation and/or stagnation of the components being mixed within areas of the vessel that agitation does not affect to any significant degree.

Scrubbing or passing of air and pollutants through streams of water or mats that are wetted with water and/or some reactant is still used in air conditioning and scrubbers.

Electrostatic precipitation deals with a limited range of air-borne particulates, specifically those that would be affected by rendering an electrical charge to the particle mass or surface so as to cause the particle to collect upon some type of surface or medium having an opposite electrical charge.

Catalysts are elements, agents, or compounds that accelerate or enhance chemical or physical reactions without being consumed in the process.

5. SHORTCOMINGS OF OTHER SOLUTIONS

Pressurizing a vessel with the intent or 'forcing' a gas to dissolve in a liquid does work under very specific conditions, but the pressure must be continuously maintained and controlled in order to be safe for the end-users and the components must be able to withstand the pressure and potential corrosive reactions such pressure can enable.

Air-sparging is adequate to serve as a mixing device, but is very limited as to enhancing chemical substitutions or reactions. This is due to the fact that bubbles of gas have a decrease in their relative surface area to volume ratios as they rise to the surface and expand as they do so. The reverse phenomenon (the increase the ratio of surface area to volume or get much smaller) is desired since it serves the needs of the system and the principles.

Simple mixing by stirring can readily result in inadequate blending or long-term blending that expends equipment and funds due to the difficulty of achieving uniform mixing or homogenization. Since the mixing devices are constantly subjected to corrosive environments, breakage and system failures are frequent and require back-up or redundant tanks to hold the liquids being treated in order to recover 'lost' equipment and repair the system.

Scrubbers introduce a variety of shortcomings as air cleansing devices. One drawback is the tendency of hydrophobic particulates, liquids, or vapors (oily or greasy gas or gases) to resist wetting in varying degrees. Adding a surfactant may simply result in some portion of the pollutants becoming 'wet' while other components remain on the surface of the water droplets or film. Since the intent of such a scrubber is to merely entrain such pollutants in water, an auxiliary waste-water treatment plant or facility must be incorporated in the system in order to render such pollutants safe to be discharged to either a sewer or to be recycled.

Another major drawback or shortcoming is the size (footprint') of the scrubber. The expense, energy demands, and manpower input required to operate and maintain such a device or devices may be prohibitive.

Electrostatic precipitators (ESPs) have a variety of shortcomings as well as having certain merits. Generally, the ESP 'collects' or deposits charged particles to a plate or medium having a charge opposite that of the targeted particles. In many instances, charges to the surface of these particles are brought about by having the particles receive a charge within an ionized zone. Thus, negatively and positively-charged particles collect upon the surface of the precipitator plates having charges opposite that of the particles. At intervals, the power flow may be halted by such deposits building up at specific sites to the extent that 'bridging' of the mass extends to both plates, resulting in 'shorting' and loss of effectiveness. This may result in the particles being freed from the attractive surfaces and falling (precipitating) to a collector device for removal or disposal or disposition. Such 'charging' may have little or no effect upon 'neutrally-charged' particles which simply pass between the plates or panels of the precipitator and thence leave in the exhaust stream.

Should a film of oil or grease form on any surface of the ESP, that surface will not release the attracted particles and require cleaning or replacement.

An ESP does little or nothing to change the pollutant's chemistry and was not so designed, since it serves primarily as a collector. Such ESPs require careful handling and attendance of the operators and thus require considerable capital outlay for both installation and usage. Additional problems arise when the collected or amassed pollutants require disposition.

Catalysts have a variety of shortcomings when applied to highly varied or polluted environments. While catalysts can be very effective in specific reactions, they may be 'poisoned' or inactivated by being coated with hydrocarbons or by the deposition of a film upon the surface of the catalyst (such as sulfur in some form). Other catalysts must be heated to a specific temperature to function and then be maintained within a specified temperature range in order to continue that function. This can be very difficult to maintain in very cold environments.

Many catalysts are very expensive, especially those using any of the platinum-group metals. Although such catalysts can be very effective, they are quite subject to poisoning or inactivation and must be replaced at intervals. Theft of the catalysts is always a problem and replacement can be problematic since the manufacturers of such products may be foreign and actually manufacture them in very small quantities.

SUMMARY OF THE INVENTION

I. Invention Description:

The modified homogenizer unit (FIG. 1) includes an integrated unit having a much expanded housing (FIG. 1, 9) (as compared to the original invention) that is intended to contain a replaceable ante-mixing chamber containing various packings, baffles, and/or sorbents. The housing, 9, also has top-mounted ports. The central port, 1, is dedicated to the input of water or a similar solvent mixture. One port or several ports, 2, is/are dedicated to entry of a gas, gases, liquid, liquids, any type of particle or mixture of particulates that will pass through the port, the ante-mixing chamber or mixing chamber, or any mixture of gas, liquid, or particulates into an ante-mixing chamber.

Another configuration of the homogenizer unit is depicted by FIG. 2. This homogenizer has a uniformly cylindrical housing (9). The entry port for water or a similar solvent is positioned laterally, 1. while two lateral ports are situated uppermost on opposite aspects, 2, of the housing, 8. These ports are for entry of a pollution stream or streams.

FIG. 1a depicts a centro/vertical section through the modified homogenizer unit (with the expanded ante-mixing chamber) so as to illustrate the internal structure of this same homogenizer unit (except for the retention chamber and discharge tube). The components are numerically identified as follows:

1. water or other solvent intake port and jet or nozzle
2. pollutant stream port or ports
3. ante-mixing chamber
4. mixing chamber
5. ante-mixing chamber housing
6. lateral extent of mixing chamber
7. venturi throat
8. venturi
9. homogenizer housing
10. ante-mix chamber support
11. ante-mixing chamber screen supports.

FIG. 2a depicts a centro-vertical section through a second version of the modified cylindrical homogenizer. The components have equivalent names and numbers, thus the above component list does not require duplication.

Headspace modifications or embodiments (FIG. 3) may include a mechanical mixer, 15, mounted on a shaft, 14, driven by an electric motor, 13. This allows for more thorough mixing of a pollutant stream and a reactive gas. This reactive gas enters the headspace region by one or more ports (FIG. 4) by passing through a perforated bulkhead, 16, that is mounted within the homogenizer housing, 9. A single transfer tube or line, 17, allows for passage of a reactive gas into the headspace of the homogenizer. Mixing may be done by a mechanical mixer (FIG. 3, 15) or by casual mixing while flowing into the ante-mix chamber. This port(s) may be positioned on the homogenizer housing or one or all intake ports other than water (for this modification).

The ante-mix chamber as depicted in perspective vertical quarter section (FIG. 1a, 3 and vertical section depictions (FIG. 2a, 3) of the homogenizer units may be cylindrical in structure and fit tightly within the ante-mixing chamber and directly superior to the mixing chambers of the homogenizers. The ante-mixing chambers depicted in FIGS. 1a, 3 and 2a, 3, include the exterior housing (FIG. 1a, 5), the interior housing (FIG. 4, 16) the top and bottom support screens (FIG. 1a, 11 and FIG. 2a, 11). This ante-mixing chamber for the homogenizer unit depicted by FIGS. 1 and 1a has a central and cylindrical channel that allows for the water jet (FIG. 1a, 1) to pass centrally through this chamber.

The ante-mixing chambers are supported both laterally and centrally by circular ante-mixing chamber supports (FIG. 1a, 10 and FIG. 2a, 10).

The perforations in the upper and lower screens of the ante-mixing chambers may have a variety of designs ranging from hexagonal (FIG. 6a), circular (FIG. 6b), square (FIG. 6c), to diamond-shaped (FIG. 6d). These perforations allow for circulation of gas through them while containing and supporting the various packings within the chambers.

These 'packings' are varied in configuration and may be Bioballs® (FIG. 7a) or any other similar configuration, baffles (FIG. 7b) having any configuration, cross-section, and surface treatment.

Water and a solvent or solvents containing water and another reactive chemical is delivered to the mixing chamber by a jet or jets. Although four configurations are depicted (FIG. 8a, 8b, 8c, 8d), these are not to be misconstrued as the only configurations that are possible. Each jet could have a different reactive solution it could transfer to the mixing chamber of the homogenizer unit or all may transfer the same type of liquid. The homogenizer unit mixing chamber (FIG. 9a, 4) and FIG. 9b, 4 are positioned between the jet(s) and above the venturi(s) of the homogenizer unit(s). Although the boundaries of this mixing chamber are not well-defined, this region is the uppermost area wherein the pollutants encounter the reactive solvent(s) and begin mixing (FIGS. 10a and 10b) before entering the throat (FIG. 10a, 4 and FIG. 2a, 4) of the venturi (FIG. 11a, 8 and FIG. 2a, 8).

It is within the venturi that the pollutant and/or pollutants or reactant stream or streams come into intimate contact with each other. A variety of chemical and physico-chemical reactions occur at this point.

A variety of surface treatments and modifications allow for more thorough mixing of the solvent and pollutants. A smooth venturi surface (FIG. 11a) is one option, while a circularly ridged or grooved surface (FIG. 11b), a surface with vertical vanes (FIG. 11c) allows for furthering certain reactions, and a radially-grooved surface (FIG. 11d can be used. If required, a series of gas or liquid ports can be machined into the venturi (FIG. 11e).

Passing a gas-liquid mixture through the venturi results in having the reactive solvent and pollutants continue into the retention chamber or chambers (FIG. 9a, 18) where further mixing occurs. This region also allows for a slight delay in flows due to its larger diameter resulting in lowered pressure. This retention chamber may have a series of spherical chambers (FIG. 12a), be baffled (FIG. 12b), have a centrally-located spiral conduit (FIG. 12c), or the serial spherical chambers may have a centrally-located spoiler 'ball' or bead (FIG. 12d).

The terminal reactions between the reactive solvent and the pollutants occurs prior to the liquid being discharged as a liquid into a vessel or vessels containing the same solvent. FIG. 9a, 18 depicts a straight, cylindrical retention chamber having a cone-shaped terminus. FIG. 13a depicts the extreme lower end of the retention chamber as having four, equi-spaced lateral discharge ports. These ports can be produced into tubular form as in FIG. 13b, or continued on to form a 'j-tube' as in FIG. 13c.

Note: The liquid or liquids may contain a wide variety of chemical compounds that require modification by ion substitution to yield a desired end product. A variety of configurations of the incoming and integrated ports and conduits and internal or in-line devices result in the chemical or physical modification or substitutions of the gas, gases, liquid, liquids, particles, or particulates, or any mixture of these entities.

Further, the interior configuration of the mixing chamber of the homogenizer unit may have a variety of surface textures, or conduits and ports of entry for reactive gases and/or liquids. The venturi surfaces may be smooth, textured, vaned, grooved, stepped, or have a surface configuration that enhances both mixing of the pollutant or reactant streams with additional reactants. Other vaned or grooved surfaces located below the venturi or venturis may cause the stream or streams to blend and swirl or tumble (as with stepped surfaces) so as to generate the maximum exposure and blending of the reactants to one another thereby prolonging reaction rates and times.

The retention chamber also serves as the discharge conduit for the homogenizer unit. This chamber or these chambers also serve to increase the reaction time or times between ions and reactants by delaying or shunting the flow of the stream or streams over a variety of surfaces and through a variety of media. Upon leaving the retention chamber, the stream flow may be directed by a variety of devices to some point that is remote from the entry port of the recirculating pump. This is to prevent 'channeling' of the stream, thereby assuring better and thorough mixing of the reactants in the reservoirs. Various chemical and physico-chemical reactions are also affected by the retention chamber.

The ancillary modifications or embodiments to the homogenizer unit result in more uniform mixing of incoming entities to the homogenizer unit. They also result in the increase of safety margins by containing the chemical and physical reactions within an aqueous medium, thereby both containing out-gassing and heat generation from exothermic reactions while also cooling any such reaction by rapidly diluting the reactants.

Chemical reactions can be more precisely controlled via elimination of atmospheric impingements, having control of the pressure and mixing of reactants within the homogenizer unit(s).

II. Homogenizer Applications

The following list does not include every type or kind of hardware or dry good manufacturing facility, food processor/manufacturer, mill operation, care and/or service provider, fabricator, agricultural operation, beverage manufacturer, recycler, or similar operations. Rather, the intent is to offer a much-simplified listing of some of the applications of the patented homogenizer unit and its ancillary improvements or modifications. An application of one type, such as dust control, also may qualify the homogenizer for other industries having similar needs and requirements; thus what is listed as a single type or kind of industry will apply to all of the industries of a like nature.

Certain abbreviations are offered within the compilations. They are: VOCs for Volatile Organic Compounds, NOx for nitrogen oxides, SOx for sulfur oxides, PM2.5 or PM10 are for particulate matter of 2.5 or 10 microns diameters, respectively. Granular Activated Carbon is abbreviated to GAC and Metal Recovery System is abbreviated to MRS.

Volatile acids are those organic acids that readily vaporize and are detected by their odors, such as butyric acids lending the smell of butter to the air. Free fatty acids are derived from plant and animal sources and are readily soluble or miscible in water. Potassium hydroxide, or KOH, is a compound that complexes with carbon dioxide to form potassium carbonate, thereby preventing the gaseous carbon dioxide from entering the atmosphere.

Certain arenas of activity may appear to be disparate, but they all serve the same or similar purpose, that is, having a number of people within close proximity in a confined space. Treating these arenas in much the same manner is therefore reasonable since the applications are based on scale, not on the space being treated.

So many types of laboratories exist that each will/may require specific systems be utilized to deal with innate problems. The same problem arises within the metals and plastic industries, therefore, a listing is very general rather than comprehensive and detailed.

One embodiment is directed to apparatus and methods that may be employed for introducing nutrients into a water stream to provide an aqueous nutrient solution for hydroponics plant growth. Such a PPH apparatus may be any of those configurations described herein, and in one embodiment may further include an insulated jacket around such components as the inlets, the ante-chamber, the venturi, and the outlet to maintain the nutrient solution at a temperature below ambient temperature so as to increase dissolution of oxygen, nitrogen, or both into the aqueous nutrient solution. Where a retention chamber is provided within the PPH, it of course may also be insulated.

According to one embodiment, a method for introducing nutrients into a water stream to provide an aqueous nutrient solution for hydroponics plant growth may comprise introducing a nutrient stream into a mixing zone through an inlet, introducing a water stream into the mixing zone through a separate water inlet such that the water stream is commingled with the nutrient stream upon both streams entering the mixing zone, passing the commingled streams through a venturi so as to homogenize the streams such that materials within the nutrient stream are homogenously dispersed within the water stream, and conveying the resulting aqueous nutrient solution stream exiting the venturi to roots of hydroponically grown plants to provide nutrients for the growth of the plants. Of course, the aqueous nutrient solution could also be conveyed to other hydroponics or aquaponics grown organisms (e.g., algae farms, fish farms, etc.)

In one embodiment, the streams may be cooled to provide and maintain the nutrient solution at a temperature below ambient temperature so as to increase dissolution of oxygen, nitrogen, or both into the aqueous nutrient solution. Oxygen, nitrogen, or both may be injected into one or both of the streams so as to provide a relatively high level (e.g., 8 to 12 ppm) of such gases dissolved within the aqueous nutrient solution.

Another embodiment may be directed to methods and related systems for purifying a biogas or other stream containing methane using a PPH. Such a method may include introducing a raw methane stream into a mixing zone through an inlet, the raw methane stream including methane and one or more contaminants selected from the group consisting of carbon dioxide, ammonia, hydrogen sulfide and combinations thereof. A water stream may be introduced into the mixing zone through a separate water inlet such that the water stream is commingled with the raw methane stream upon both streams entering the mixing zone. The commingled streams may be passed through a venturi of the PPH so as to homogenize the streams such that one or more contaminants within the raw methane stream are dispersed within the water stream, forming a contaminant isolation stream including the one or more contaminants and a purified methane stream. The water stream may advantageously be chilled to below ambient temperature to increase dissolution of the one or more gaseous contaminants therein. Such systems and methods have been found to be particularly effective and inexpensive in removal of carbon dioxide, hydrogen sulfide, and/or other contaminants from the raw methane input stream (e.g., 90% or better purity, with little or no detectable $H_2S$ present).

Homogenizer Applications

| Site or Area of Usage | Specific Pollutant(s) | Surfactant Required | Oxidizer Required | Solvent Required | Sorbent Required | Bleed & Feed/ Flush |
|---|---|---|---|---|---|---|
| 1. Living Room | dust mites, dandruff. lint, odors, smoke | yes | no | water | no | yes |
| 2. Kitchen | grease aerosols smoke, food odors, detergent aerosols | yes | no | water | no | yes |
| 3. Garage/ Workshop | exhaust, paint solvents and odors, dust, air borne particles, smoke | yes | no | water | no | ? |
| 4. Laundry/ Utility Room | detergent odors, lint, dust, heat | yes | no | water | no | yes |
| 5. Nursery/ Sickroom | microbes, odors, lint, dust | yes | no | water | no | no |
| 6. Lavatory/ Restroom | odors, aerosols, moisture, microbes | yes | yes | water | no | yes |
| 7. Commercial Bakery | flour, spice dust, odors, grease aerosols. carbon dioxide | yes | yes | water | no | check local regulations |
| 8. Commercial Garage | carbon monoxide, carbon dioxide, smoke, paint overspray, solvents, odors | yes | yes | water | GAC | check local regulations |
| 9. Auto Body & Paint Shop | carbon monoxide, carbon dioxide, paint & primer dust, overspray, | yes | yes | water | GAC | check local regulations |

-continued

| Site or Area of Usage | Specific Pollutant(s) | Surfactant Required | Oxidizer Required | Solvent Required | Sorbent Required | Bleed & Feed/ Flush |
|---|---|---|---|---|---|---|
| 10. Welding Shop | airborne solvents metal vapors, grinding dust, soot, smoke, paint primer overspray, | yes | yes | water & water-miscible solvent | GAC | check local regulations |
| 11. Woodshop | sawdust, wood dust, paint & primer overspray solvents, smoke | yes | yes | water | varies by shop | holding & classifier systems |
| 12. Metal Foundry | metal vapors, grinding dust, soot, smoke, solvents & odors from molding area, heat | yes | ? | water & acid | GAC | metal recovery system (MRS) |
| 13. Leaded Glass Shop | metal vapors, soldering smoke | yes | no | water | none | MRS |
| 14. Sign Shop | ink, solvents | yes | no | water & alcohol | GAC | drain & treat |
| 15. Crematoria | mercury vapor, volatile fatty acids | yes | no | dilute acid in water | copper | drain & treat |
| 16. Beauty Shop | solvents, lacquer spray, dandruff | yes | no | water | GAC | flush to sewer |
| 17. Pet Shop | dandruff, hair, soap odors, perfumes | yes | no | water | no | flush to sewer |
| 18. Pet Groomer | 'wet dog' odors, hair, dandruff, detergent odors, perfume | yes | no | water | no | flush to sewer |
| 19. Funeral Home | embalming fluid fumes, putrescein, cadaverein, odors | yes | yes | water | GAC | flush to sewer |
| 20. Paper Recycling | paper dust, linter, aromatics, boron oxides | yes | yes | water | GAC | treat as hazardous waste |
| 21. Sawmill | wood dust, chips, smoke, dirt, aromatics, volatile oils | yes | yes | water | GAC | dry solids & incinerate or recycle |
| 22. Wood Incineration | smoke, volatile acids & organics, benz(o) pyrenes, particulates, soot | yes | yes | water | GAC | store & oxidize solids & organics, bio-treat |
| 23. Doctor's Office & Waiting Rooms | microbes, odors, dust, perfumes, dandruff, antiseptics | yes | yes | water | no | enhanced ozone treatment |

-continued

| Site or Area of Usage | Specific Pollutant(s) | Surfactant Required | Oxidizer Required | Solvent Required | Sorbent Required | Bleed & Feed/ Flush |
|---|---|---|---|---|---|---|
| 24. Passenger Planes | microbes, odors, dust, lint, perfumes, dandruff, carbon dioxide | yes | yes | aqueous KOH | no | dump & discharge at destinations |
| 25. Laundries | soap & detergent dust, lint, volatile fatty acids, perfumes, solvents | yes | yes | water | GAC | flush & recharge |
| 26. Dry Cleaners | solvents, dirt, dust, dandruff, volatile fatty acids | yes | yes | water | GAC | flush if allowed |
| 27. Automotive Exhaust Shops | carbon monoxide, carbon dioxide, welding vapors & fumes, metal vapors, asbestos, dust, dirt | yes | yes | water + KOH | zeolites | flush to sewer if allowed |
| 28. Appliance Repair Shop | ozone, dirt, dust, soldering vapors, scorched & burnt plastics, paint odors | yes | yes | water + KOH | Zeolites + GAC | flush to sewer if allowed |
| 29. Waste Incinerator | smoke, dust, pyrenes & carcinogens, vapors, water, VOCs*, NOx*, SOx*, PM2.5*, PM10*, volatile fatty acids. ammonia | yes | yes | water + KOH | zeolites + GAC | MRS |
| 30. Dairy | volatile fatty acids, detergent odors, dandruff, dust, butyric acids, ammonia, methane, pesticides | yes | yes | yes | zeolites, GAC | bleed to methane generator |
| 31. Milk Room | dandruff, hair, volatile fatty acids, butyric acids | yes | yes | yes | GAC | bleed to methane generator |
| 32. Rock Cutting Operations | rock & metal dusts, sulfur oxides | ? | no | yes | GAC | settling basin, MRS |

-continued

| Site or Area of Usage | Specific Pollutant(s) | Surfactant Required | Oxidizer Required | Solvent Required | Sorbent Required | Bleed & Feed/Flush |
|---|---|---|---|---|---|---|
| 33. Explosives Manufacturing Preparation | airborne nitrates, smoke. paper lint and dust, strong oxidizer fumes | yes | yes | yes | GAC, zeolites | bleed to biodegrade-dation facility |
| 34. Engine Test Shop | carbon monoxide, carbon dioxide grease & oil vapors, smoke, VOCs, SOx, NOx, PM2.5, PM10, metal vapors, unburned fuel | yes | yes | yes | GAC, zeolites | bleed to sump for further treatment |
| 35. Stationary and Active Rocket Testing | aluminum oxide, perchlorates, HCl, ammonia, heat, water | yes | yes | water | GAC, zeolites | bleed to settling basin for further treatment |
| 36. Metals Extraction Facility | specific to element | yes | yes | water + acids | none | MRS |
| 37. Petroleum Refinery | specific to compounds | yes | yes | water + organic solvents | GAC, zeolites | bleed to treatment facility |
| 38. Electrical Power Generator | fuel specific VOCs, NOx, SOx, metal vapors, carbon monoxide, carbon dioxide, PM10, PM2.5, water, ammonia | yes | yes | water + KOH | GAC, zeolites | bleed to treatment facility |
| 39. Diesel Repair Shop | VOCs, NOx, SOx, metal vapors, soot, dirt | yes | yes | water + KOH | GAC + zeolites | bleed to treatment Facility |
| 40. Coal Crusher | large particulates, PM10, PM2.5, ammonia, water | yes | no | water + KOH | GAC + zeolites | bleed to treatment facility |
| 41. Rock Crusher | large particulates, PM2.5, PM10, water, metal dust sulfur dust, asbestos | yes | no | water | ? | bleed to settling basin |
| 42. Poultry Farms | ammonia, feather mites, dust, fecal dust, odors | yes | yes | water + KOH | zeolites | bleed to holding basin or tanks for further treatment |
| 43. Hog Farms | ammonia, dust, dandruff, dirt, free fatty & volatile acids, methane, | yes | yes | water + KOH | zeolites (bio-char) | bleed to treatment facility for further treatment |

-continued

| Site or Area of Usage | Specific Pollutant(s) | Surfactant Required | Oxidizer Required | Solvent Required | Sorbent Required | Bleed & Feed/ Flush |
|---|---|---|---|---|---|---|
| 44. Dairy Farms, Stock Yards, Horse Paddocks | urine & fecal odors ammonia, dandruff, hair, animal odors, urine & fecal odors, methane, fecal dust, free & volatile fatty acids | yes | yes | water + KOH | zeolites (bio-char) | bleed to methane generator after carbonate removal |
| 45. Fur Farms | ammonia, musky odors fecal dust, dandruff, hair, cadaverine, putrescein, wood dust, volatile acids | yes | yes | water + KOH | zeolites | bleed to storage tank for further treatment |
| 46. Waterfowl Farms | ammonia, feather dust, amines, dandruff, methane | yes | yes | water + KOH | GAC, zeolites | bleed to storage tank for further treatment |
| 47. Breweries, Fermenters, Distillers | carbon dioxide, alcohols, smoke, yeast odors, volatile congeners | yes | no | water + KOH | GAC | bleed to alcohol recovery facility |
| 48. Food Pickling Facilities | carbon dioxide, alcohol, salt dust, spice dust, vinegar, volatile congeners | no | no | water + KOH | none | bleed to distilling facility |
| 49. Cotton Gins | cotton linters, dust, volatile fatty acids | yes | no | water | filter | bleed liquor to treatment facility |
| 50. Feed Mills | dust, fish meal stench, seed hulls, dust, dirt, plant fibrils, volatile fatty acids, PMs | yes | no | water | filter | bleed liquor to sewer |
| 51. Grain Silos | dust, plant fibrils, insect parts, exhaust vapors | yes | yes | water | filter | bleed liquor to sewer or settling ponds |
| 52. Sugar Mills | dirt, sugar dust, acid vapors, limestone dust | yes | yes | water | none | bleed liquid to treatment pond or tank for ethanol generation |
| 53. Plywood, Synthetic Wood Manuf. | sawdust, wood chips, dirt, solvents, steam, volatile aromatics | yes | yes? | water | none | bleed liquid to dryer and incinerate solids |

-continued

| Site or Area of Usage | Specific Pollutant(s) | Surfactant Required | Oxidizer Required | Solvent Required | Sorbent Required | Bleed & Feed/ Flush |
|---|---|---|---|---|---|---|
| 54. Plastic Casting Operations | solvents, epoxy odors, plastic dust, release agents, paints, overspray | yes | yes | water | GAC | bleed to sewer if allowed |
| 55. Cosmetics Manuf. | talc, dust, perfumes, musk, volatile oils, pigment dust & aerosols | yes | yes | water | filter | settle in storage facility and landfill if allowed |
| 56. Fiberglass Lay-Up & Repair Shops | glass and other fibers, grinding dust, volatile peroxides, solvents | yes | yes | water | filter | solids to landfill if allowed; liquid to sewer |
| 57. Blueprint Shops | ammonia | no | no | water + sulfuric acid | none | liquid to recovery system |
| 58. Metal Drawing & Shaping | oil vapors, solvents, metal dust and scale, drawing oil waste | yes | no | water | none | liquid to oil recovery system |
| 59. Stone and Concrete Monument Manuf. | rock dust, asbestos, solvents, volatile organic acids, epoxy dust, airborne particulates, mold release agents | yes | no | water | none | liquid to settling facility; flush clarified liquid to sewer or recycle |
| 60. Glass Manuf. | silica aerosols & vapor, metal vapors, dust, soot from gas or coal combustion | yes | no | water | none | liquid to settling facility, flush clarified liquid |
| 61. Jewelry Manuf. | solder and metal vapors, furnace vapors, polishing dust, etching vapors | yes | no | water | none | liquid to settling; reclaim solids for precious metals recovery |
| 62. Meat & Fish Smokers/Dryers | smoke residue, volatile fatty acids, pyrenes, odor, ammonia | yes | yes | water + KOH | GAC | liquid smoke recovery is part of process, rest of liquids to sewer |
| 63. Butcher Shops | volatile fatty acids, blood & meat odors | yes | no | water | none | flush to sewer |
| 64. Restaurants | detergent odors, smoke from grill & kitchen | yes | no | water | none | flush to sewer |
| 65. Restrooms | Fecal & urine odors, microbes, perfumes | yes | no | water | none | flush to sewer |

-continued

| Site or Area of Usage | Specific Pollutant(s) | Surfactant Required | Oxidizer Required | Solvent Required | Sorbent Required | Bleed & Feed/ Flush |
|---|---|---|---|---|---|---|
| 66. Spice & Flavoring Producer | volatile odors & fatty acids, piperazines, amines, flavenoids, dust | yes | no | water | none | flush to sewer if allowed |
| 67. Barbeque Grills | smoke, volatile fatty acids | yes | no | water | none | flush to sewer |
| 68. Quarries | rock dust, explosive fumes & vapors | yes | no | water | none | liquid to settling basin for bio-treatment. solids to disposal area |
| 69. Sand & Gravel Operations | dust, fine sand & clay, exhaust from equipment | no | no | water | none | liquid to settling basin, recycle clarified liquid |
| 70. Metal Salvage Yards, Shredders | solvents, metal & paint dust, airborne particulates, waste fuel and liquids, grease & dust, dirt | yes | yes | water | none | liquid to fractionator, recycle hydrocarbons, reclaim metal dust & non-aqueous liquids |
| 71. Wood Preservation Facilities | copper arsenate, pentachlora-phenols, dust, dirt | yes | yes | water | none | evaporate water, incinerate solids & treat exhaust |
| 72. Leather Processors & Tanneries | metal dye aerosols, volatile fatty acids, dandruff, hair & skin particles, salt dust, odors | yes | yes | water | GAC, zeolites, filter | evaporate liquid, solids to landfill if allowed or incinerate and recover metals |
| 73. Snack Food Manuf. | volatile fatty acids, butyric acids, steam, dust, dirt, cleaning agents | yes | no | water | none | flush to sewer if allowed after starch recovery |
| 74. Salt (NaCl) Preparation | salt dust, aluminum dust, iodine vapor | no | no | water | none | liquid to evaporators, recycle solids |
| 75. Paint Manuf., Paint Formulation Labs. | metal & pigment dust, solvents, latex odors, drying oils and dirt | yes | yes | water | GAC, zeolites, filter | clarify & recycle solids |
| 76. Chemical Fertilizer Manuf. | varies with product | no | no | water | none | evaporate water & recycle solids |
| 77. Cloth, Carpet & Thread Manuf. | lint, fabric & pigment dust, solvent & adhesive fumes | yes | no | water | filter | recycle liquid. recycle, landfill, or incinerate solids |

-continued

| Site or Area of Usage | Specific Pollutant(s) | Surfactant Required | Oxidizer Required | Solvent Required | Sorbent Required | Bleed & Feed/ Flush |
| --- | --- | --- | --- | --- | --- | --- |
| 78. Oil & Gas Well Heads | hydrogen sulfide, halogens in water, gaseous hydrocarbon vapors, radioactive agents, volatile fatty acids, mercury & other metal vapors, exhaust from equipment | yes | no | water | special treatment | trap and sell clean gases, convert hydrogen sulfide to sulfuric acid or sulfur-based compounds |
| 79. Specialty Cheese Makers | smoke, particulates, volatile fatty acids, steam, milk odors | yes | yes | water | none | flush to sewer after primary treatment |
| 80. Slaughter Houses | volatile fatty acids, smoke, steam, blood odors, cadaverine, putrescein, fecal & urine odors, dandruff & hair, dust, dirt, greasy emissions, detergents | Yes | yes | water | varies | should have on-site water treatment facility |
| 81. Canneries | varies with product | Yes | ? | water | ? | flush to holding tanks for treatment |
| 82. Newspaper Print Facilities | paper lint, dust, solvents, ink dust | Yes | no | water | none filter solids for disposal | flush liquid to sewer if allowed |
| 83. Kennels, Veterinary Facilities | ammonia, fecal & urine odors, hair, dandruff, cleaning agents, volatile fatty acids | yes | no | water | none | flush to sewer if allowed |
| 84. Glass Etchers & Engravers | etching acids, ammonium bifluoride, airborne silica particles | no | no | water | none | filter to remove solids. treat liquid as hazardous waste |
| 85. Sand Blasters | silica dust, dust, metal & paint dust | yes | no | water | none | filter to remove solids for recycling of liquid |
| 86. Aviaries | ammonia, microbes, bird dandruff, fine dust | yes | yes | water | zeolites | flush to sewer if allowed |
| 87. Culinary Water Treatment Facilities | halogen vapors, ozone | no | no | water + KOH, water + sulfuric acid for ozone | none | flush to sewer |

-continued

| Site or Area of Usage | Specific Pollutant(s) | Surfactant Required | Oxidizer Required | Solvent Required | Sorbent Required | Bleed & Feed/ Flush |
|---|---|---|---|---|---|---|
| 88. Waste Water Treatment | ammonia, fecal & urine odors, detergent odors, myriad of microbes, etc. | yes | yes | water | none | recycle through facility |
| 89. Fisheries & Fish Culture Fish Processing | ammonia, amines, fish & feed odors, sulfur-based odors, volatile fatty acids | yes | no | water | none | flush to waste treatment pond(s), dry solids |
| 90. Home Fireplaces | smoke, volatile fatty acids, pyrenes, terpenes, VOCs, odorants, carbon monoxide, carbon dioxide, particulates, NOx, SOx, fly ash | yes | no | water | none | flush to sewer if allowed |
| 91. Hotel Kitchens | smoke, volatile fatty acids, grease vapors, VOCs, detergent dust & odors, steam | yes | no | water | none | flush to sewer if allowed |
| 92. Hotel Laundries | lint, dandruff, volatile fatty acids, detergents, perfumes, deodorants, dust | yes | no | water | none | flush to sewer if allowed |
| 93. Parking Terraces & Garages, Automobile Inspection and Emissions Shops | dust, dirt, rubber and salt dust, particulates, SOx, NOx, carbon Monoxide, carbon dioxide | yes | no | water | none | flush to sewer if allowed after skimming oil |
| 94. Oil Sumps in Truck and Bus Garages | volatile fatty acids, amines, microbes, organic solvents, waste fuel & grease, detergents | yes | yes | water | none | bleed to treatment facility to separate solids from oily mass |
| 95. Jails, Prisons, Spas, Saunas, Conference & Class Rooms, Health Centers, Preschools, Other Enclosed Arenas Such as Churches | dandruff, dust, dirt, perfumes, volatile fatty acids, amines, microbes | yes | no | water | none | flush to sewer |

-continued

| Site or Area of Usage | Specific Pollutant(s) | Surfactant Required | Oxidizer Required | Solvent Required | Sorbent Required | Bleed & Feed/ Flush |
|---|---|---|---|---|---|---|
| 96. Mobile & Stationary Asphalt Plants, Road Base Trucks, Tar Trucks and Melters | VOCs, dust, dirt, greases, Volatile fatty acids, smoke particulates | yes | yes | water | none | specific to needs |
| 97. Municipal Swimming Pools | chlorine fumes, water vapor | no | no | water + KOH | none | flush to sewer |
| 98. Geology Laboratory | rock dust, saw swarf, metal dust, grinding, polishing & potting compounds, solvents | no | no | water | none | bleed to clarifier, recycle water. landfill solids |
| 99. Organic Chemistry | specific to lab | yes | yes | water + ?? | GAC, zeolites | degrade with ozone, bio-degradation |
| 100. Inorganic Chemistry | specific to lab | yes | yes/no | water | specific to lab | varies |
| 101. Radiology Lab | specific to lab | specific to lab | no | specific to lab | none | specific to lab |
| 102. Analytical Chemistry | specific to lab | specific to lab | ? | ? | specific to lab | specific to lab |
| 103. Hematology, Blood Gas Lab | microbes, variety of reagents, dyes | yes | yes | water | none | flush after oxidation if allowed |
| 104. Spectral Labs | nitrates, chlorides, metal and non-metal vapors, highly varied | no | yes | water | GAC, zeolites | evaporate water, recycle solids |
| 105. Micro-biology | microbes, dust from media preparation, dust, vapors, odors | yes | yes | water | none | dry and incinerate solids |
| 106. Digestion & Fume Hoods | acid & base vapors, metal & non-metal vapors, organic & inorganic solvents, water, | yes | yes | water | GAC, zeolites | recycle solids after drying |
| 107. Botany Lab | VOCs, terpenes, solvents, staining chemicals | yes | no | water | GAC | flush to sewer if allowed |
| 108. Corrosion Testing, Environmental Lab | specific to lab | specific to lab | specific to lab | specific to lab | specific to lab | specific to lab |
| 109. Dental Lab and Office | mercury vapor, metal vapors, solvents, plasticizers | yes | yes | water | GAC, copper | flush to sewer after treatment |
| 110. Hospital Wards | microbes, odors, dust, lint, volatile fatty acids | yes | yes + ultra-violet light | water | none | flush to sewer if allowed |
| 111. Surgical Theater | volatile fatty acids, putrescein, cadaverine, microbes | yes | yes | water | none | dry, incinerate |

-continued

| Site or Area of Usage | Specific Pollutant(s) | Surfactant Required | Oxidizer Required | Solvent Required | Sorbent Required | Bleed & Feed/ Flush |
|---|---|---|---|---|---|---|
| 112. Hospital Kitchen | microbes, odors, detergents, aerosols | yes | no | water | none | flush to sewer |
| 113. Morgue | microbes, cadaverine, putrescein, embalming fluids, bleach, detergents, deodorants, body fluids | yes | yes | water | none | dry & incinerate |
| 114. Waiting Rooms | microbes. lint, dust, perfumes, aerosols, body odors | yes | yes | water | none | flush to sewer |
| 115. Carpet Cleaners | microbes, dust mites, food & drink residue, dirt, lint, odors, solvents | yes | yes | water | none | flush to Sewer |
| 116. Metal Forging, Casting, and Blacksmith Shops | metal dust, dirt, smoke, soot, particulates, oil smoke | yes | no | water | none | dry & recover solids |
| 117. Metal Casting Facilities | metal dust, metal vapors, smoke, dirt, soot, oil smoke, particulates, release agents | yes | no | water | GAC | dry & recover metals |
| 118. Tobacco Products Manuf. | microbes, fatty acids, congeners, plant fibrils, dirt, pesticides, additives to product | yes | yes | water | none | dry & incinerate |
| 119. Pesticide Manuf. | varies with product | yes | yes | water + organic solvents | GAC, zeolites | treat as hazardous waste |
| 120. Propellant Manuf. | varies with product | yes | yes | water | GAC, zeolites | bio-treat when possible; hazardous |
| 121. Paper Shredders | paper dust & lint, ink dust, clay dust | yes | no | water | none | settle, decant clarified liquid to sewer, dry solids |
| 122. Wood Shredders, Compost Manuf. | ammonia, dust, dirt, microbes, odors | yes | no | water + KOH | none | settle, decant clarified liquid, return solids to compost |
| 123. Greenhouses | microbes, carbon dioxide, dust, dirt | no | yes | water | none | flush to sewer |
| 124. Metal Plating Facilities | metal vapors, acid and alkali vapor & dust, | yes | yes | water | GAC, zeolites | recover metal sludge; dry and |

-continued

| Site or Area of Usage | Specific Pollutant(s) | Surfactant Required | Oxidizer Required | Solvent Required | Sorbent Required | Bleed & Feed/ Flush |
|---|---|---|---|---|---|---|
| | solvents, chlorine vapors, aerosols, dirt, dust, fiberglass fibers, resin particles, | | | | | discard liquid to sewer |
| 125. Circuit Board Laminating & Drilling, Printing | solvent vapors, resin & glass participates, organic film (resist) dusts, steam, paper lint | yes | no | water | none | recover drill & routing swarf, recycle; water to sewer |
| 126. Assay Labs | siliceous dust, borax dust, aerosols, metal vapors, smoke, dirt, non-metal vapors, radioactivity | yes | no | water | none | clarify water, recover solids for metals |
| 127. Cooling Towers | water vapor, volatile metal and non-metal vapors, amines, ammonia | no | no | water | GAC, zeolites | flush to sewer after solids recovered |
| 128. Indoor Shooting Ranges | lead and other metal dust and vapors, nitrate vapors, particulates | yes | no | water | zeolites | flush to sewer after solids recovered |
| 129. Crop Seed Processors | dirt, dust, plant fibrils, fragments, pesticides dust & residue | yes | no | water | none | flush to sewer if allowed |

BRIEF DESCRIPTION OF THE SEVERAL VIEWS OF THE DRAWINGS

A complete understanding of the ancillary embodiments to the homogenizer unit(s) may be obtained by reference to the accompanying drawings, when considered in conjunction with the subsequent, detailed descriptions, in which.

Aqueous solvent or another suitable solvent is mixed with the pollutant(s) in the mixing chamber and proceed downward through the venturi, 8.

Figure 2:
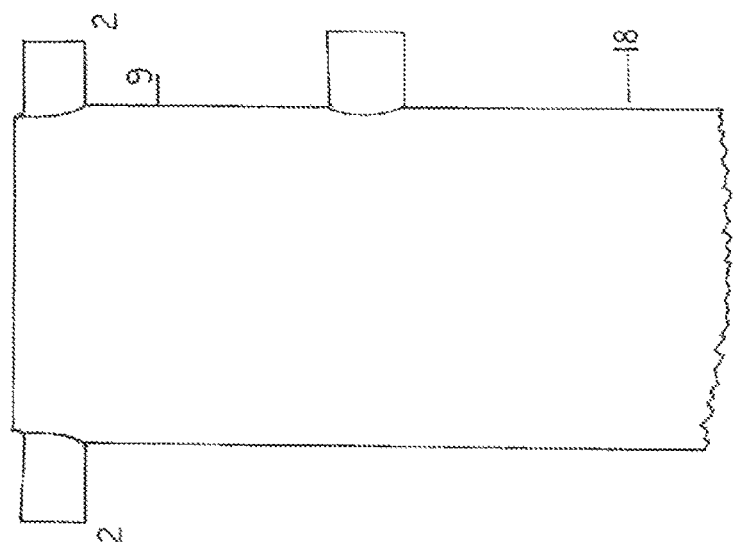

FIG. 2 is a lateral view of the exterior of a cylindrical homogenizer unit having two lateral entry ports for pollutant stream entry and a single lateral port for solvent entry.

Figure 2A:
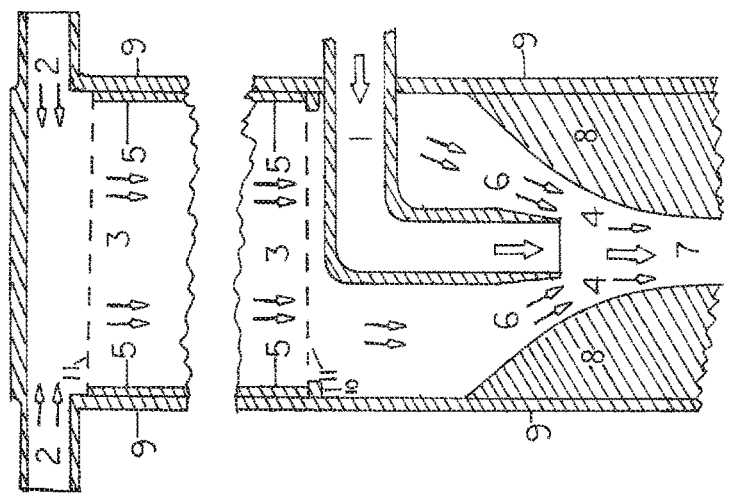

FIG. 2a is a central, longitudinal section of the same cylindrical homogenizer unit. The principal difference between 1a and 2a is the location of the water jet is lateral in 2a. This embodiment does nor require the ante-mixing chamber to be perforated by the water jet, thus also allowing for lateral positioning of the pollutant stream port(s).

In principle and operation, both homogenizer unit embodiments are equally effective related to activity and pre-mixing.

Figure 3:
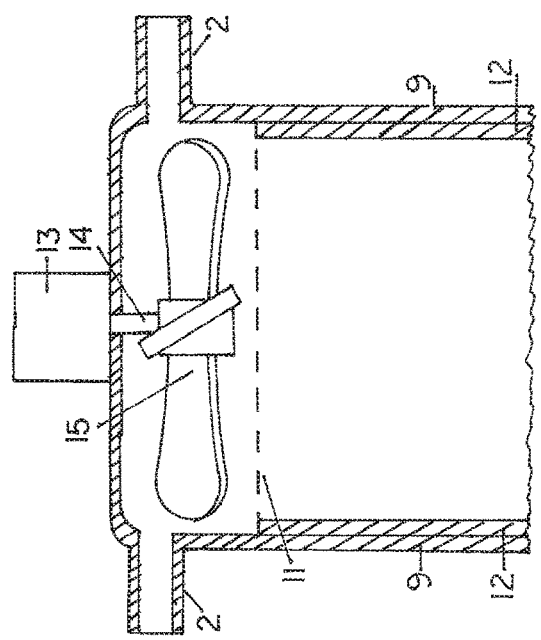

FIG. 3 depicts a mechanical mixer having rotating paddles, 15. mounted on a central shaft, 14, that is turned by an electric motor, 13. All other numbers on the figure relate to the same numbers presented in FIGS. 1a and 2a, respectively.

Figure 4:
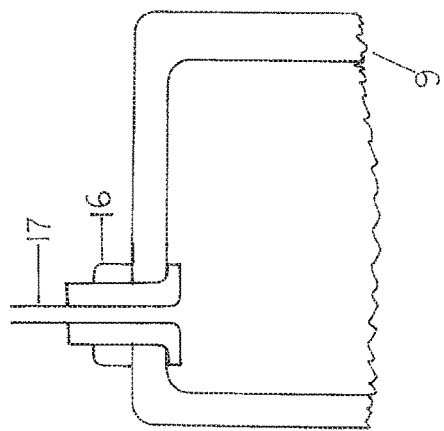

FIG. 4 depicts a portion of the homogenizer housing (FIG. 1a, 9 or FIG. 2a, 9) with a bulkhead, 16, and a single gas or reactive solution entry port, 17. The transfer tube or line passes through the bulkhead, which itself passes through the homogenizer unit housing. This allows for introduction of an oxidizing agent in gas or liquid phase to enter the homogenizer headspace. This port or ports may be located on a pollutant entry port or ports, a water jet or nozzle, or at any selected locus or loci on the homogenizer housing.

Figure 5:
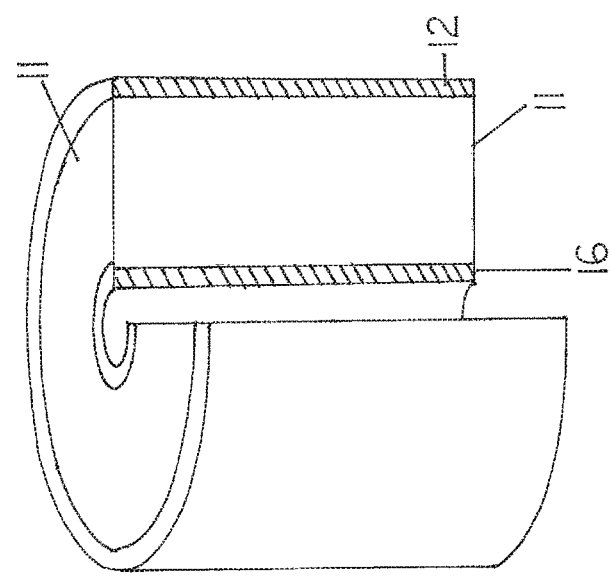

FIG. 5 depicts an ante chamber unit in perspective quarter section view. The screens, 11, are mounted on the top and bottom of the housing, 12. This ante-mixing chamber has the central channel, 16, as required for passage of the water jet, 1.

Figure 6B:
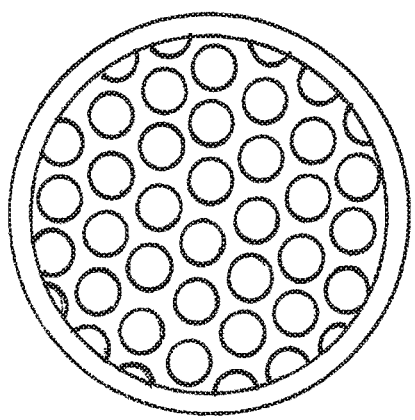
Figure 6D:
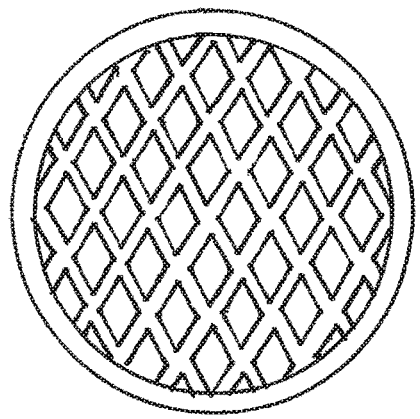
Figure 6A:
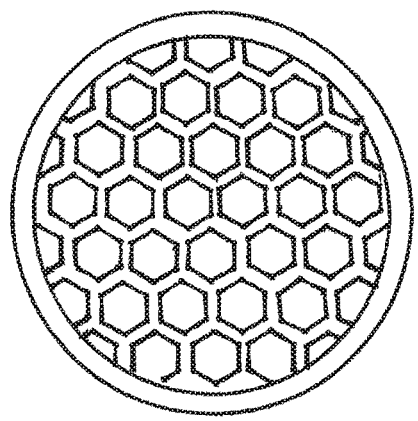
Figure 6C:
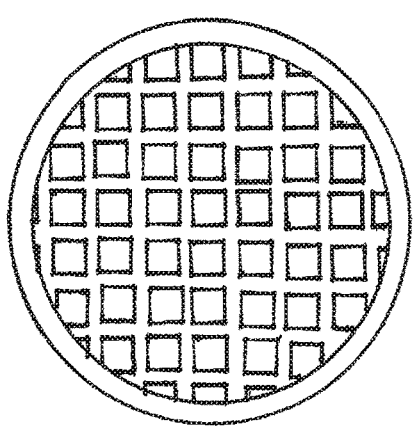

FIG. 6a depicts a screen with hexagonal perforations. FIG. 6b depicts a screen with circular or round perforations. FIG. 6c depicts a screen with square perforations and FIG. 6d depicts a screen with diamond-shaped perforations.

Figure 7A:
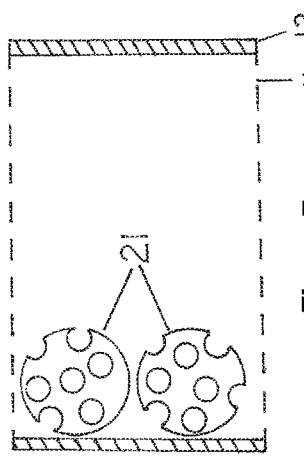

FIG. 7a depicts an ante-mixing chamber for the homogenizer design in FIGS. 2 and 2a. The numbers correspond to the same numbers in FIG. 1a, 2a, and FIG. 5. This ante-mixing chamber is 'packed' with Bioballs®, which are hollow plastic, perforated spheres, 21.

Figure 7B:
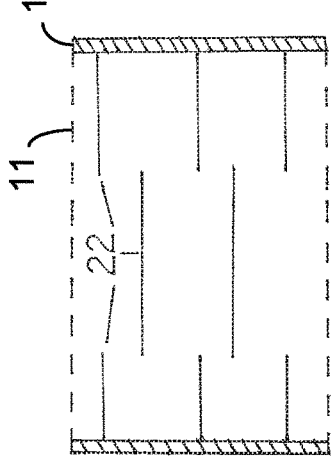

FIG. 7b depicts an ante-mixing chamber 'packed' with baffles mounted vertically and solidly against the top and bottom screens, 11, and chamber housing, 12.

NOTE: Baffles of any of the following shapes, profiles, or surfaces may be employed: circular or round, elliptic or elliptical, oval or ovoid, oblong, lanceolate or linear-lanceolate, bilobed or bifoliar, trilobed or trifoliar, cruciform or cross-shaped, square, rectangular, rhomboid or rhombohedral, triangular, sagittate or arrow-shaped, delta or deltoid, palmate, stellate or star-like, pentagonal or any 5-sided shape, hexagonal or any 6-sided shape, heptagonal or any 7-sided shape, octagonal or any 8-sided shape, any polygon, any diamond shape, any cardioid or heart shape, any reniform or kidney shape, any lobed form, any chevron-shaped form.

Any baffle having any of the following profiles or margins: lenticular (convexo-convex, plano-convex, convexo-concave, concavo-convex, plano-concave, concave-convex), bristled, linear, serrated, dentate, crenate, undulate, perforated, circular grooves-ridges, entire, lobed, notched, or any diminutive of the prior margins, profiles, or surfaces.

Any baffle having any surface treatment including smooth, pilose, rugose, corrugated, pitted in any manner, scabrose, scaled, imbricated, depressed or elevated vermiform, spiral or spirals, a whorl, whorls, or whorled, pebbled, spicate or speculate, woven, matte, matted, cross-hatched, radial grooving or ridging.

Figure 8A:
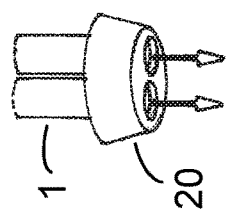
Figure 8B:
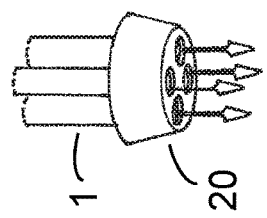
Figure 8C:
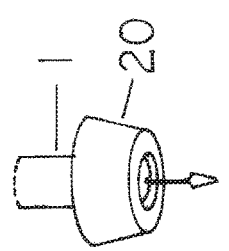
Figure 8D:
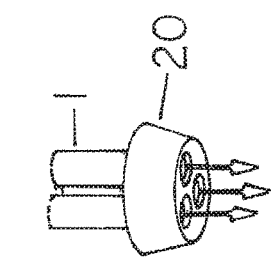

FIG. 8a depicts a single water or solvent jet within a tapered housing. This taper is advantageous to reduce spattering or lateral overspray. FIGS. 8b, 8c, and 8d depicts nozzles or jets having 2, 3, or 4 jets, respectively.

Figure 9A:
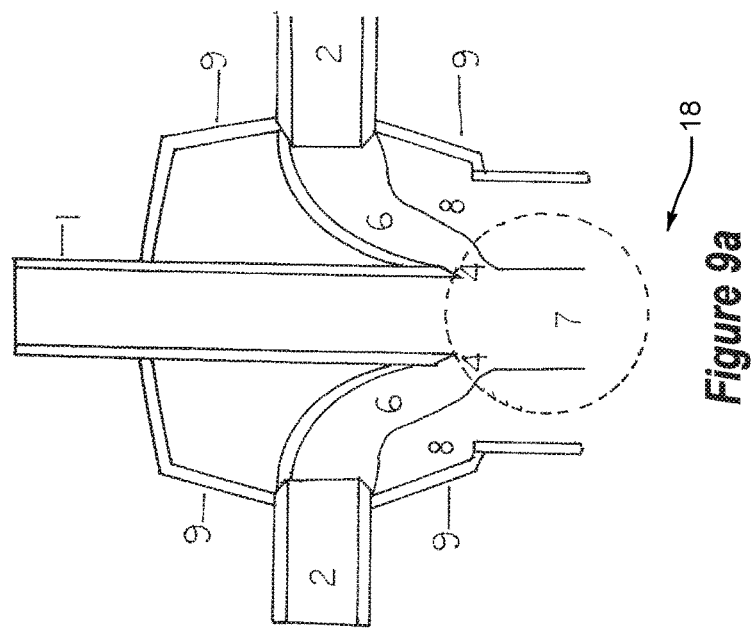

FIG. 9a depicts a vertical, longitudinal section of the upper portion of an homogenizer unit with the 'mixing chamber' encircled by a dashed circular line.

Figure 9B:
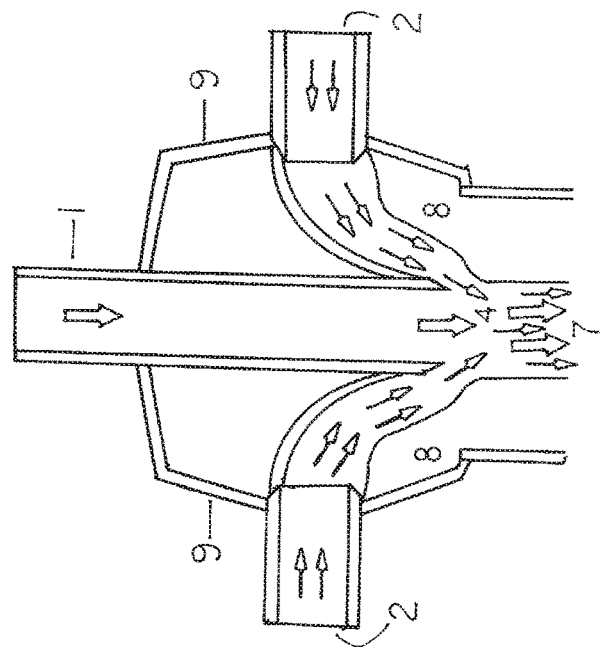

FIG. 9b depicts a lateral view of an homogenizer unit. Both the external view on the left of the drawing and the internal view on the right of the drawing are presented. The retention chamber, 18, is depicted.

Figure 10A:
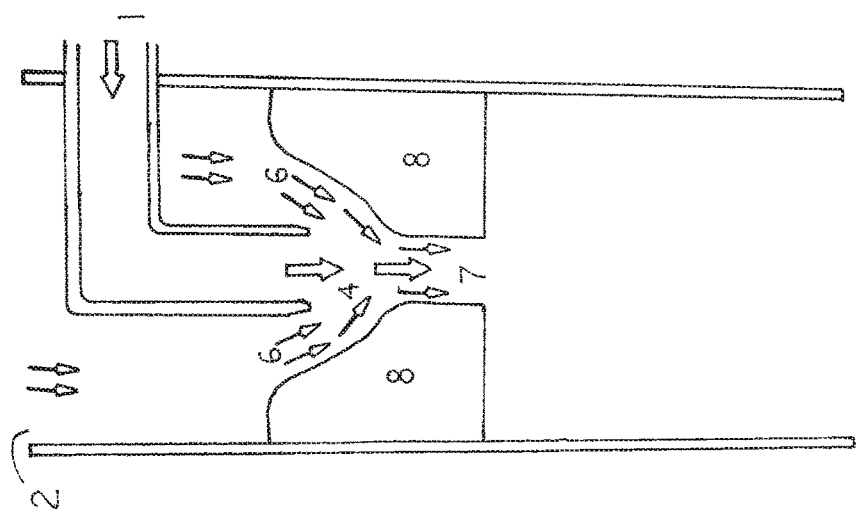
Figure 10B:
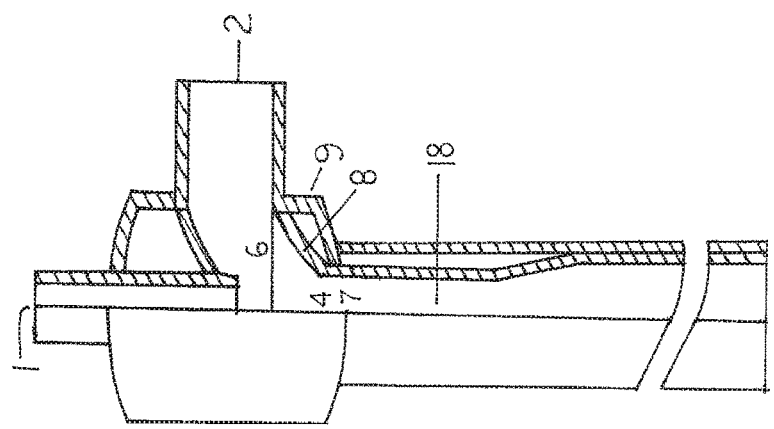

FIGS. 10a and 10b depict the direction of flow of solvent (by the broad arrows) and pollutant (by the narrow arrows) through the upper portion of the two versions of the homogenizer units.

FIG. 11a depicts a vertical, longitudinal section through a much simplified schematic of an homogenizer unit venturi. The venturi surface is smooth and largely featureless.

FIG. 11b depicts a similar section through an homogenizer unit venturi. The venturi surface has circular grooves and corresponding ridges. A single or multiple spiral grooves may also be applied to the venturi external surfaces.

FIG. 11c depicts a similar section through an homogenizer unit venturi. This example has vanes that are elevated above the otherwise smooth venturi surface. Additional vanes may be applied to the venturi surface and may not extend into the venturi throat or may extend the width of the venturi.

Figure 11E:
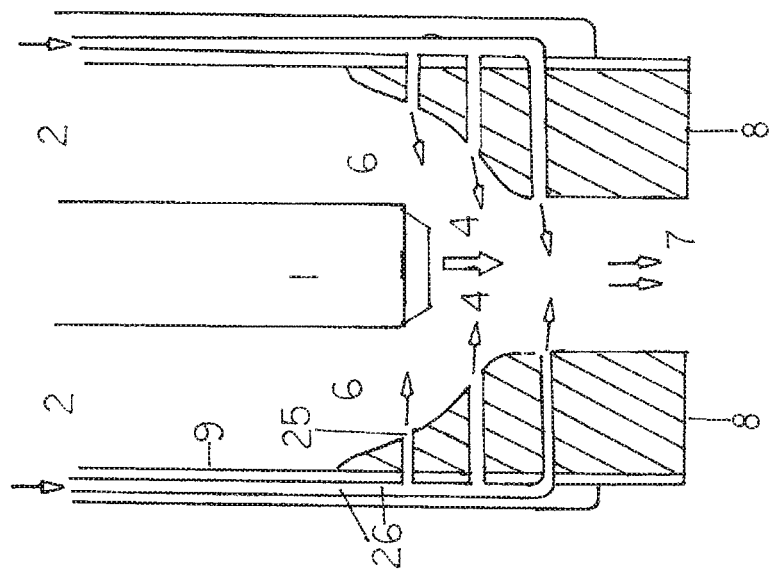
Figure 11D:
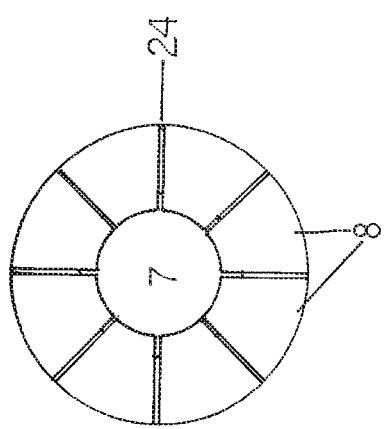

FIG. 11d depicts a planar view of an homogenizer unit venturi. This venturi has radially-oriented grooves. More grooves may be present in operational models and these grooves may or may not extend into the venturi throat to any degree, as desired.

FIG. 11e depicts a longitudinal, vertical section of an homogenizer unit. Only the water jet, 1, the venturi, 8, the port openings, 22, and the gas-liquid transfer tubes, 17. or lines are pictured in this schematic.

Figure 12A:
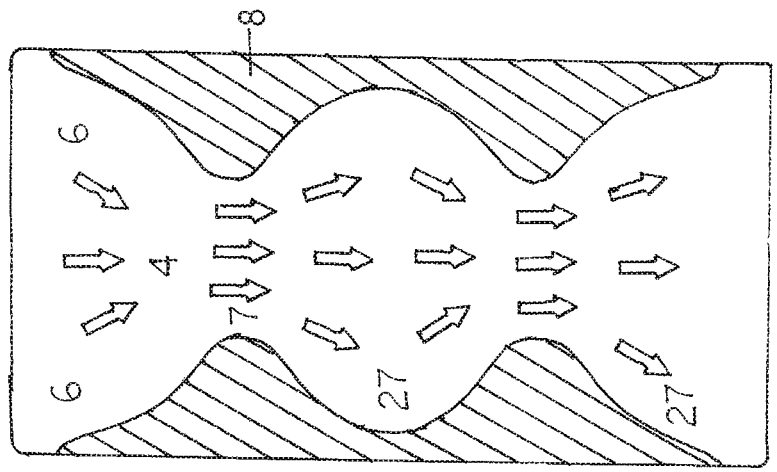

FIG. 12a depicts a longitudinal, vertical section through a portion of an homogenizer unit retention chamber. In this embodiment, a series of spherical, interconnected chambers allow for alternate expansion and contraction of the gas bubbles in the solvent stream. The arrows indicate flow pathways for the solvent-gas stream.

Figure 12D:
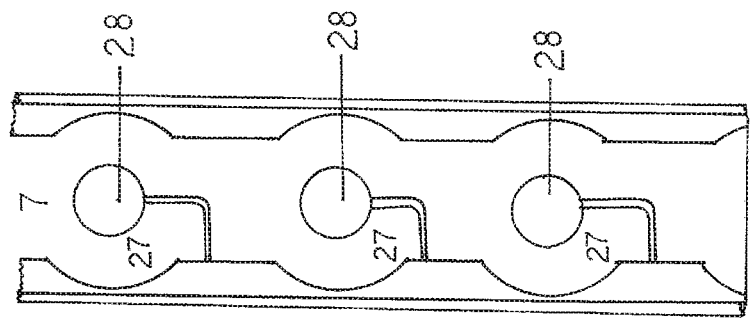
Figure 12C:
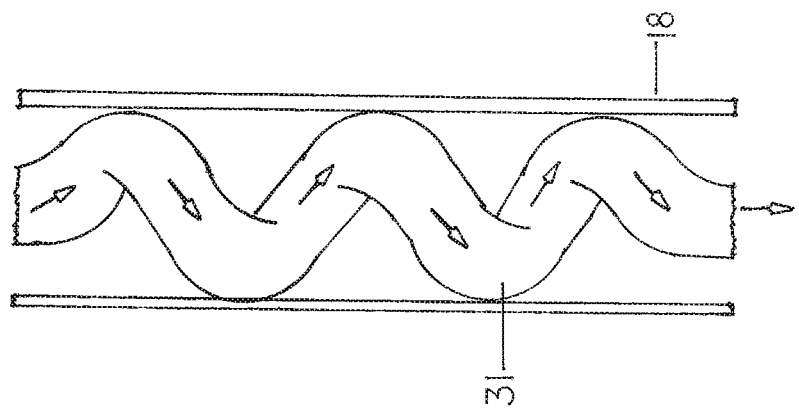
Figure 12B:
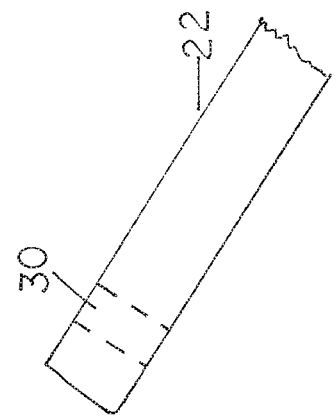
Figure 12B:
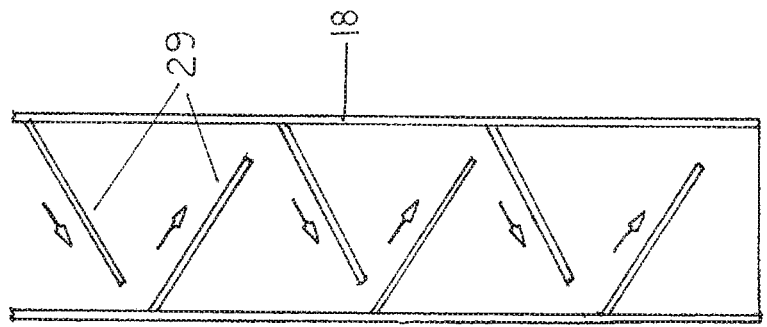

FIG. 12b depicts a longitudinal, vertical section through a portion of an homogenizer unit retention chamber. In this embodiment, a series of tilted or angled baffles are arranged in opposition so as to extend the flow pathway as indicated by the arrows. FIG. 12bb depicts a detail view of a baffle of FIG. 12b.

FIG. 12c depicts a longitudinal, vertical section through a portion of an homogenizer unit retention chamber. The spiral achieves a similar and extended pathway as does a series of baffles. The flow pathway is indicated by the arrows.

FIG. 12d depicts a longitudinal, vertical section through a portion of an homogenizer unit retention chamber. The spherical and interconnected chambers have a centrally mounted 'spoiler' bead or ball. This 'spoiler' results in a slower flow of liquid through the chambers and also creates a more tortuous pathway for the liquid. Some compression of gas bubbles will occur as they travel the circuit around each spoiler.

Figure 13C:
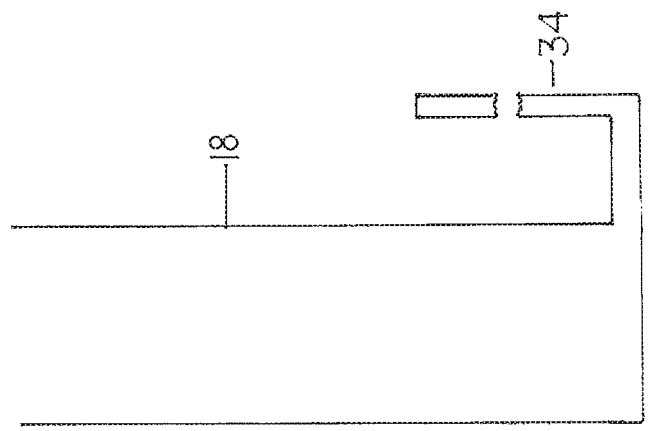
Figure 13B:
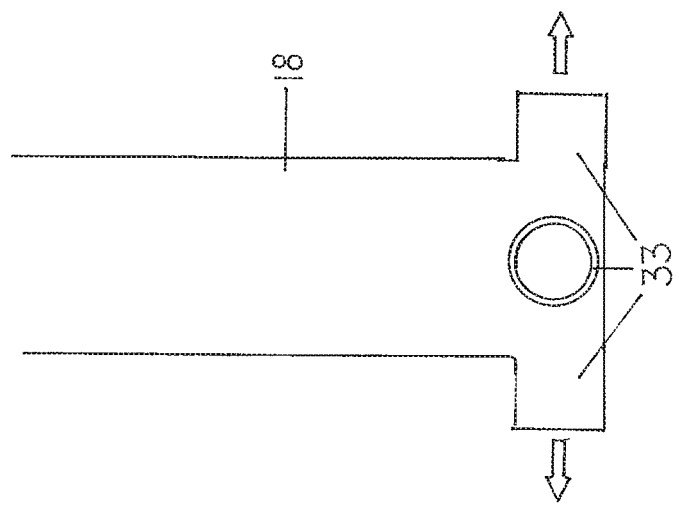
Figure 13A:
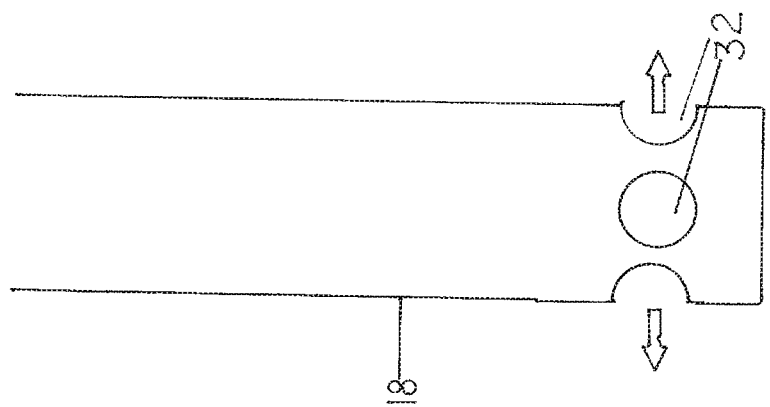

FIG. 13a depicts a lateral view of the exterior surface of an homogenizer unit retention chamber near its center and lower extreme. The ports are spaced equidistance apart so as to allow for uniform lateral discharge of the liquid into the receiving tank.

FIG. 13b depicts a similar lateral view of the homogenizer unit retention chamber at its center and lower extreme. In this embodiment, tubes extend laterally so as purge liquid further from the unit.

FIG. 13c depicts an embodiment to the extreme terminus of the homogenizer unit retention chamber. One or more discharge tubes extend a distance from the homogenizer unit retention chamber. At some distance from this same unit, the tube(s) turn upward, then laterally, thence downward to form a 'j-tube'. This ensures sediment or precipitated solids are largely undisturbed and may even discharge into a separate holding or equalization tank, thereby ensuring 'spent' reactant is not intermixed with 'fresh' or unused reactant.

Figure 14A:
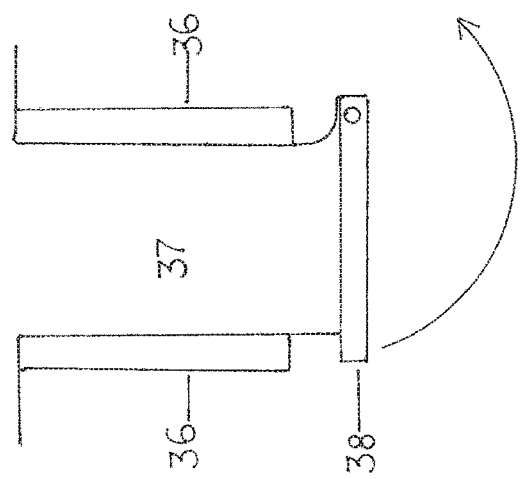
Figure 14:
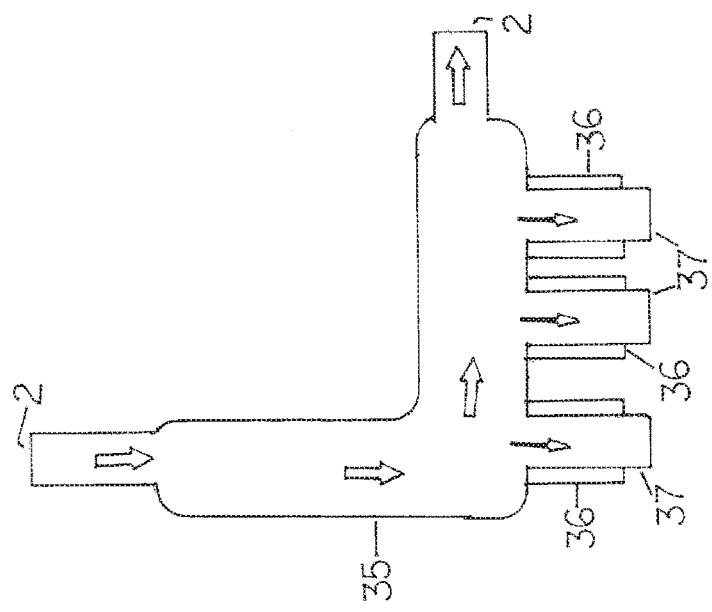

FIG. 14 depicts an 'L-shaped' chamber that allows for entry of the pollutant stream at the uppermost angle. The pollutant stream then traverses downward and then laterally to exit, 2, whence this stream is then directed to the homogenizer unit. FIG. 14a depicts a detail view of a shunt of FIG. 14.

Figure 15:
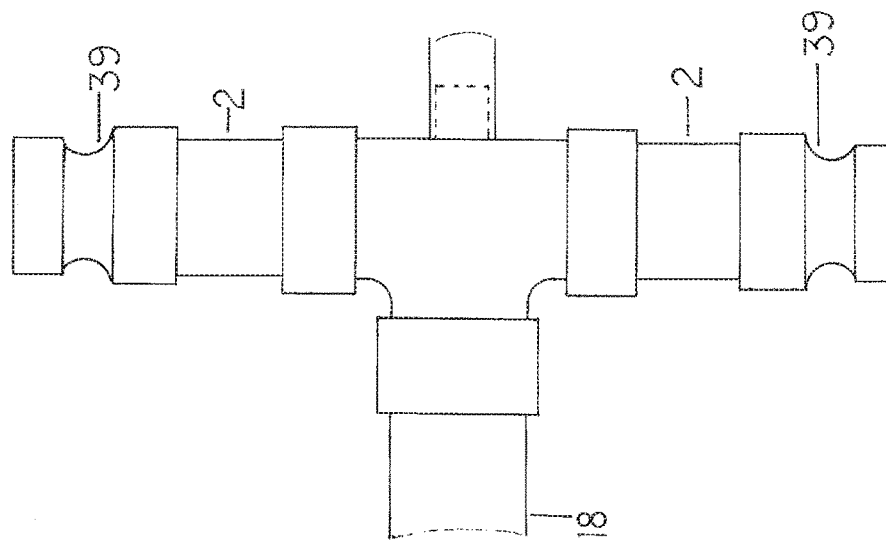
Figure 15A:
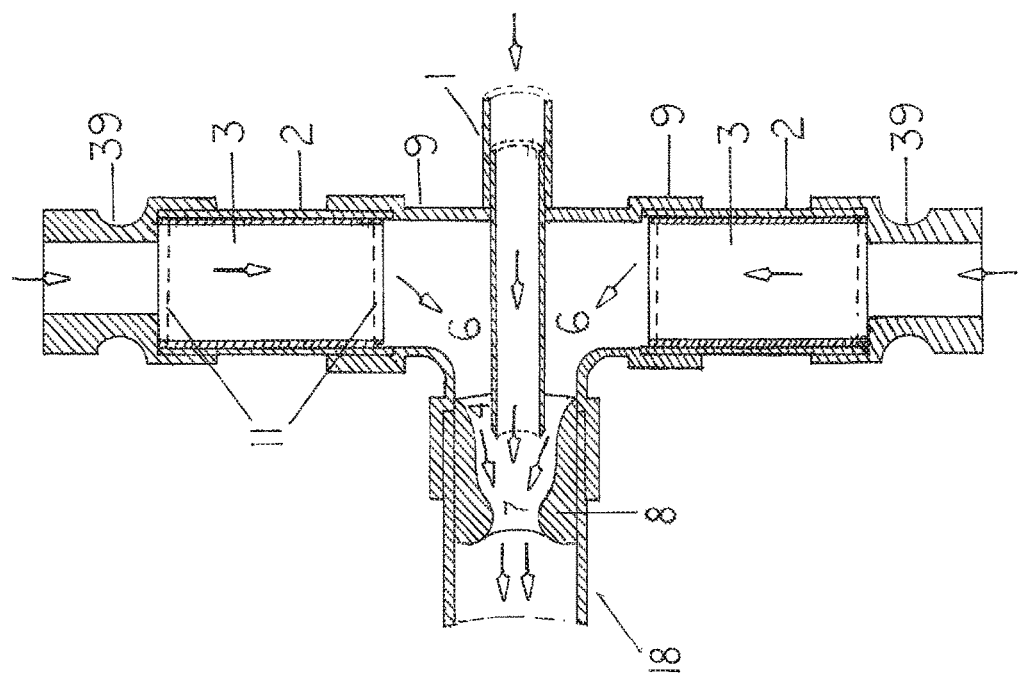

FIG. 15a depicts a vertical-central section through the same homogenizer unit. FIG. 15 depicts an exterior view of the homogenizer unit of FIG. 15a. The numbered components conform to the numbers of the same or similar components as depicted in FIG. 1a.

Figure 16B:
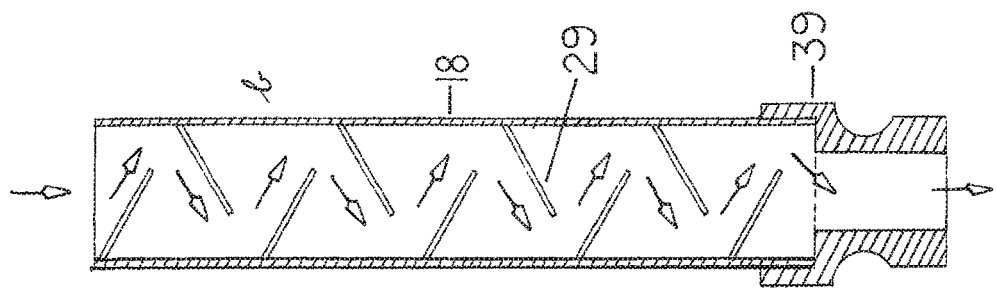
Figure 16A:
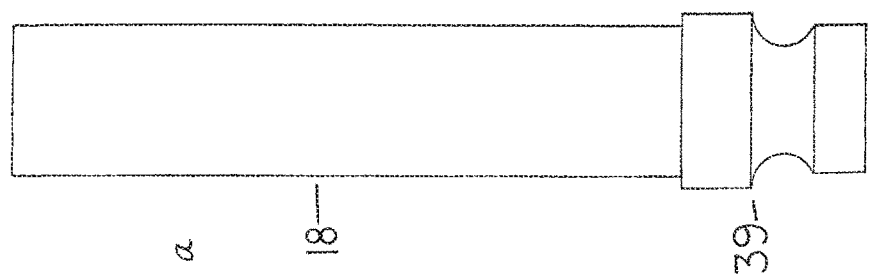

FIGS. 16a and 16b depict respectively the exterior and interior lateral view of the retention chamber-discharge tube of the homogenizer unit. The additional device at the lower terminus of the discharge portion of the tube is a CAM-LOK® fitting.

Figure 1A:
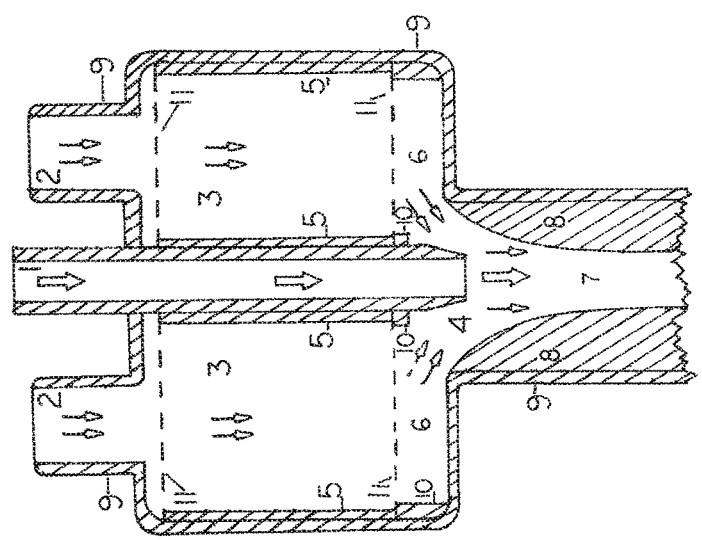
FIG. 1a is a central, longitudinal section of the homogenizer depicted in FIG. 1. The ante-mixing chamber, 3, is centrally perforated to allow for passage of the water/solvent jet, 1, into the mixing chamber, 4. The pollutants traverse downward through the ante-mix chamber, 3, and enter the mixing chamber, 4.
Figure 1:
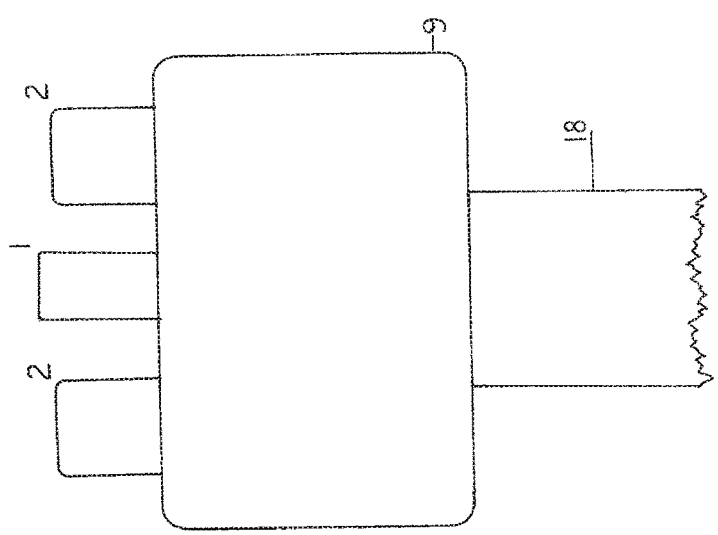
FIG. 1 is a lateral, external depiction of a homogenizer unit that is expanded in width to contain an ante-mix chamber FIG. 1a. The pollutant entry ports, 2 (carrying the target material-containing stream), have been positioned to the top of the homogenizer. They are spaced equally apart to allow for uniformity of pollutant entry.
Figure 17A:
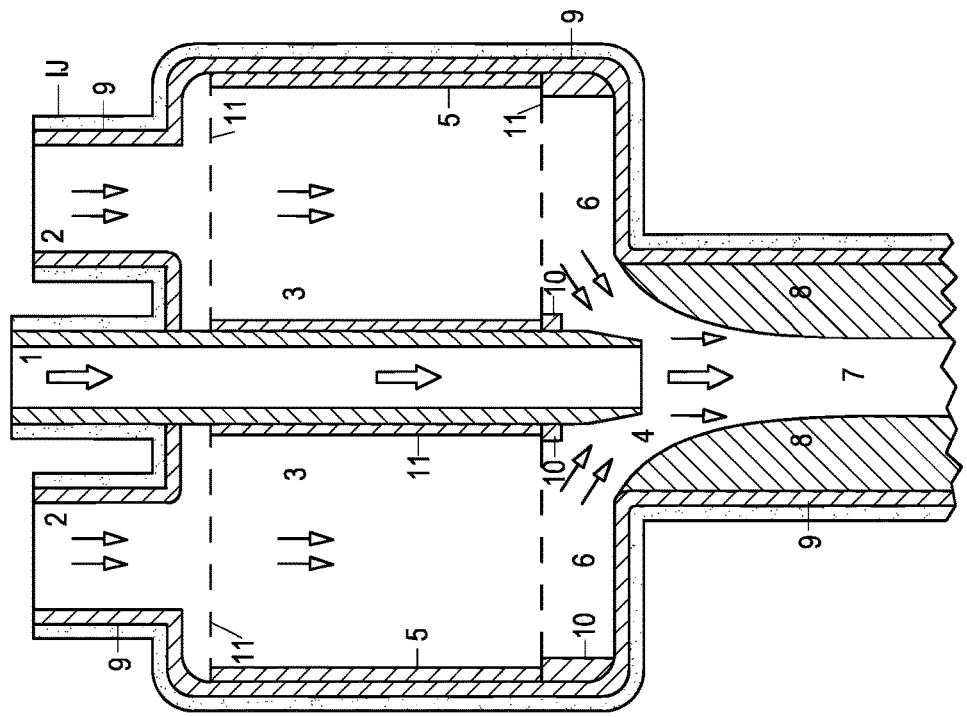
Figure 17:
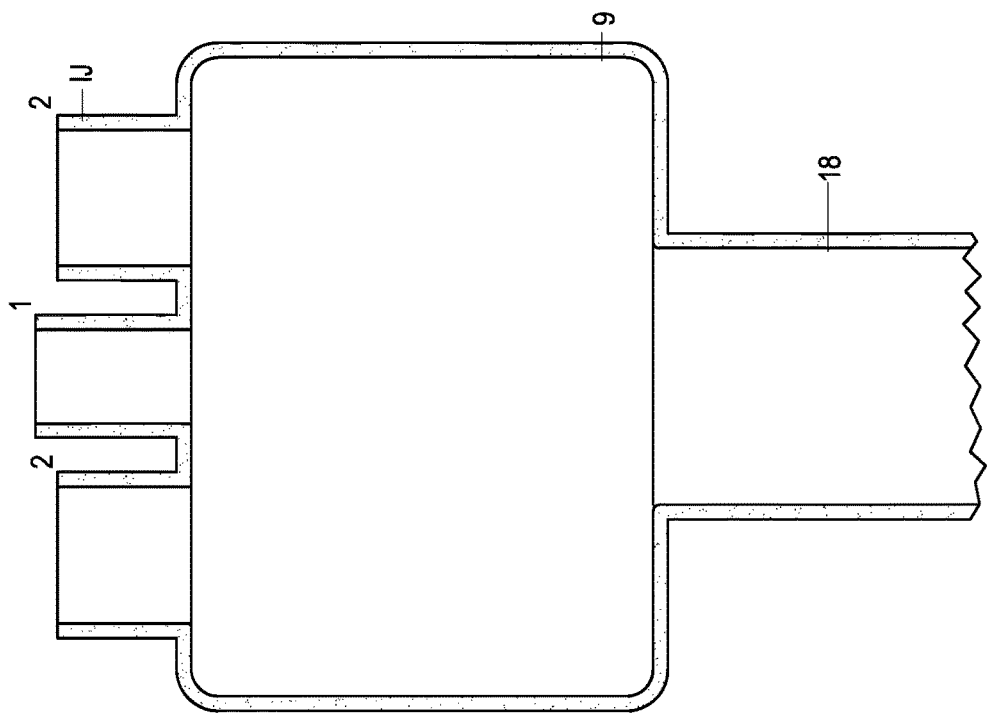

FIGS. 17 and 17a depict a PPH similar to that of FIGS. 1 and 1a, but including an insulative jacket.

Figure 18:
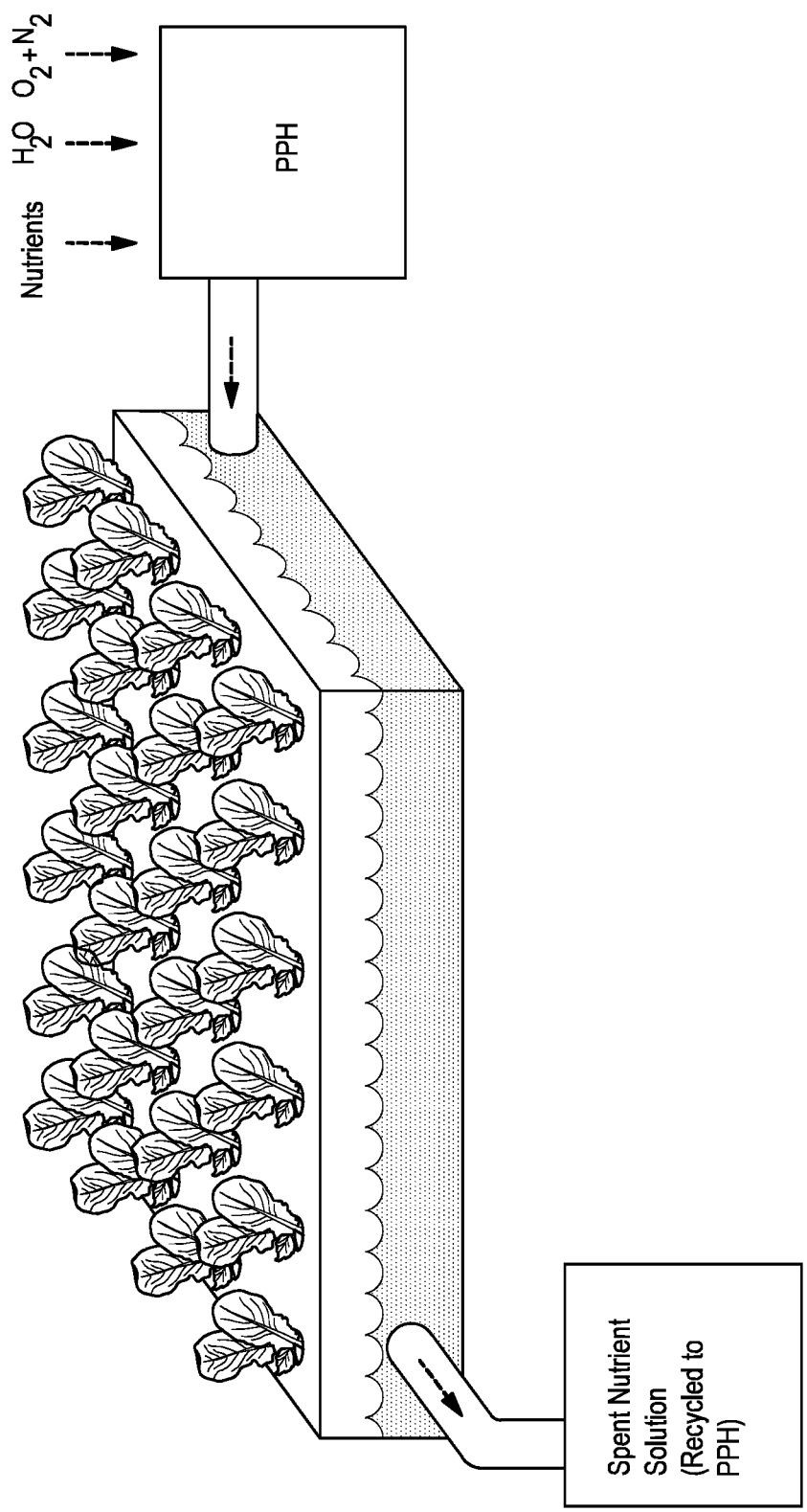

FIG. 18 is a schematic illustration of an exemplary hydroponics system.

Figure 19A:
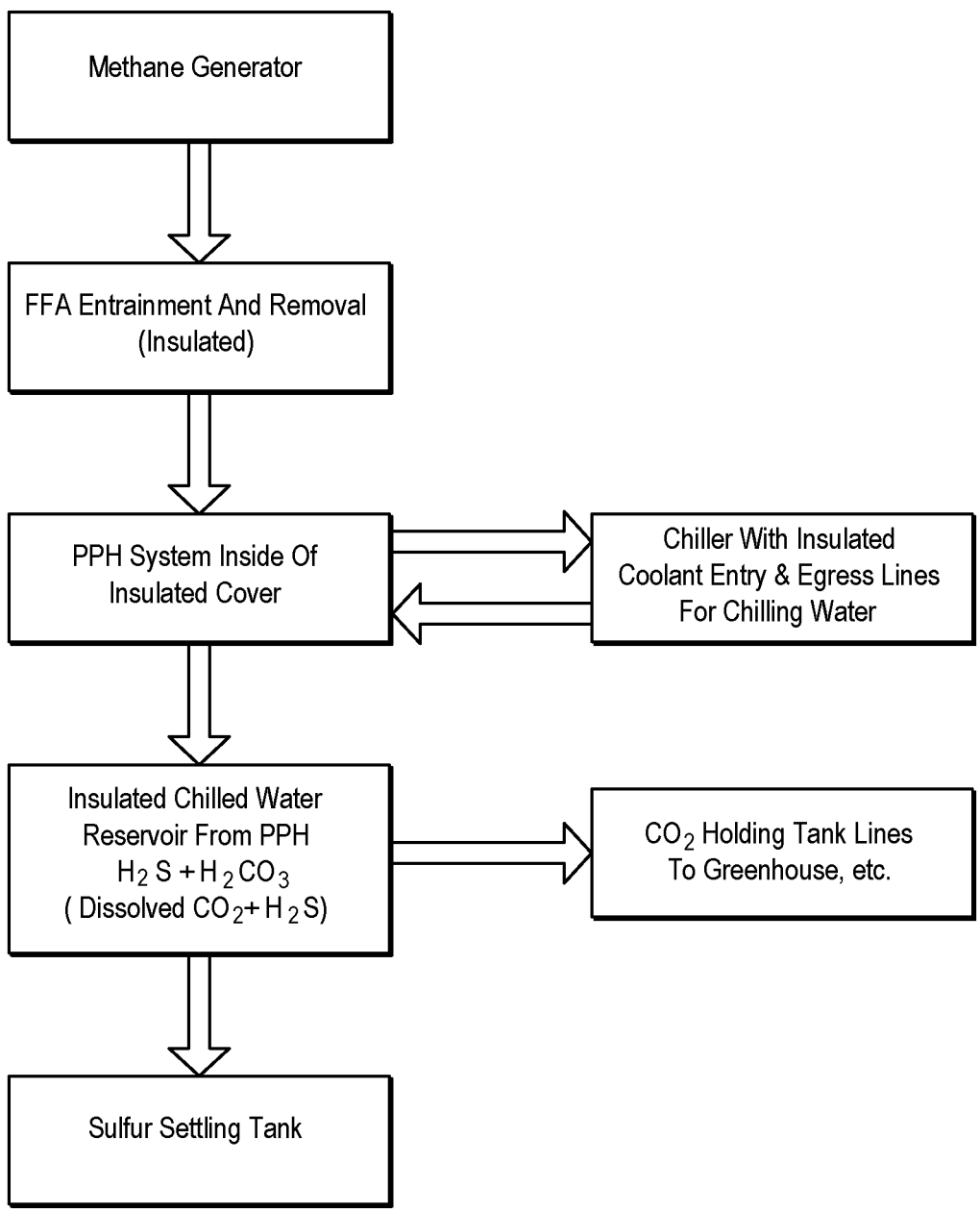

FIG. 19A is a flow chart describing a method and system using the PPH for purifying a raw methane stream.

Figure 19B:
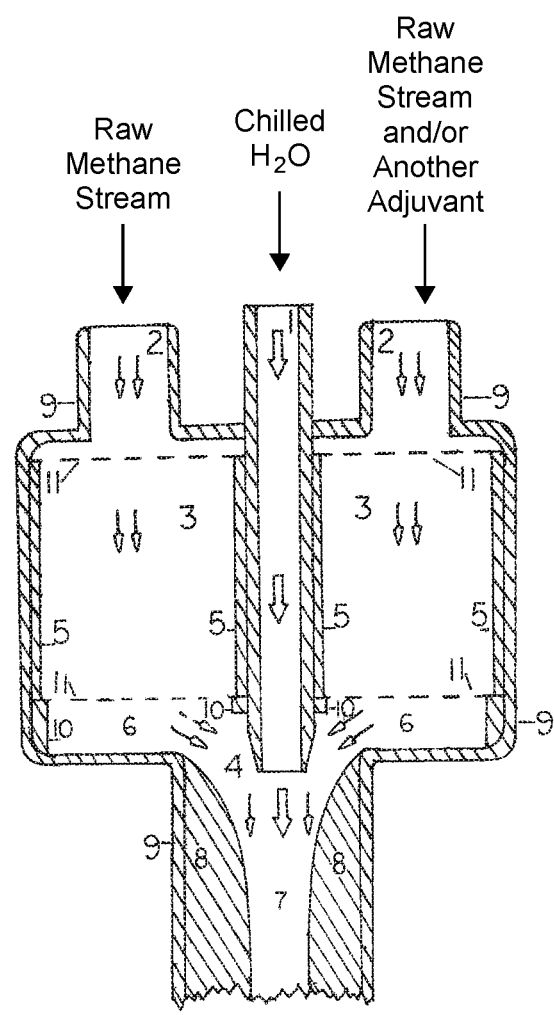

FIG. 19B is similar to FIG. 1a, showing exemplary inputs to a PPH system for purifying a raw methane stream.

DESCRIPTIONS OF THE PREFERRED EMBODIMENTS

I. Related to the Ante-Mix Chamber(s) or Conduit(s)

In external view, the ante-mix chamber housing portion of the homogenizer unit (FIG. 1 and FIG. 2) is enlarged as an embodiment to contain an ante-mix chamber as depicted. This somewhat flattened cylindrical housing (of narrower depth than width) is of adequate width to house the ante-mix chamber and the water jet or jets. Its upper surface is flat in profile and supports one or more pollution entry ports (FIG. 1a, 2 and FIG. 2a, 2) and their respective tubular fittings, a water jet tube or tubes (FIG. 1, 1 and FIG. 2, 1 and other figures), and, optionally one or more gas entry ports (FIG. 4, 16, 17).

The pollution entry ports (FIG. 1a, 2 and FIG. 2a, 2) may be circular or elliptic in outline and may penetrate the homogenizer unit housing either laterally or vertically as so deemed by required designs of an operating unit.

The expanded width version of an homogenizer unit is either mounted upon the homogenizer unit housing (FIG. 1, 1a) or is of the same diameter of the retention chamber housing (FIG. 2, 2a).

In internal view (FIGS. 1a & 2a), the modified homogenizer unit(s) contains the various integrated components. These include the water jet or jets (FIG. 1a, 1 or 2a, 1 & FIG. 8a-8d), the orifice or orifices (FIGS. 1, 1a, 1 & 2, 2a, 1 & FIG. 8a-8b) or entry port or ports (FIGS. 1, 2, 1a, 2 & 2, 2a, 2) for the pollutant stream(s), any bulkhead (FIG. 4, 16) and respective transfer line terminus (FIG. 4, 17) for gas or liquid entry, and any other mixing device.

The undefined space above the ante-mixing chamber (FIGS. 1a, 3 & 2a, 3) is termed the 'headspace'. It is within this region where any and all gas entry and preliminary mixing of pollutants and reactive gas(s) occurs prior to passing through the ante-mix chamber. One embodiment to the cylindrical homogenizer unit is the use of an active mixing device having rotating paddles on a shaft (FIGS. 4, 15 & 14) driven by an external electric motor (FIG. 4, 13).

The ante-mix chamber design embodiment (FIG. 1a, 3 & FIG. 2a, 3, and FIGS. 5 & 7a, 7b) fits within the homogenizer unit housing (FIG. 1a, 12, 2a, 12, FIG. 5, 12 & FIG. 7a & b, 12). This chamber is of a shape (dorso-ventrally flattened cylinder) that fits within engineering tolerances within the housing and presents the flattened, screened upper and bottom sides to the headspace and mixing chamber, respectively. This ante-mix chamber (FIGS. 1a, 3 & 2a, 3, FIGS. 5, & 7a, 7b) consists of a section of tubular material (plastic, ceramic, metal, etc.) and an upper and lower screen (FIGS. 1a, 11 & 2a, 11, FIGS. 5, 11 & 7a, 11 & 7b, 11). In one version of this chamber, a central, circular channel allows the water jet or jets (FIG. 1a, 1 & FIG. 5, 16) to pass vertically downward through the ante-mix chamber. This channel is also a section of tubing (FIG. 1a, 5 & FIG. 5, 16) of a diameter that allows for unimpeded passage of the water jet or jet's tube or tubes, respectively, through the ante-mix chamber. A screen support ring is located at the lower end of ante-mix chamber housing (FIG. 1a, 10). The bottom screen area nearest the water jet(s) is supported by another support ring that is integral to the jet (FIG. 1a, 10a).

The top and bottom screens (FIGS. 1a, 11 & 2a, 11 & FIG. 5, 11 & FIG. 7a, 7b, 11) rest upon these supports. In some instances, radial supports may or will be required, as well. Each screen is circular in outline and of a diameter that fits within and upon the ante-mix chamber supports (at the bottom) or housing (on the upper side as depicted in FIGS. 1a & 2a).

The screen embodiments (FIG. 8a-8d) are fabricated from a plastic material, series '300' stainless steel, or some other suitable material. The openings may be hexagonal (FIG. 6a), circular (FIG. 6b), square (FIG. 6c), diamond-shaped (FIG. 6d), or any other opening. No restrictions to the opening or perforation shapes are implied.

Various devices may be stationed within this ante-mix chamber (FIGS. 7a & 7b), including Bioballs® (FIG. 7a), baffles (FIG. 7b), spiral mixers, or other 'packings'. These may include, but are not restricted to: vertical or horizontal tubes, saddles, hollow and perforated objects of various types, matting, woven or spun fabrics, spiral devices, or any other device that causes the pathway to be of a tortuous nature for passing pollutants and gases. Any such packing materials may be included within embodiments of the homogenizer unit.

One embodiment is the water jet or jets (FIG. 8a-8d). Although simple in configuration, the jet has functions beyond that of adding water or an aqueous matrix to the mixing chamber. Each jet is advantageously directed at the venturi throat (FIGS. 1a, 1 and 2a, 1) and have a flow equivalent to the flow of water through the venturi. Should two or more jets be used, their combined flows must be equal to that of the single jet. Each jet terminus (FIG. 8a, 20) is advantageously perpendicular to its longitudinal axis and the surrounding taper (FIG. 8a, 21) is advantageously beveled so as to prevent spattering or side spray of the water or solvent. The distance from the jet terminus to the venturi throat is advantageously configured such that no impediment to flow of either the pollutant stream or solvent stream occurs (FIGS. 1a & 2a, FIGS. 9a, 4 and 9b, 4).

II. Descriptions of the Preferred Embodiments Related to the Venturi

Once the pollutant stream passes into the mixing chamber (FIG. 9a encircled region), water from the jets or another solvent containing various reactants come into contact with the pollutant stream (FIG. 10a, 10b). The pollutant stream and its respective flow direction is denoted by the thin arrows mixed stream while the water or solvent stream is denoted by the larger arrows. The mixed stream now enter the 'cone' of the venturi (FIG. 1a, 7 & FIG. 2a, 7, FIG. 10a, 7, FIGS. 11a & 11b, 7, & 10b, 7 where even closer contact and some chemical changes to some of the pollutants occur.

Various surface treatments of the venturi (FIG. 11a-11e) now have an effect upon this mixed stream. FIG. 11a, 7 depicts a venturi with a smooth surface. FIG. 11b, depicts a lateral view of a venturi that has vanes (FIG. 11b, 22) on the venturi surface and throat. These vanes channel (force) the mixed stream downward through the venturi cone into the venturi throat. Although the liquid is incompressible, the entrained gases start dissolving in the liquid as per Boyle's Gas Law. The spaces between the vanes narrow as they extend into and down the venturi throat. This exerts steadily-increasing pressure upon the gas or gases, thereby forcing more gas into solution. Any such surface modification may be employed within the homogenizer unit.

Other surface treatments include concentric ridges and grooves (FIG. 11c, 23) as an embodiment. Although the pressure does increase somewhat, they cause further mixing by creating turbulence and eddy currents in the liquid stream.

Radial grooves in the venturi surface are also an embodiment (FIG. 11d, 24) that also increases the pressure upon the entrained gas. Of concern is the tendency of grooves to become partially or completely plugged or blocked (blinded') by entrained particulates, thereby rendering the grooves to be ineffective and possibly hindering flow.

Another embodiment of the venturi is the insertion of a gas or liquid port(s) on the cone and throat (FIG. 11e, 25). This allows for the entry of oxidizers or a concentrated reactive liquid to come in intimate contact with the mixed gas-liquid stream. This area is a region of relatively high pressure upon the gas-liquid stream. This ensures contact of an oxidizer or other reactant with the entrained gas bubbles. The reactions at the gas-liquid interface of these bubbles results in very rapid and efficient anion substitution. Also, the collision effect is at its ultimate level as is the dominant-ion effect.

Should a gas or different gases be injected through these ports, the passage of gas or gases preferably is through individual transfer lines (FIG. 11e, 26) as depicted. Dividing a single transfer line by a manifold system at the venturi results in the less dense gas exiting only the uppermost port(s) instead of exiting all of the ports with equal flow volumes and rates. These transfer lines may all fit within a single larger tube so as to keep them grouped.

Injecting a single reactive solution or solutions through these ports is also an embodiment of the homogenizer unit.

III. Description of the Preferred Embodiments of the Retention Chamber

Modifications to the retention chamber (FIG. 9a, 18) increase the time the liquid-gas mixture is contained with the homogenizer unit. One such embodiment is the use of serial (interconnected) spherical chambers (FIG. 12a, 27) behaving as a series of venturis. Each such 'chamber' allows for a drop in pressure at the point of entry to the center of the chamber thereby allowing some portion of the entrained gas to expand in the liquid-gas mixture. As this liquid-gas mixture passes downward toward the now narrower bottom outlet of the chamber, the venturi effects are again in force and the gas bubbles decrease in size. This occurs within each chamber. Mixing is quite thorough and testing has proven the concept to be valid.

An embodiment of the above serial chambering includes 'spoilers' (FIG. 12d, 28) inserted centrally in the chambers and flow pathway. These 'spoilers' are single and solid beads, balls, or inverted cones mounted on a 'L-shaped' mount. These spoilers cause the flow pathway of the liquid-gas mixture to be interrupted somewhat while diverting this pathway laterally in all directions 'around' the spoiler. Eddy currents and further mixing are the primary results of having these spoilers in place. Each chamber therefore acts as an individual venturi.

Another embodiment to the homogenizer unit retention chamber is the use of baffles (FIG. 12b, 29) of any type (as previously listed for the ante-mix chamber) within the retention chamber. These perform in the same manner as in the ante-mixing chamber, but includes a liquid as well. The flow pathway is extended varying with the angle at which the baffles are mounted. A 'weep' hole (FIG. 12bb, 30-detail) is drilled through the upper end of each baffle so as to prevent 'free' gas buildup in the 'angle' between the baffle and retention chamber housing.

Another embodiment to homogenizer retention chamber is the use of a spiral device (FIG. 12c, 31) to both mix the liquid-gas mixture even more thoroughly and to extend the reaction time(s) due to the increased length of the spiral as compared to the straight profile of the retention chamber. As with the other embodiments, baffles or other detention devices may be placed within the spiral or spirals, gas ports may be applied, and a tight or 'close' coiling of the flexible spiral may be used as against having an 'open' or loose spiral.

IV. Description of the Preferred Embodiments of the Discharge Tube(s)

Discharge tube modifications may be included within embodiments of the homogenizer unit. Ports of various sizes and positioning are located at the lower terminus of the retention chamber (FIG. 13a, 32). The intent of these ports is to direct the flow of the liquid-gas mixture outward into the receiving vessel so as not to unduly disturb any sediment or precipitate(s) that lie on the vessel bottom interior. These ports may have simple extensions (FIG. 13b, 33) or secondary discharge tubes that force the liquid-gas mixture to flow laterally (or in some other preferred direction).

One embodiment of the discharge tube(s) is the use of extensions of this/these tube. In one application, the discharge tube may empty into a second reservoir than the one from which the reactive solution was derived. In another embodiment, the tube may extend laterally, thence project upward to form a 'j-tube' (FIG. 13c, 34). This may empty into the reservoir from which the reactive solution was drawn or into a separate reservoir.

If a stoichiometric balance is intended between a reactive solution and the entrained or dissolved gas(es), then recirculation within a closed loop would allow for such 'balancing' to occur in batch form. If the intent is to have a 'bleed and feed' sequence, then transferring the reactive solution from one tank, thence through the homogenizer unit (with its various embodiments) and into another reservoir would be necessary.

Should particulates having magnetic properties be part of the pollutant stream and it is deemed necessary to remove them for some reason (erosion of the pump impellers, etc.) then electro-magnet(s) and their respective chamber that is located upstream from the homogenizer unit can serve as a collection-shunting system. This embodiment (FIG. 14, 35) is an 'L-shaped' chamber that allows for entry (FIG. 14, 2) of the pollutant stream at the uppermost angle. The pollutant stream then traverse downward and then laterally to exit, 2, whence this stream is then directed to the homogenizer unit.

A series of shunts (FIG. 14, 37) encircled by electro-magnets (FIG. 14, 36) with hinged caps (FIG. 14a, detail 38) allows for magnetic particles to collect and then be removed as they reach a level at which they must be removed.

Prelude: Hazardous and even deadly conditions frequently exist in and around grain silos and grain transfer devices that load and offload grain from ships holds, trucks, and rail cars, metal dust generators, sugar mills, saw mills and woodworking shops, cotton gins, and solid propellant manufacturers, to list a few industries.

FIG. 15 depicts the exterior lateral view of this version of the homogenizer unit. The housing (9) is TEE-shaped as depicted. The entry port for water (1) is mounted vertically while the inlet ports (2) are lateral. Such ports do not have to be mounted perpendicular to the unit axis, but may be at any angle or even include further extensions with 'ells' that are mounted at any angle.

A short section of the retention chamber (18) is depicted. The terminus is not included in this drawing.

FIG. 15a depicts a vertical section through this version of the homogenizer unit. All numbered components conform to the same numbers in FIG. 1a. Flow pathways and directions are indicated by the arrows. The water inlet port and jet (1) project downward as in other similar units. The lateral ports (2) serve the same purposes as in other homogenizer units as do the ante-mix chamber canisters (3). Other than having the lateral extensions of these ports, each such port has a fitting or device at its outer extremity called a CAM-LOK® (39).

FIG. 16a depicts a lateral view of the retention chamber (18) and discharge tube with a CAM-LOK® (39) fitting at its terminus. All other numbers conform to the same numbers of a similar device or embodiment as seen in FIGS. 1a, 2a, 3, 9a, 9b, and other figures.

FIG. 16b depicts a vertical section through the retention chamber (18), discharge tube (32, 33, 34), and CAM-LOK® (39). Internal baffles (29) having an angled orientation are depicted but should not be considered as the sole modification or embodiment to this portion of the homogenizer. All other previously listed modifications are applicable in all manners.

The CAM-LOK® fittings allows for homogenizer units to be placed remotely from the ancillary reactant and spent solution tank or tanks and also ensures gas-tight junctions where and when required (as in explosion proof environments). This also allows a battery of homogenizers to be placed so as to take advantage of a single and larger inlet line for pollutant stream input and treated stream output. Although the solvent stream appears to be permanently attached to the homogenizer unit, a similar CAM-LOK® can be installed at some point forward on the water or solvent inlet port so as to allow the homogenizer unit to be removed and/or replaced as deemed necessary.

EXAMPLE 1

The homogenizer unit and ancillary embodiments lends itself to the safe and effective removal of both hazardous and non-hazardous particulates from the atmosphere and to their entrainment into an aqueous matrix, thereby rendering such particulates harmless and in a contained situation that is inherently safe.

Passing a large volume of dust-laden or contaminated air through an homogenizer unit (that is properly grounded to prevent static electricity buildup and subsequent discharge) forces the entrained particulates to become 'wetted' simply by forced contact with the homogenizer embodiments. If deemed necessary and more efficacious than water, a suitable surfactant or other agent that enhances wetting and surface tension reduction will be introduced into the water. Contaminated air is depured (=purified) to a very high degree (that approaches complete removal of particulates), thereby releasing cooled, humidified, particulate-free air back into the atmosphere from which the particulates were originally derived.

In practice, the cooler, clean air is much less subject to static electricity build-up and discharge thereby significantly enhancing the safety levels in such situations. In addition to the increase in safety from the static charge build-up, the air is cleansed of allergens such as vermin hair, feces, and urine, mold spores, bacterial cells, pollens, plant fibrils, and other similar products as well as metal dust, dirt, smoke, saw dust, VOCs, acid vapors, oil vapors and smoke, and other products of manufacturing.

EXAMPLE 2

Serial placement of homogenizer units including the aforementioned ancillary embodiments may or will result in the segregation of a certain entrained gas or gases, pollutant or pollutants from internal combustion engines, furnaces other than electric units, smelter and metal crafting discharges, or other combustion sources while allowing that same gas or gases to pass into serially-arranged reaction vessels or vessels in parallel or having a variety of configuration or configurations. In this application or these applications, removal of a certain pollutant or pollutants may be adequate to allow the gas passing into the terminal reaction vessel or homogenizer unit or units to be depured (=purified) so as to render that gas or gases suitable to be containerized for some means of disposition.

For example, a mixed stream of pollutants containing carbon dioxide ($CO_2$), carbon monoxide (CO), particulates (PMs), ammonium ion ($NH_3$), nitrogen oxides (NOx), sulfur oxides (SOx), and volatile organic compounds (VOCs), plus non-metals, heavy metals, and metalloids is to be treated to render the stream harmless (by definition of law or code).

When this stream is passed through a properly-designed (having the claimed embodiments and devices) homogenizer unit, the stream will be both physically and chemically 'scrubbed' so as to remove the particulates (of all dimensions of concern), the SOx and NOx will be converted by oxidation and hydration to form their respective sulfurous and sulfuric acids and nitrous and nitric acids. In many instances, the heavy metals and metalloids will dissolve in this acidic solution.

Most or all of the VOCs will either rise to the surface of the acid mixture or adhere to the vessel walls where it may be further treated by solvation (being miscible in a suitable solvent) or biodegradation after solvation.

The acidic solution in the foremost homogenizer unit or units results in the purging of both carbon dioxide and carbon monoxide, rather than converting these gases to a solid precipitate. Oxidation of the carbon monoxide by reacting with ozone or hydrogen peroxide converts this gas to carbon dioxide. The singular gas, the 'original' carbon dioxide as well as the carbon dioxide formed by oxidation of the carbon monoxide may now be 'scrubbed' via an aqueous means (having undergone a substitution reaction with the anion of a suitable anion donor to form a solid carbonate) and dried prior to containerization or being converted to a solid carbonate.

The acidic solution (from the first homogenizer unit in the series) containing the particulates can now be filtered or passed over a magnetic drum separator if any particulates are magnetic so as to segregate these particulates for further chemical substitution and disposition. All rinse solutions and the acidic solutions containing the metalloids and metals in solution can now be recycled if too dilute to cause saturation of the acidic solvent allow for recovery of the metals and metalloids or be treated by known methods so as to selectively or collectively concentrate these entities.

A variety of chemical and/or physico-chemical reactions may or do occur during the mixing phase or phases (provided the proper solvent is in usage) while the gas-gas, gas-liquid, liquid-liquid, liquid-particulate, or gas-liquid particulate streams pass through the homogenizer unit.

These reactions are enhanced or accelerated due to the mixing and intimate contact under pressure of the reactants within the homogenizer unit or units in addition to the pressure upon the gas or gases as they pass through the venturi or venturis in the homogenizer unit or units interior or interiors. The pressure increase results from an ever-decreasing diameter of the venturi ogive and the vanes, grooves, or texturing of the surface or surfaces of the venturi or venturis.

The primary principles applying to the chemical reactions are:

Note: Certain and common chemical reactions occur within any chamber or all of the chambers in the pre-mix region or regions or within any homogenizer unit or all of the homogenizer units.

One such common and well-known reaction is 'substitution' wherein one atom or a specific ion or molecule can replace another atom or specific ion or molecule from the structure of another molecule or other molecules.

For example: Iron oxide can be converted to iron chloride by adding hydrochloric acid to either dry iron oxide particles or to an aqueous slurry of iron oxide and water. Upon substituting a chlorine atom or several such atoms for the oxygen atom or atoms within the iron oxide molecule, iron chloride is generated. The oxygen that was bonded to the iron then bonds with some or all of the hydrogen atoms from the hydrochloric acid to yield water. As with all reactions of this type, varying amounts of heat is generated. The addition of acid to dry iron oxide particles may result in the generation of steam and hydrogen chloride as a vapor, thus presenting some hazards performing this reaction.

Domination Effect

Other chemical reactions occur because of an overwhelming or disproportionate quantity of both cations and anions are present in a liquid or gaseous mixture or in a liquid-gas solution. The overwhelming of certain or specific reactions by the dominant ions can result in the purging of certain compounds from a substrate or substrates. This reaction or effect 'recharges' the active substrate to allow for some type of absorption or adsorption to occur on or within the substrate that allows for continuous recycling of the substrate while yielding a desired product or products.

Examples of some of these applications and examples are as follows: A natural or synthetic substrate (molecular sieve) has the ability to absorb selected compounds from an aqueous stream, thereby changing this liquid to meet some desired specification or specifications. Continuous absorption and adsorption of these selected compounds from the liquid eventually results in the substrate becoming saturated with the selected molecules and no longer has the ability to retain them. This 'loading' affects the ability of this molecular sieve to retain or release undesired compounds into the liquid.

Regeneration of this desired substrate occurs when a saturated saline solution is forced into and flows through the substrate or molecular sieve. The absorbed compounds are then desorbed and pass into a liquid purging stream for discharge. The saline solution was so 'dominant' or overwhelming relative to its ability to enact substitutions that reactions occurred that normally would not occur on or within these substrates in more dilute solutions. This 'Dominant Ion Effect' is commonly used in water 'softening'.

SPECIAL NOTE: The following examples are not to be misconstrued as being restrictive in intent or use to the homogenizer invention or its embodiments. Any and all chemical, physico-chemical, and physical reactions that occur within the homogenizer unit are claimed as being relevant to the homogenizer invention.

Collision Effects

Although atoms do not actually collide with one another due to Van der Wall Forces*, bonding between ions does occur. In simplistic terms, a single 'collision' between a negative ion and a positive ion should or would yield an ion-pair. If one calculates the number of such negative or positive ions that can be made available during dissolution of an ionic salt in a suitable solvent, one can also calculate the number of oppositely-charged ions that will be available and required to balance the reaction or reactions to yield a balance of ion-pairs. In this manner, one could also calculate the number of such pairings or collisions that can possibly occur to bring about that same balance.

In simplest applications, a single negative ion can only collide with a single positive ion to yield an ion-pair. Two pairs of each separately charged ions will yield two ion-pairs while three negative ions and three negative ions of equal or near-equal charges will yield three ion-pairs. The numbers can be further calculated to an almost unlimited extent, so the prior example is suitable to offer an explanation of 'collision effect'.

*These 'forces' allow oppositely charged ions or particles to form bonds that allow atoms to stay at specified distances from one another due to both repulsion and attraction. Ions or particles with opposite charges, commonly called negative or positive charges, join or bond together to form an ion-pair and form charge-balanced solids (crystals) when solidified. Ions with like charges generally repel one another, but the distances between repulsed ions is limited to very short distances. Thus, a solution or solid would not have all of the negative ions in one region and all of the positive ions in another region. Rather, they tend to form ion pairs if their respective numbers or charges are balanced.

Surface Area Relative to Bubble Diameter and Volume

Relative surface area decreases as an entity increases in both volume and diameter and increases as an entity decreases in both volume and diameter. These conditions allow the homogenizer unit to function far more effectively than does simply passing a gas or through a tube or tubes and thence into a reservoir of a liquid by forcing gas bubbles to some depth in that liquid and the bubbles allowing them to simply rise to the surface of that liquid. In practical terms, this process is referred to as sparging'.

In an opposite manner, a gas or gases entering into the homogenizer unit or units is/are forced under pressure to some depth within a liquid. These bubbles become very small as a result of external pressure or pressures from both the diameter of the venturi or venturis and also the depth of the liquid upon them (pressure varies with the depth of the liquid, increasing as the bubble is forced downward into the solution and decreasing as the bubble ascends the liquid column). These bubbles are also subjected to agitation, thereby actively exposing all or most of their external surfaces to the reactive solvent or to reactive substances in that solvent. In this manner, dissolved or mixed gas or gases, liquid or liquids, or particulates within the pollutant gas bubbles are continually exposed multiple times to a reactant or solvent, thereby reducing the concentration or concentrations of the respective pollutants with the gas-liquid-particulate stream to a lesser concentration.

The following example presents this phenomenon in a graphic manner.

| Bubble diameter in millimeters (mm) | Surface area of sphere in mm² | Volume of sphere in mm³ | Ratio of surface area to volume |
|---|---|---|---|
| 1 | 3.1416 | 0.5236 | 6.000/1 |
| 2 | 12.5664 | 0.41888 | 3.000/1 |
| 5 | 78.5400 | 65.4500 | 1.200/1 |
| 10 | 314.1600 | 523.600 | 0.600/1 |
| 20 | 1,256.6400 | 4,188.800 | 0.300/1 |
| 50 | 7,854.00 | 65,450.00 | 0.120/1 |

Pressure Effects Upon Gas Dissolution in Liquids

Boyle's Law states: "At a constant temperature the volume of a given quantity of any gas varies inversely as the pressure to which the gas is subjected. For a perfect gas, changing from pressure, p and volume v to pressure p' and volume v' without change of temperature, pv=p'v'."

In a practical sense, this means that as the volume of an elastic vessel (=bubble) containing a gas decreases or increases due to pressure (=depth of the liquid), the ratio of gas to volume remains constant.

Should the gas volume decrease in proportion due to the gas simply being absorbed by the liquid or by reacting with an ion in that same liquid, the proportion of that same gas within that same bubble changes to a lesser percentage thereby reducing the volume of the bubble even more.

Reducing the bubble size results in a significant and relative surface area increase. This results in greater gas pressure on the surface film of that bubble in the liquid matrix. Gas will then dissolve into the liquid if such a gas is soluble to any degree in that same liquid. Once dissolved in the liquid, the gas is free to react with any suitable and available ion to form an ion-pair. This ion-pair may be quite soluble and remain in the liquid or relatively insoluble in the liquid and precipitate as a solid (such as a carbonate), although the reactions are not limited to these example or the parallel examples.

Potential Compounds that can be Formed within the Homogenizer Unit(s)

Depicting the resultant compounds of many substitution reactions is readily achieved using a chart based on the solubility or insolubility of selected elements and ammonia in water or acid (Y-AXIS of CHART 1 or left-hand column). All of the six-hundred seventy-eight (678) compounds marked with an upper case 'W' or 'A' in the same space are soluble in either water or acid, respectively. Those compounds marked with a lower case 'w' are weakly soluble in water, while those compounds marked with an upper case 'D' or 'I' either 'decompose in water or are insoluble in water, respectively.

The header bar, or top X-Axis of the Chart, lists the anions that contribute to the formation of the compounds listed in each row or space on that same chart. As noted, these anions include the halogens, various non-metals, and a variety of mineral and organic acids.

No radioactive elements or rare-earth element compounds are presented on the chart. This does not imply that chemical reactions or substitutions do not apply, rather, the radioactive compounds require special licensing and handling while the rare-earth elements have properties that require specific techniques related to their forming compounds.

Other parallel anionic or cationic reactions that fall within the above or similar reactions also apply even though they do not appear on the chart. The compounds presented on the chart are examples of the various cationic-anionic reactions and the resultant compounds that can be achieved as a result of application of the homogenizer unit.

EXAMPLE 3

Embodiments to the homogenizer unit, comprising:

a magnetic particulate removal device stationed in line with the homogenizer conduit, an ante-mixing chamber embodiment having one or more 'packings' that is contained within the homogenizer unit, a jet or battery of similar jets, each having the ability to conduct a single solvent or any combination of solvents to the venturi cone within the homogenizer unit, a venturi within the homogenizer unit, having a variety of embodiments relating to its surface treatments that may or will enhance the reactions between the solvent or solvents and the targeted pollutants, a detention chamber embodiment that is a continuous conduit with the homogenizer unit. This chamber may have a variety of internal configurations or devices that further enhance reactions between the reactant(s) and the targeted pollutants, a discharge tube or tubes or other devices as embodiments at the lower terminus of the retention chamber that control or direct the outflow of the reactant liquid and entrained matter to a specified location within the reservoir upon which the homogenizer unit is mounted or to some remote reservoir.

EXAMPLE 4

An air-purifying device utilizing the homogenizer unit and correlated embodiments in addition to an appropriate solvent and/or surfactant to remove and isolate airborne allergens, pathogenic and non-pathogenic microbes and other microscopic life forms, amorphous particulates, morphous particles, radon, steam, flammable and non-flammable vapors, fumes, dust, dirt, odors, hair, dandruff, or any mixture of the aforementioned entities. The prior list is a much-abridged list and should not be considered restrictive in any manner.

Air cleansing is achieved in a fashion similar to the applications in Example 1, but may not require any solvent but water that contains soap, a detergent, a surfactant, or other agent that reduces surface tension and increase hydrophilicity of the targeted pollutants.

The discharged air may be returned to the point of origin or discharged to the atmosphere while the solvent and the entrained entities can be disposed of via the common waste sewer (where allowed).

Methane Generation

Carbon combustion generates a variety of pollutants, among them carbon monoxide (CO) and its completely oxidized form, carbon dioxide ($CO_2$).

Both gases can pass through the PPH following pretreatment to remove PMs, VOCs, NOx, SOx, ammonia, and metal vapors. At this stage, both gases are relatively pure even though they occur in a mixed gas form. This aspect may be of benefit should a need arise to recycle the carbon monoxide as a secondary fuel at large electrical generation facilities, whether gas, oil, or coal-fueled or at co-generation plants.

Many coal-fired plants release thousands or millions of tons of both gases to the atmosphere in a largely uncontrolled manner. Obviously, this pollution stream contains a variety of other pollutants and, as such are under scrutiny from the general public as well as from local environmental regulators.

Generating a highly-purified mixture of CO and $CO_2$ via the PPH allows for the ready conversion of the CO to methane (under the proper conditions!). Instead of converting the $CO_2$ to some carbonate species and thence converting the CO to $CO_2$ as can be achieved with the homogenizer, leaving these gases in their mixed form prevents ignition of CO due to the lack of adequate oxygen. The $CO_2$ serves as a 'blanket' to prevent the ignition of the CO and behaves as an inert gas in the following process. Any excess $CO_2$ can be converted to a carbonate, thereby eliminating the storage of this gas in a pressurized vessel.

In this instance, the remaining carbon monoxide (CO) may be passed into a pressurized chamber with hydrogen ($H_2$) and then through a platinum, nickel, or cobalt sponge or fine screen that is heated. This yields methane ($CH_4$) and water ($H_2O$) as well as some heat and residual carbon dioxide. This reaction is depicted in a symbolic fashion below:

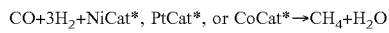

$$CO+3H_2+NiCat^*, PtCat^*, \text{ or } CoCat^* \rightarrow CH_4+H_2O$$

(*=nickel, platinum, or cobalt catalyst)

The heat will be absorbed into the water that forms, thereby preventing the overheating of the system. This water can be re-circulated or decanted for other uses, while the $CO_2$—$CH_4$ gas mixture passes through the homogenizer. A carbonate is formed from the $CO_2$ reaction with any alkaline hydroxide in the aqueous solution while $CH_4$ is discharged to the refrigerated dryer system. This $CH_4$ can now be returned to the burners to serve as an auxiliary fuel or can be sold as a precursor chemical to the plastics industry.

The hydrogen gas can be readily derived by electrolysis. In this manner, the oxygen can be sent to the ozone generator system or to the furnace to serve as the oxidizer, or to the equalization tank(s) where oxidation of certain metal species will enhance metal recovery.

Airborne Particulate Matter (PM) Containment

The deleterious effects of airborne particulate matter (PM) can be allayed via the application of the Polyphasic Pressurized Homogenizer (PPH or homogenizer).

Such PMs result from the combustion of many flammable products, ore crushing and dressing, construction, wood finishing, metal casting or smelting and finishing, and field crop rearing and harvesting.

Each phase of many of the above activities yields airborne PMs that pollute the atmosphere and/or environment in some manner.

In many instances, industrial PMs are conducted to a chamber or chambers that allow the contaminated air to pass through specially designed bags. Such units are commonly called 'baghouses'. Their efficient operation is fraught with problems, not the least of which is poor efficiency as the bag's inner surfaces become plugged, or 'blinded', with PMs. Air flow largely ceases through these bags, operations either cease or contaminated air must be diverted to a second baghouse or to the atmosphere until the 'blinding' is corrected. Manpower related to this operation is relatively high and replacement bags become almost prohibitively expensive. Disposal of the 'blinded' bags may also be regulated and have a long-term liability requirement for storage and/or disposition.

The homogenizer unit alloys for continuous operation related to airborne PM containment without the need of one or more baghouses while reducing the manpower requirements.

Airborne PMs are drawn or forced through the inlet(s) of the homogenizer and thence through the homogenizer unit. In many instances, water is the solvent of choice, although a non-foaming surfactant or detergent may be used to 'wet' any PMs that are coated with hydrophobic films. Should the PMs consist largely of dust derived from mineral crushing, then a solvent containing an acid of some type (or combined acids) may be circulated through the homogenizer. This dissolves the water and acid-soluble constituents from the PMs while leaving the silica and siliceous PMs as suspended particulates. Recirculation of the water-acid-PM solution allows for extended periods of operation while recovering valuable mineral constituents. The recirculation may continue until the solubility limits of the liquid are achieved to yield a saturated solution or 'pregnant liquor'.

Upon reaching saturation or near saturation, the pregnant liquor and PMs are transferred to a holding or equalization tank for settling or further treatment while 'fresh' leachant is shunted to the same homogenizer or a parallel homogenizer. No shutdown is required nor are any filter bags or similar devices.

Upon settling, the clarified liquor is treated to remove dissolved constituents and is 'recharged' for recirculation. The settled siliceous matter is removed via sludge transfer pumps to a central collection system, settled, and compacted via a filter press or similar device to yield the 'rinsate' and clean siliceous matter for disposition.

Should the pollution stream contain PMs including metals, then settling, magnetic removal, or polyelectrolyte coalescing will usually yield a largely heavy metal-free solution for recirculation into the PM containment system.

Flammable dust (microscopic and submicroscopic metal particles, wood dust or finely divided plant materials, sugar) and PMs, carbon monoxide, as well as hydrocarbons are rendered non-flammable due to the use of water as the primary solvent. A wetting agent enhances this entrainment of the PMs into the aqueous solvent thereby ensuring greater safety by reducing the risk of dust or solvent explosions.

Of equal importance is the reduction or elimination of airborne PMs being discharged to the atmosphere. These PMs may include asbestos, silica, silica-based compounds, minerals of an enormous variety, fine ashes, and finishing dusts. These PMs may be actively forced through one or more homogenizers with a suitable solvent. This solvent-PM mixture may be re-circulated until its density is such that shunting of this mixture to a holding tank is deemed necessary while another homogenizer or a bleed-and-feed system starts replenishing the solvent. The 'pregnant liquor' or slurry is allowed to settle to remove the entrained solids, is decanted and re-circulated or is sent to a disposition facility. No shutdown occurs with this program and air pollution is negated.

Alcohol Vapor Recovery

A great variety of alcohols are manufactured by either fermentation or synthesis. Most all of the liquid alcohols generate vapors during fermentation, storage, transfer, or production. Normally, these vapors are vented from the facility by discharging this product to the atmosphere or through an after-burner system.

Passing the vapors from the above procedures through the PPH allows for capture and recovery of these valuable entities.

Since all alcohol vapors and aerosols are readily ignited, fire risks are of a magnitude that safety problems may be equal to the other production problems. The homogenizer is largely static electricity-free and may be rendered so by proper design parameters. The use of explosion-proof pumps and ancillary cooling or refrigeration of product transfer lines reduces fire and explosion risks significantly.

Forcing the vapors or aerosols through transfer lines along with carbon dioxide or other inert gas prevents air (free oxygen) contact, thereby largely eliminating hazards during this phase. Maintaining the carbon dioxide 'blanket' throughout the recovery process should be adhered to at all times. Pressure tanks are not required since air displacement is the intent, not carbonation.

Passing the alcohol aerosol/vapor through the venturi using water leads to water removal requirements, but using the same alcohol as the solvent simply results in the aerosol or vapor being condensed into the parent stock. This allows for the steady decanting of the now liquid alcohol back to the processing line.

Should air-borne contaminants be included in the aerosol-vapor stream, then water scrubbing by the homogenizer will contain these products. Passing the alcohol-PM mixture through a suitable filter may be adequate to remove these contaminants. Distillation of this 'impure' alcohol will also ensure that all such PMs are removed.

In certain instances, the homogenizer can be utilized as the condenser for the distilling operations. This same homogenizer can readily remove alcohol vapors from the warehouse or storage facility and allow such vapors to be recovered for sale rather than simply be lost to the atmosphere by ventilation.

Not only can alcohol be recovered, other volatile hydrocarbons can be treated in a similar manner. This includes ketones, aldehydes, flavenoids, volatile organic and inorganic acids, or any other similar product. Each application will require certain safety features and recovery solvents, but the general process is similar in most aspects.

The engineering considerations should be based on explosion-proof pumps and electrical circuitry, static electricity abatement, and blanketing the incoming aerosol-vapor stream with an inert gas or gases. The inert gas blanket is retained throughout the homogenizer since the device is an integrated unit that does not allow for entry of oxygen until the alcohol is exposed to air at some later stage in the production line or at the point of usage.

Mycotoxin Removal and Recovery from Foodstuffs

Major crop losses throughout the world occur as a result of various grains, nuts, legumes, and meals made from these products becoming infested with a variety of molds. These molds produce very toxic metabolites called mycotoxins, the most familiar of which are the aflatoxins that are common on peanuts or grains. Should these aflatoxins be consumed by milk-producing livestock, then a 'milk toxin' is produced that has similar symptoms as the aflatoxins in the consumer (s). In certain instances, as much as 20% of the crop may be rendered unfit for human or livestock consumption in countries where regulations are in place to control the problem.

Many, if not most of these highly toxic agents are readily soluble in ethanol (grain alcohol). Washing the contaminated food product with this alcohol dissolves and removes the toxin and allows for toxin recovery and disposal as well as generating a toxin-free product. Such procedures have been largely ineffective in the past because the alcohol was difficult to remove from the food product and alcohol recovery and recycling was largely incomplete.

Passing the grain, nuts, or meals through an homogenizer equipped with a vibratory feeder allows for removal of the mycotoxins and related particulates by both dissolution of the toxins and washing of the food product with liquid alcohol.

Passing this alcohol-product slurry to a rotary drum dryer allows for alcohol removal by having the major portion of the liquid passing through the drum screens while having the heated air blast evaporating the remainder of the alcohol.

The cleansed, dry product can now be packaged or stored under proper conditions while the contaminated alcohol can report to an evaporator for vaporization of the solvent and recovery of the mycotoxin.

The alcohol vapors from both the homogenizer, the drum dryer, and the evaporator can now report to the condenser-homogenizer that utilizes a chiller to initiate droplet formation and subsequent fluid formation of the alcohol. This liquid is now recycled to the 'washing homogenizer' for use as the mycotoxin removal agent.

All such systems may be explosion-proof and managed by skilled technicians as would be expected at any solvent recovery facility.

The mycotoxin can be incinerated or be recovered for medical research or manufacture of mycotoxin derived drugs.

Odor Control and Sludge Reduction Using the Polyphasic Pressurized Homogenizer (PPH)

The PPH has the potential to alleviate many odor problems while also reducing sludge volumes at sewage treatment facilities (whether human or animal) by aerating or oxygenating the sludge in a very active mixing regimen.

By drawing the diluted sludge from a lagoon or digester, the PPH allows for rapid and pressurized mixing of ambient air into the sludge-water substrate. Odors are largely oxidized within a few seconds. The sludge passing through the PPH may be returned to the digester or lagoon. The oxygen not consumed by the oxidation of the odorants is then utilized to further oxidize the normally oxygen-poor sludge residues and allows for bacterial degradation to proceed more rapidly. The carbon-rich sludge is largely converted to carbon dioxide and naturally expelled in a gaseous form from the lagoon or digester.

Since the carbon-rich sludge compounds are largely converted to carbon dioxide, they no longer are part of the solid components occupying space within the lagoon or digester. By removing these same solids from the discharge, the BOD (Biochemical Oxygen Demand) and COD (Chemical Oxygen Demand) are also reduced significantly. Oxidation also prevents the pH from becoming a problem in many ways. For example, a very low pH allows for methane generation to occur in the digester or lagoon and release this gas into the atmosphere. Although this 'greenhouse gas' may be desirable in facilities that are able to utilize it as a source of heat energy or renewable cogeneration of electricity production; the 'sour' environment also tends to 'pickle' or preserve the organic compounds, which can later develop into very malodoriferous gases as they undergo anaerobic decay. This sour, low pH condition can be prevented by judicious use of the PPH which allows for aerobic digestion of the residual sludge.

Aerobic decay of the secondary sludges (e.g., that returned to the lagoon from the PPH) is highly desirable because it reduces the overall solid waste output from the sewage facility. Reduction in the volume or mass of these solids reduces expenses related to hauling these materials (whether as a value added fertilizer product in which the fertilizer has become 'concentrated' or as waste to a landfill after the material is dried or dewatered). Any need for incineration is reduced or eliminated as the volume of waste is greatly reduced, if not eliminated.

Hydroponics Applications and Associated Ancillary Modifications to the Polyphasic Pressurized Homogenizer (PPH)

The Polyphasic Pressurized Homogenizer (PPH) can be employed in introducing nutrients into water so as to provide an aqueous nutrient solution for growing plants hydroponically (i.e., without soil). The nutrient blend can be introduced into the PPH in place of the target material-containing stream through inlet 2 of FIG. 1. Water may be introduced through inlet 1 of FIG. 1. Applying the capabilities of the PPH to the practice of hydroponics and other forms of water-based (e.g., without soil) culturing of plants may be optimized when certain limited modifications are optionally made to the antechamber. Similarly, one or more modifications can be made to the exterior of the post chamber. In one embodiment, the venturi or reaction chamber may be as described above.

The modifications to the antechamber and post chamber advantageously provide for improved absorption of injected oxygen, nitrogen, or any other atmospheric gases directly into the nutrient stream being injected into the hydroponics root chamber(s). This allows for purging of at least a portion of the gases already dissolved in this same nutrient solution. Of special interest is the purging of absorbed carbon dioxide ($CO_2$) that is generated by the plants or has become entrained into the aqueous nutrient stream from air passing through the PPH. Any such introduced $CO_2$, when dissolved in an aqueous solution, can depress the pH of the nutrient solution and also negatively impact certain metabolic processes within plant cells.

Ancillary modifications: The various components involved with introduction, mixing, and retention of the mixed streams of the PPH (e.g., antechamber 3 of FIG. 1a, mixing chamber 4 and venturi 8 and throat 7 of FIG. 1a, retention chamber 18 of FIGS. 9a-9b) may be housed or contained entirely within an insulated covering or jacket. FIGS. 17 and 17a show such a modification including an insulative jacket IJ around these components of the PPH. For example, the entire exterior housing housing these structures and components may be covered with an insulative jacket. The transfer line connections (barbs, spigots, etc.) as well as all transfer lines leading to and from the PPH may be encased by insulation after they pass through a cooling system wherein the solution is cooled to the range wherein the temperature is amenable to plant root growth. This temperature may generally be below ambient temperature (e.g., ambient temperature in a warehouse or greenhouse setting where the hydroponics system may be housed may typically be 70° F. or more (e.g., 80° F.)). For example, in one embodiment, the solution may be cooled to a temperature in a range of 60° F. to 75° F., or 60° F. to about 70° F. When cooling, the resulting temperature of the nutrient solution will be cooler than the ambient temperature of the warehouse or greenhouse. For example, in the winter, if the warehouse is at 70° F., the nutrient solution may be maintained at a temperature less than 70° F. (e.g., 60° F.-65° F.). In the summer, if the warehouse is at 80° F., the nutrient solution may be maintained at a temperature less than the ambient temperature (e.g., maintained at 60° F.-75° F.). This cooling ensures that the now relatively cool nutrient solution has the ability to entrain oxygen, nitrogen, or other atmospheric gases or injected gas or gases at near maximum concentrations allowed at specific temperatures and pressure. These injected gases may be derived from an oxygen separation system or from commercially-available sources.

Oxygen or nitrogen or both can also be injected through a port or ports in the reaction chamber or the antechamber of the PPH (port 2 of FIG. 1) and thereby enhance the absorption of either or both gases in the nutrient solution. Where present, concentration of oxygen within the cooled nutrient solution may be maintained at a value from about 8 ppm to about 12 ppm. Where present, concentration of nitrogen within the cooled nutrient solution may be maintained at a value from about 8 ppm to about 12 ppm. Both oxygen and nitrogen may be provided in the nutrient solution. It may be important to cool the solution so as to prevent dissolved oxygen and nitrogen from leaving the system. For example, during the summer months, the ambient temperature of a greenhouse or warehouse may be so warm as to cause substantially all dissolved oxygen and nitrogen to leave the nutrient solution, were the solution allowed to warm to the ambient temperature. Thus, maintaining the nutrient solution at a cooler than ambient temperature can be an important aspect of an embodiment of the invention.

Where provided, gases such as oxygen and/or nitrogen can be injected into the PPH with the water stream, the nutrient stream, or both. In another embodiment, an additional inlet may be provided for such a purpose. In one embodiment, a separate PPH may be employed to dissolve the gases into one of the streams (e.g., the water stream) prior to mixing of the water stream with the nutrient stream.

Cooling the nutrient solution being transferred from a nutrient reservoir (e.g., by pumping and/or metering mechanisms) to the PPH and thence to the root chambers enhances the ability of the same solution to purge carbon dioxide while retaining a portion of dissolved oxygen and nitrogen gases. Cooling of the nutrient solution in its storage tank may materially enhance gas dissolution-solution.

Oxygen absorption by plant roots maintains or enhances the health of the plants and also counters the acidic conditions of the nutrient solution normally brought about when retained carbon dioxide gas is converted to carbonic acid ($H_2CO_3$).

Injection of nutrients, etc. via a manifold or ports may be achieved as described previously (e.g., port 2 of FIG. 1). While any suitable nutrient may be injected, one suitable contemplated nutrient blend is TURBO MY GARDEN, available from Alchem Environmental LLC, located in Salt Lake City, Utah. This proprietary nutrient blend includes naturally-occurring plant enhancing nutrients that are characterized as synergistic major macro, micro, sub-micro, organometallics and non-metallics compound nutrients, along with their respective trace elements. TURBO MY GARDEN is a natural, non-toxic product, as opposed to more harsh chemical fertilizers.

Here are just some of the identifiable components discovered in TURBO MY GARDEN:

| Nitrogen | Humic & Fulvic Acids | Flavenoids | Sulfur |
| --- | --- | --- | --- |
| Phosphorus | Growth Regulators | Lignins | Chlorides |
| Potassium | Growth Promoters | Silica | Molybdenum |
| Calcium | Growth Inhibitors | Algin | Sodium |
| Magnesium | Enzyme Stimulators | Cellulose | Cobalt |
| Iron | Chelation Agents | Hemi-Cellulose | Vanadium |
| Manganese | Natural Sugars | Pectins | Selenium |
| Copper | 17 Amino Acids | Surfactants | Boron |
| Zinc | Vitamins | Terpenoids | Iodine |

The above-listed ancillary modifications allow for the introduction of a variety of nutrient solutions (e.g., in liquid concentrate form, such as TURBO MY GARDEN), as well as gases or even finely-ground dried nutrients in powder form to the PPH so as to provide a much simplified program of monitoring and feeding of nutrients to the plants in the system. A manifold provided with the PPH may measure and inject water as based on need as established by an operator or automated measuring-valving system, or it may dispense nutrient solutions, gas or gases, powders, etc. on demand based on either operator demand or automated system analysis demands.

Atmospheric nitrogen absorption by bacterial commensals (e.g., symbiotic or parasitic bacteria such as *Rhizobium* spp., *Bradyrhizobium* spp., and *Azorhizobium* spp.) living in nodules on the roots of leguminous plants can be increased by having the maximal concentration of nitrogen in the nutrient solution surrounding the plant roots. The nitrogen is converted by the enzyme nitrogenase to ammonium ions and then to ammonia (by its reaction with the water in plant cells) whence it is absorbed directly.

The simplified reaction is: atmospheric nitrogen in water reacts with nitrogenase to form ammonium ions:

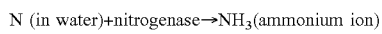

N (in water)+nitrogenase→$NH_3$(ammonium ion)

The ammonium ion then reacts with water to form ammonia and an atom of hydrogen.

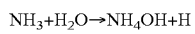

$NH_3+H_2O \rightarrow NH_4OH+H$

Proteins and other nitrogenous compounds are then manufactured biochemically in the plant's cells from the metabolic action of enzymes and ammonia in coordination with carbon, hydrogen, oxygen, and sulfur (if required).

Ammonium ion in concentrations exceeding the required limits by the leguminous plants are excreted into the nutrient solution and can be utilized by non-leguminous plants for the same metabolic processes, thus the ammonium ion is not readily released to the atmosphere as a pollutant. Other plants and certain chlorobacteria also can 'fix' nitrogen by enzymatic means and can be cultured with the intent of producing ammonium ion for the same or similar purposes.

The purpose of using the legumes (e.g., in combination with other produce plants such as lettuce to be harvested) is to: 1. provide the ammonium ion that is to be converted to ammonium hydroxide by both the legumes and the higher produce plants as a source of metabolic nitrogen; 2. provide a harvestable crop of fruits (e.g., beans, peas, or other legumes) for consumption; 3. reduce the amount of nitrates one needs to buy and add to most nutrient solutions and thereby lower costs and hazards related to storage of nitrates on site; and/or 4. legumes of certain types are readily cultured by hydroponic means, while other plants have been suitable only for field (i.e., including soil) or experimental efforts.

FIG. 18 is a schematic illustration of an exemplary hydroponics system where a PPH apparatus is employed to mix the water, nutrient, and gas streams to result in a nutrient solution that is provided to the hydroponic grown plants. Spent nutrient solution may be recycled for reuse, either through the PPH, or directly to the plants (e.g., bypassing the PPH). The recycling components may include monitoring structure for determining what and how much, of the inputs (water, nutrients, $O_2$, $N_2$) should be added. The system may also include a cooling unit to cool the nutrient solution and/or the inputs to a desired temperature (e.g., 60° F. to 75° F.), as described above.

Methane Purification and Associated Ancillary Modifications to the Polyphasic Pressurized Homogenizer (PPH)

The Polyphasic Pressurized Homogenizer (PPH) can be employed in purifying a biogas or other raw methane containing stream that includes various contaminants. For example, such a stream may be generated through various agricultural uses (e.g., diary farm, hog farm, other animals, etc.). Such a system may also be appropriate for use in purifying raw methane recovered from a sour natural gas well or for purifying a sewer gas stream.

DISCUSSION: Methane is not soluble in water under ambient conditions and is readily purified by passing a mixed gas stream through the PPH with water that has been chilled or that contains a suitable sequestering agent in solution. Use of chilled water may be preferred where possible, due to cost considerations.

The mixed gas stream may contain methane and other constituents from the source materials, notably animal manures and/or plant wastes (e.g., in the case of biogas sourced raw methane). An exemplary raw methane stream may include methane, carbon dioxide, and water vapor. One or more of ammonia, volatile organic compounds (VOCs) including free fatty acids (FFAs), hydrogen sulfide, and particulate materials (PMs) may also often be present. Methane from other sources (e.g., a sour natural gas well) may include at least some of the same components (e.g., methane, carbon dioxide, water vapor, hydrogen sulfide, etc.).

Carbon dioxide is a major constituent in the gas generated during fermentation of the manures and must be removed from the gas mixture to enhance its fuel value. Hydrogen sulfide gas is also often present and has negative impacts on the combustion equipment (e.g., electrical generator) and the people or other living creatures it comes in contact with due to its toxicity. Both gases are readily removed by the PPH system. Ammonia is also sometimes present, depending on the particular application associated with the generated biogas. Ammonia is also removable by the PPH system. Depending on specific configurations, a single PPH may be employed to remove more than one target contaminant, or multiple PPH units may be employed (e.g., in series) to sequentially remove desired target contaminants such as any of those identified above from a given raw methane stream. FIGS. 19A and 19B illustrate exemplary systems and methods for purification of a raw methane stream.

The 'raw' gas may be passed into the PPH and may be exposed to chilled water. This causes the water vapor (a constituent typically present in any of various raw methane streams) in the gas to condense, forming liquid water. The carbon dioxide (also typically present) dissolves to yield carbonic acid ($H_2CO_3$). In some raw methane streams, there may be negligible levels of other contaminant components.

In such a simple system, the chilled water stream and the raw methane stream enter the PPH, and the water vapor and carbon dioxide are stripped out of the raw methane stream, producing a purified methane stream (e.g., 90% or higher purity methane, 91%, 92%, 93%, 94%, 95%, 96%, 97%, 98%, or 99% or higher purity methane).

A typical raw methane stream may typically include 40 to about 50% methane, 40 to 60% carbon dioxide, and/or typically 5 to 10% water. Such fractions may be molar fractions. Such percentages of any gaseous stream constituents may be on a molar basis. Of course, depending on any particular application, the particular percentages may vary from such typical values, and may be even higher or lower than the upper or lower limits of the above ranges. Such is merely exemplary. Relatively smaller percentages of other contaminants may also be present (e.g., hydrogen sulfide, ammonia, VOCs, etc.). For example, such other contaminants may be present at up to about 10%, up to about 5%, up to about 3%, up to about 2%, up to about 1%, or less than 1%. For example, the fraction of such components may be up to about 0.1% (e.g., 1000 ppm). In some raw methane streams, one or more such components may not be present at a detectable level (e.g., less than 1 ppm).

The PPH may produce a purified methane stream (e.g., 90% or higher purity methane) and an acidified water stream. The acidified water stream (acidified by dissolution of the carbon dioxide, forming carbonic acid) may be disposed of or further processed in any way desired. In one example, it may simply be allowed to warm up, driving the carbon dioxide out, where it may simply be vented, or may be captured (e.g., a high purity $CO_2$ stream could thus be captured and stored for subsequent use (e.g., as a plant metabolite).

The raw methane stream may in some embodiments include hydrogen sulfide. Where such is present, the hydrogen sulfide dissolves in the chilled water as a result of passage through the PPH, and becomes converted to hydrogen and elemental sulfur. If oxygen is present (e.g., if the chilled water is oxygenated, or oxygen is otherwise available, the hydrogen may combine with oxygen to yield water. In another embodiment, hydrogen gas (e.g., diatomic hydrogen) may be formed, which may remain with the purified methane stream. Such hydrogen gas may increase the fuel BTU value of the resulting purified methane stream (e.g., the stream of methane including a percentage of hydrogen may be fed to any desired engine, burner, etc. as would normally be the case). The elemental sulfur forms a fine crystalline form and settles to the bottom of the reservoir or remains in suspension within the water constituent exiting the PPH. Such precipitated elemental sulfur may be retrieved and used or sold as an additional value added product (e.g., used to make sulfuric acid, etc.). Hydrogen sulfide may typically be present from negligible levels (e.g., 1 ppm or less), up to very high levels. For example, the $H_2S$ may be present up to 5%, or 10%, or possibly even higher, depending on the particular source of the raw methane stream. More typical examples may include up to several hundred ppm of $H_2S$ (e.g., from 300 to about 1000 ppm, or 700-800 ppm of $H_2S$).

In some instances, ammonia may be present within the raw methane stream, e.g., depending on the particular source of the raw methane (e.g., chicken, turkey, or other poultry agricultural installations may generate significant quantities of ammonia). Where ammonia is, or ammonium constituents are present, the chilled water may be oxygenated. Such oxygenation may aid in solubilizing ammonia and in its conversion to a compound that will precipitate out of the chilled water. For example, where $CO_2$ is also present, ammonium carbonate may be formed. If desired, an appropriate catalyst may be used to increase yield, pushing the equilibrium characteristics towards the ammonium carbonate product and away from the reactants. In an embodiment, ammonia dissolved in the chilled water could be drawn out of the PPH, and subsequently warmed, releasing purified ammonia gas, which could be captured for subsequent use, as desired (e.g., similar to capture of $CO_2$ which could be released from the chilled water, if such water is drawn off and then warmed, releasing the dissolved gas (e.g., either ammonia or $CO_2$) therein.

If desired, any desired adjuvant may be added to the chilled water, for reaction with one or more target contaminants. For example, a hydroxide (e.g., an alkali metal or alkali earth metal hydroxide, such as potassium hydroxide) may be added to the chilled water for reaction with the carbon dioxide, forming potassium carbonate. Such reaction may also produce hydrogen and oxygen gases. The potassium carbonate product could be collected (e.g., it precipitates out) and subsequently heated. Such heating would regenerate the potassium hydroxide, and release purified $CO_2$ gas, which could be collected for any desired use (e.g., plant metabolite, etc.)

Since cold water is much more amenable to gas entrainment, including carbon dioxide, hydrogen sulfide, oxygen, or any other gas, chilling the water is highly beneficial to both carbon dioxide capture, sulfur formation, oxygen retention etc. The carbon dioxide can dissolve in the cold water (e.g., 20° C.; 68° F.) to form carbonic acid. Should ammonia ($NH_3$) or ammonium ($NH_4$) be present, it is also soluble in the cold water and may bond with the carbon dioxide to form ammonium carbonate.

EMBELLISHMENTS: Insulating the exposed surfaces of the PPH system aids in delaying the transfer of heat to the interior of the PPH. Chilling the water and passing it to the PPH system results in converting the water vapor in the raw methane to liquid water, and converting the hydrogen sulfide to sulfur and hydrogen gas (as the hydrogen sulfide gas dissolves more readily and at higher concentrations into chilled water). In some embodiments, multiple PPH units may be employed in series in order to dissolve oxygen into the chilled water (e.g., where the raw methane stream includes ammonia), and/or to target removal of a particular contaminant within a given PPH, followed by removal of another contaminant within a downstream PPH. Of course, such staged PPH units in series could also be used to increase the purity of the resulting purified methane product stream, e.g., where two or more PPH units in series may serve to remove the same contaminant. Any holding tanks for storing the chilled water may be insulated in a similar manner as the PPH and its various entry and egress lines may be insulated, to maintain the chilled water at a reduced temperature, and to hold dissolved gases entrained therein, where desired. The chilled water may be recycled through the PPH unit, and/or some portion (or all) of the chilled water may be drawn off for removal of any entrained gases, settling out and removal of any precipitates, etc. It will be apparent that numerous variations are possible, although it will be appreciated that in each such configuration, use of the PPH allows a raw methane stream to be purified, producing a purified methane stream by introducing the raw methane stream and a chilled water stream into the PPH unit, where at least carbon dioxide is pulled out from the raw methane stream, and drawn into (dissolved into) the chilled water stream. Other contaminants, where present, may similarly be drawn into the chilled water stream from the raw methane stream.

In some embodiments, oxygen may be dissolved within the chilled water (e.g., at a concentration elevated as compared to what would exist naturally, e.g., by running air or another oxygen containing stream and chilled water through a pre-treatment PPH, to oxygenate the chilled water. Such oxygen may then be available to react with hydrogen which dissolves into the water (e.g., from $H_2S$) or another source, to form water. Where $H_2S$ is the hydrogen source, elemental sulfur, which settles out, is also formed.

Such raw methane streams typically include carbon dioxide. The carbon dioxide is converted to carbonic acid upon dissolution in the water stream, leaving a highly purified methane gas stream that can then be conveyed to an apparatus for generation of electricity, for heat generation, or other use of the purified methane as fuel (e.g., to an internal combustion engine of a generator, to a burner, or other desired apparatus). The purified methane could be directly sent to such apparatus, or may be stored in pressurized storage tanks for later dispensing as needed.

A suitable type of insulation may enclose the PPH system and both entry and egress conduits or lines. Any holding tanks, settling tanks, or other structure upstream or downstream from the PPH may similarly be insulated, to keep the chilled water as cool as possible. Of course, where it is desired to drive dissolved gases out of solution, the units may not be insulated (e.g., where $CO_2$ is to be driven out of solution by heating, ammonia gas is to be driven out of solution by heating, etc.). Where insulation is present, such insulation may be such as that described above in the hydroponics applications (where it was also desirable to chill the streams to increase gas dissolution in the water). Excess water may be bled off to storage tanks, and some portion of the water stream may be recycled, as desired. Where produced, any elemental sulfur can be allowed to settle from the product water while the carbon dioxide can be driven off (e.g., by heating), and diverted to storage tanks to supply carbon dioxide for use as a plant metabolite, where the carbon dioxide hasn't been converted to carbonate (e.g., ammonium carbonate). Where carbonate is formed as described above, carbon dioxide could be produced therefrom by heating the carbonate, regenerating the hydroxide adjuvant for addition to the chilled water.

Any free fatty acids (FFAs) or other VOCs that may be present could be trapped on an oleophilic mesh or other oleophilic material, or collected on a very cold metal surface (but still above 32° F. (freezing)), for periodic removal. For example, free fatty acids that may be present within the raw methane stream could be contacted with a cooled metal surface (e.g., below about 60° F., below about 55° F., or from about 45° F. to about 55° F.), causing such constituents to coalesce into a deposited layer on the cold metal surface. Such removal of FFAs and/or other VOCs could be performed as a pre-treatment step, before introducing the raw methane stream into the PPH. Removal of VOCs (including FFAs) could alternatively be achieved through use of a pre-treatment PPH system that injects ozone into the PPH, with the raw methane stream. Such ozone would remove the VOCs from the raw methane stream before sending the pretreated raw methane stream to the PPH for treatment with the chilled water.

Particulate matter may be readily removed from the water via filters or allowed to settle in company with any elemental sulfur, and/or other precipitates, as desired, thereby allowing cold, filtered or clarified water to be recycled to the PPH. Excess water generated from the water stream with the contaminants contained therein (e.g., after removal of elemental sulfur, particulate matter, carbonates, and/or other contaminants) can be transferred to the methane generator (e.g., used on the farm) or used for other purposes. The sulfur can be removed from the storage tank(s) at intervals, dried, and sold or used or other purposes.

Contact of the raw methane stream with the chilled water in the PPH also removes most of the entrained water vapor via condensation, thereby allowing for the passage of 'dry' methane to the internal combustion engine, burner, or other apparatus employing methane as a fuel.

The table below presents the solubility of carbon dioxide in water at 0, 10, 20, 40, 50, and 60° C. or its equivalent as degrees F. It will be readily apparent that at lower temperature, the water is able to carry much more dissolved gases (such as carbon dioxide) therein.

| Temp in C. or F. | cc/L of $H_2O$ | cc/gal of $H_2O$ | L/gal of $H_2O$ | g/gal of $H_2O$ | oz/gal of $H_2O$ |
| --- | --- | --- | --- | --- | --- |
| 0/32 | 1710 | 6472 | 6.472 | 12.8 | 0.45 |
| 10/50.0 | 1295 | 4901 | 4.901 | 6.96 | 0.34 |
| 20/68 | 880 | 3330.8 | 3.330 | 6.58 | 0.23 |
| 40/104 | 440 | 1665. | 1.665 | 3.29 | 0.11 |
| 50/122 | 400 | 1513 | 1.513 | 2.99 | 0.055 |
| 60/140 | 360 | 1362.4 | 1.362 | 2.69 | 0.09 |

Chilling of the water stream may be to any desired temperature below ambient temperature, such as described above within the hydroponics applications. For example, ambient temperature may represent the temperature in a warehouse, greenhouse, or other setting where the system may be housed. Such may typically be 70° F. or more (e.g., 80° F.)). For example, in one embodiment, the water stream may be cooled to a temperature in a range of 60° F. to 75° F., or 60° F. to about 70° F. When cooling, the resulting temperature of the water stream will be cooler than the ambient temperature of the warehouse, greenhouse, or other environment housing the system. For example, in the winter, if the environment is at 70° F., the water stream may be maintained at a temperature less than 70° F. (e.g., 60° F.-65° F.). In the summer, if the environment is at 80° F., the water stream may be maintained at a temperature less than the ambient temperature (e.g., maintained at 60° F.-75° F.). This cooling ensures that the now relatively cool water stream has the ability to entrain carbon dioxide or other gases at near maximum concentrations allowed at specific temperatures and pressure. Oxygen or other gases may also be injected into the chilled water stream. Such adjuvant dissolved gases may be derived from an oxygen separation system, from commercially-available sources, or even air.

In order to better aid dissolution of the carbon dioxide (and hydrogen sulfide and/or ammonia gases, if present) to be removed from the raw methane stream and pulled into the water stream, the various components involved with introduction, mixing, and retention of the mixed streams of the PPH (e.g., antechamber 3 of FIG. 1a, mixing chamber 4 and venturi 8 and throat 7 of FIG. 1a, retention chamber 18 of FIGS. 9a-9b) may be housed or contained entirely within an insulated covering or jacket. FIGS. 17 and 17a show such an embodiment including an insulative jacket IJ around these components of the PPH. For example, the entire exterior housing housing these structures and components may be covered with an insulative jacket. The transfer line connections (barbs, spigots, etc.) as well as all transfer lines leading to and from the PPH may be encased by insulation. Cooling systems (e.g., heat exchangers) may be present upstream and/or downstream of the PPH to cool the water stream, and to maintain any of the product streams at a cooled temperature, where it is desired to maintain gases is solution. Once it is desired to drive such gases out of solution, the stream may be heated. It may be chilled again, before recycle of the chilled water back to the PPH. For example, water recycled back to the PPH from the contaminant isolation stream (the product stream including the water) may be chilled again, before recycling back into the PPH to strip $CO_2$ and $H_2S$ from a new or continuing raw methane stream. Storage tanks for storing any such product streams or the recycled water stream may be insulated, where such is desired.

As described above in the hydroponics description, where the chilled water stream is oxygenated, concentration of oxygen within the cooled water stream may be maintained at a value from about 8 ppm to about 12 ppm, or perhaps even higher, when introduced into the PPH. Use of an upstream PPH to inject the oxygen into chilled water may be employed (i.e., the system may include 2 or more PPH units). Use of a PPH to inject and dissolve the oxygen results in oxygen concentrations at or near the maximum solubility of the gas within the water at a given temperature. Such levels are significantly higher than are achievable through simple sparging, due to the intimate homogenization of the gaseous oxygen containing stream into the water stream. For example, very small bubbles are formed, orders of magnitude smaller than occurs when sparging. Cooling the stream prevents dissolved oxygen from leaving the system. For example, during the summer months, the ambient temperature of an environment where the methane purification system is located may be so warm as to cause substantially all dissolved gasses to leave the water stream, were the stream allowed to warm to the ambient temperature. Thus, maintaining the stream at a cooler than ambient temperature can be an important aspect of an embodiment of the invention.

Elements
   Homogenizer unit
   Entry port or port
   Ante-mix chamber or chambers
   Nozzle or nozzle, jet or jets
   Mixing chamber
   venturi
   retention chamber
   discharge chamber
Connections
   Homogenizer unit
   GAS AND SOLVENT ENTRY PORTS OF HOMOGENIZER UNIT
     ANTE-MIX CHAMBER EMBODIMENTS
     MIXING CHAMBER EMBODIMENTS
     VENTURI EMBODIMENTS
     RETENTION TUBE EMBODIMENTS
     DISCHARGE EMBODIMENTS V. Charts The following charts have been compiled to include many of the compounds that are formed by substitution reactions from other compounds and contributing cations and anions of the alkali and alkali-earth metals as well as ammonia. Not all of the known compounds of these elements or ammonia are included, rather, these are simply specific examples. An 'X' in any space in the column under the elemental or compound symbol indicates the element readily forms that compound under specific conditions whereas less common reactions or no reactions are indicated by a dashed line (---). Approximately 20-50% of the known compounds for the listed elements and ammonia are presented in the table.

Although ammonia is not an element, its chemical reactivity and the formation of parallel compounds that are very similar to those of the alkali and alkali-earth compounds resulted in the compound being included on the table.

The suffix, 'ate', as applied to organic compounds infers or indicates the compound was derived from bonding of the organic compound and an inorganic acid, base, or element. A lower case 'x' in a chemical symbol indicates that a fixed number of atoms of that element does not always exist in nature, rather the numbers can be variable in most or many instances.

Certain suffixes end in 'ide', 'ite', or 'ate', as in bromide, bromite, or bromate. No oxygen is present in the anion, but the number of atoms of the element forming that anion can vary from one to three. Conversely, the suffix, 'ite' indicates one oxygen atom is present in the anion and 'ate' indicates three or more oxygen atoms are present in the anion.

All of the compounds marked with an 'X' can be formed within the homogenizer unit as long as the proper precursor chemistries are suitable for the occurrence of such reactions. Other parallel chemical reactions that are not listed on the table may also occur, especially with oils or fatty acids and mineral acids. In certain instances, combinations of sodium and potassium with a single anion may result in dicationic molecules to yield a sodium-potassium salt or compound. One such example would be sodium-potassium tartrate.

The listed compounds may form in an aqueous matrix or in air (This applies to ammonia, $NH_3$.). In certain instances, compound formation results from 'contact' of a gas (fluorine, chlorine) with an alkali earth or alkali-earth metal or their respective oxide or hydroxide. Others form in an aqueous matrix by substitution.

CHART 1

COMPOUNDS OF THE ALKALI, ALKALI-EARTH METALS, AND AMMONIA THAT WILL FORM DURING PASSAGE THROUGH THE POLYPHASIC PRESSURIZED HOMOGENTZER.

| Element/Compound | $NH_3$ | Be | Ca | Li | Mg | K | Na |
|---|---|---|---|---|---|---|---|
| Acetate $C_2H_3O_7$ | X | X | X | X | X | X | X |
| Arsenate $AsO_4$ | X | — | X | X | X | X | X |
| Arsenide As | — | — | X | — | X | — | — |
| Arsenite $AsO_3$ | X | — | X | — | X | X | X |
| Benzoate $C_7H_5O_2$ | X | — | X | X | X | X | X |
| Bromate $BrO_3$ | X | — | X | — | X | X | X |
| Bromide Br | X | X | X | X | X | X | X |
| Carbonate $CO_3$ | X | X | X | X | X | X | X |
| Chlorate $ClO_3$ | X | — | X | X | X | X | X |
| Chloride Cl | X | X | X | X | X | X | X |
| Chlorite $ClO_2$ | — | — | X | — | — | X | X |
| Chromate $CrO_4$ | X | — | X | X | X | X | X |
| Citrate $C_6H_5O_7$ | X | — | X | X | X | X | X |
| Cyanide Cn | X | — | X | — | X | X | X |
| Ferricyanide $FeCn_6$ | X | — | X | — | X | X | X |
| Ferrocyanide $FeCN_6$ | X | — | X | — | X | X | X |
| Fluoride F | X | X | X | X | X | X | X |

CHART 1-continued

COMPOUNDS OF THE ALKALI, ALKALI-EARTH METALS, AND AMMONIA THAT WILL FORM DURING PASSAGE THROUGH THE POLYPHASIC PRESSURIZED HOMOGENTZER.

| Element/Compound | $NH_3$ | Be | Ca | Li | Mg | K | Na |
|---|---|---|---|---|---|---|---|
| Formate $CHO_2$ | X | — | X | X | X | X | X |
| Hydride H | — | X | X | X | X | X | X |
| Hydroxide OH | X | — | X | X | X | X | X |
| Iodate $IO_3$ | X | — | X | X | X | X | X |
| Iodide I | X | X | X | X | X | X | X |
| Lactate $C_3H_5O_3$ | X | — | X | — | X | X | X |
| Laurate $C_{12}H_{23}O_2 \cdot C_{12}H_{24}O_2$ | X | — | X | X | X | X | — |
| Molybdate $MoO_4$ | X | — | X | X | X | X | X |
| Nitrate $NO_3$ | X | — | X | X | X | X | X |
| Nitride $N_2$ | — | X | X | X | X | X | X |
| Nitrite $NO_2$ | X | — | X | X | X | X | X |
| Oleate $C_{18}H_{33}O_2 \cdot C_{18}H_{34}O_2$ | X | — | X | — | X | X | X |
| Oxalate $C_2O_2$ | X | X | X | X | X | X | X |
| Oxide Ox | — | X | X | X | X | X | X |
| Phosphate $PO_4$ | X | X | X | X | X | X | X |
| Phosphite $PO_2$ | X | — | X | — | — | X | X |
| Proprionate $C_3H_5O_2$ | X | X | X | — | — | X | X |
| Salicylate $C_7H_5O_2$ | X | — | X | X | X | X | X |
| Selenate $SeO4$ | X | X | X | — | X | X | X |
| Selenide Se | X | — | X | X | X | X | X |
| Silicate $SixOx$ | — | X | X | X | X | X | X |
| Silicide $Si_2$ | — | — | — | X | X | — | — |
| Stearate $C_{18}H_{35}O_2 \cdot C_{18}H_{36}O_2$ | X | X | X | X | X | X | X |
| Sulfate $SO_4$ | X | X | X | X | X | X | X |
| Sulfide S | X | X | X | X | X | X | X |
| Sulfite $SO_3$ | X | — | X | X | X | X | X |
| Tartrate $C_4H_4O_6$ | X | — | X | X | X | X | X |
| Tellurate $TeO_4$ | X | — | — | — | — | X | X |
| Telluride Te | — | — | X | — | X | X | X |
| Tellurite $TeO_3$ | — | — | X | — | — | X | X |
| Valerate $C_5H_9O_2$ | X | — | X | — | — | — | X |

VI. Solubility Chart

The Solubility Chart as presented below lists the solubility or insolubility characteristics of certain compounds in water or acid. Since many compounds are only weakly soluble in water, two symbols are used to indicate whether or not the compound is very soluble in water or only weakly soluble in water. These are, respectively, 'W' for the compounds that are very soluble in water and 'w' for compounds that are weakly soluble in water. No indication is offered for solubilities relating to hot or cold water or to the exact quantities of the compounds that are soluble.

In a similar manner, acid solubility is marked by an 'A'. No lower case letter is used to specify the degree of solubility in a certain acid or acids. Likewise, no indication is offered for organic solvent or base solubility.

Insoluble compounds in acid or water are identified by an 'I', while compounds that 'decompose' to yield other compounds than the 'parent' compound are identified by 'D'.

Selected elements and one compound, ammonia or $NH_4$ are listed vertically in the left column while the compound is listed in the top row of the chart.

The names for the compounds are derivatives of the anions, thus aluminum acetate is derived from the element, aluminum and acetic acid that is bonded as the anion to the aluminum.

Not every known compound of the selected elements is listed, just examples of those that would form under the proper conditions in the Polyphasic Pressurized Homogenizer. As such, the list is not meant to be exhaustive. Even then, those that dissolve in water would not necessarily form in an acidic matrix while those that form in an acidic matrix are generally not soluble in water.

In certain instances, a compound will form only if the element is in a finely divided or powder form or if it is already in another form. For instance, certain alkali and alkali-earth elements dissolved in water to form their respective hydroxide compound. Once formed, these hydroxides readily undergo substitution reactions to yield carbonates, bicarbonates, and a variety of halogenated compounds or acidic salts. Attempts to dissolve the element in an acid may be quite dangerous and life-threatening. In other instances, especially when dealing with organic acids, the oxide or hydroxide of a compound may be first formed and then mixed with the appropriate acid with an extended mixing period to yield the proper acidic salt compound.

CHART S1

SOLUBILITY OF SELECTED ELEMENTS AND COMPOUNDS

| Element/compound | Acetate —$(C_2H_3O_7)$ | Arsenate —$(AsO_4)$ | Arsenide —$(AsO_3)$ | Benzoate —$(C_7H_5O_2)$ | Bromide | Carbonate |
|---|---|---|---|---|---|---|
| Al | W Al(—)$_3$ | A Al(—) | — | — | W $AlBr_3$ | — |
| $NH_4$ | W $NH_4$(—) | W $(NH_4)_3$(—) | W $NH_4AsO_2$ | W $NH_4$(—) | W $NH_4Br$ | W $(NH_4)_2CO_3$ |

CHART S1-continued

SOLUBILITY OF SELECTED ELEMENTS AND COMPOUNDS

| | | | | | | |
|---|---|---|---|---|---|---|
| Sb | — | A<br>Sb(—) | A<br>Sb(—) | — | D<br>SbBr$_3$ | — |
| Ba | W<br>Ba(—)$_2$ | W<br>Ba$_3$(—)$_2$ | — | W<br>Ba(—)$_2$ | W<br>BaBr$_2$ | W<br>BaCO$_3$ |
| Be | W<br>Be(—)$_2$ | — | — | — | W<br>BeBr$_3$ | I<br>BeCO$_3$ + Be(OH)$_2$ |
| Bi | W<br>Bi(—)$_3$ | A<br>Bi(—) | — | A<br>Bi(—)$_3$ | D<br>BiBr$_3$ | — |
| B | — | W<br>B(—) | — | — | D<br>BBr$_3$ | — |
| Cd | W<br>Cd(—)$_2$ | A<br>Cd$_3$(—)$_2$ | — | W<br>Cd(—)$_2$ | W<br>CdBr$_2$ | A<br>CdCO$_3$ |
| Ca | W<br>Ca(—)$_2$ | W<br>Ca3(—)$_2$ | w<br>Ca(—)$_2$ | W<br>Ca(—)$_2$ | W<br>CaBr$_2$ | W<br>CaCO$_3$ |
| Cr | W<br>Cr(—)$_3$ | — | — | — | I<br>CrBr$_3$ | W<br>CrCO$_3$ |
| Co | W<br>Co(—)$_2$ | A<br>Co$_3$(—)$_2$ | A<br>Co$_3$H$_6$(—)$_4$ | W<br>Co(—)$_2$ | W<br>CoBr$_3$ | A<br>CoCO$_3$ |
| Cu | W<br>Cu(—)$_2$ | A<br>Cu$_3$(—)$_2$ | A<br>CuH(—) | w<br>Cu(—)$_2$ | W<br>CuBr$_2$ | — |
| Au' | — | — | — | — | W<br>AuBr | — |
| Au''' | — | — | — | — | W<br>AuBr$_3$ | — |
| H | W<br>C$_2$H$_4$O$_2$ | W<br>H$_3$AsO$_4$ | — | W<br>C$_7$H$_6$O$_2$ | W<br>HBr | — |
| Fe'' | W<br>Fe(—)$_2$ | W<br>Fe$_3$(—)$_2$ | — | W<br>Fe(—)$_2$ | W<br>FeBr$_2$ | W<br>FeCO$_3$ |
| Fe''' | W<br>Fe(—)$_6$ | A<br>Fe(—) | — | A<br>Fe$_2$(—)$_6$ | W<br>FeBr$_3$ | — |
| Ga | W<br>4Ga(—)$_3$ | — | — | — | W<br>GaBr$_3$ | — |
| Ge | — | — | — | — | D<br>GeH$_3$Br | — |
| Ir | — | — | — | — | W<br>IrBr$_3$<br>D<br>IrBr$_4$ | — |
| Pb | W<br>Pb(—)2 | A<br>PbH(—) | — | w<br>Pb(—)$_2$ | W<br>PbBr$_2$ | A<br>PbCO$_3$ |
| Li | W<br>Li(—) | w<br>Li$_3$(—) | — | W<br>Li(—) | W<br>LiBr | W<br>Li$_2$CO$_3$ |
| Mg | W<br>Mg(—)2 | A<br>Mg$_3$(—)$_2$ | W<br>Mg$_3$(—)$_2$ | W<br>Mg(—)$_2$ | W<br>MgBr$_2$ | W<br>MgCO$_3$ |
| Mn | W<br>Mn(—)2 | W<br>MnH(—) | A<br>Mn$_3$H$_6$(—)$_4$ | W<br>Mn(—)$_2$ | W<br>MnBr$_2$ | W<br>MnCO$_3$ |
| Mo | — | — | — | — | I<br>MoBr$_2$ | — |
| Hg' | W<br>Hg(—) | A<br>Hg$_3$(—) | A<br>Hg$_3$(—) | A<br>Hg$_2$(—)$_2$ | A<br>HgBr | A<br>Hg$_2$CO$_3$ |
| Hg'' | W<br>Hg(—)$_2$ | A<br>Hg$_3$(—)$_2$ | A<br>Hg$_3$(—)$_2$ | W<br>Hg$_3$(—)$_2$ | W<br>HgBr$_2$ | — |
| Ni | W<br>Ni(—)$_2$ | A<br>Ni$_3$(—)$_2$ | A<br>Ni$_3$H$_6$(—)$_4$ | w<br>Ni(—)$_2$ | W<br>NiBr$_2$ | — |
| K | W<br>K(—) | W<br>K$_3$(—) | W<br>K$_3$AsO$_3$ | W<br>K(—) | W<br>KBr | W<br>K$_2$CO$_3$ |
| Rh | — | — | — | — | — | — |
| Ru | — | — | — | — | — | — |
| Ag | W<br>Ag(—) | A<br>Ag$_3$(—) | A<br>Ag$_3$(—) | w<br>Ag(—) | A<br>AgBr | A<br>Ag$_2$CO$_3$ |
| Na | W<br>Na(—) | W<br>Na$_3$(—) | W<br>Na$_2$H(—) | W<br>Na(—) | W<br>NaBr | W<br>Na$_2$CO$_3$ |
| Os | — | — | — | — | — | — |
| Pd | — | — | — | — | I<br>PdBr$_3$ | — |
| Pt | — | — | — | — | I<br>PtBr$_3$ | — |
| Sn'''' | W<br>Sn(—)$_4$ | — | — | — | W<br>SnBr$_4$ | — |
| Sn'' | D<br>Sn(—)$_2$ | — | A<br>Sn(—)$_2$ | — | W<br>SnBr$_4$ | — |
| Sr | W<br>Sr(—)$_2$ | W<br>SrH(—) | w<br>Sr$_3$(—)$_2$ | — | W<br>SrBr$_2$ | W<br>SrCO$_3$ |
| Zn | W<br>Zn(—)$_2$ | A<br>Zn(—)$_2$ | — | W<br>Zn(—)$_2$ | W<br>ZnBr$_2$ | W<br>ZnCO$_3$ |

CHART S1-continued

SOLUBILITY OF SELECTED ELEMENTS AND COMPOUNDS

| Element/Compound | Chlorate —(ClO$_3$) | Chloride | Chromate —(CrO$_4$) | Citrate —(C$_6$H$_5$O$_7$) | Cyanide | Ferricyanide —(Fe(CN)$_6$) |
|---|---|---|---|---|---|---|
| Al | W Al(—)$_3$ | W AlCl$_3$ | — | W Al(—) | — | — |
| NH$_4$ | W NH$_4$(—) | W NH$_4$Cl | W (NH$_4$)$_2$(—) | W (NH$_4$)$_3$(—) | W NH$_4$CN | W (NH$_4$)$_3$(—) |
| Sb | — | W SbCl$_3$ | — | — | — | — |
| Ba | W Ba(—)$_2$ | W BaCl$_2$ | A Ba(—) | w Ba$_3$(—)$_2$ | W Ba(CN)$_2$ | W Ba$_3$(—)$_2$ |
| Be | — | W BeCl$_2$ | — | — | — | — |
| Bi | W Bi(—)$_3$ | D BiCl$_3$ | — | A Bi(—) | W Bi(CN)$_3$ | — |
| B | — | D BCl$_3$ | — | — | — | — |
| Cd | W Cd(—)$_2$ | W CdCl$_2$ | A Cd(—) | A Cd$_3$(—)$_2$ | W Cd(CN)$_2$ | A Cd$_3$(—)$_2$ |
| Ca | W Ca(—)$_2$ | W CaCl$_2$ | W Ca(—) | w Ca$_3$(—)$_2$ | W Ca(CN)$_2$ | W Ca$_3$(—)$_2$ |
| Cr | — | I CrCl$_3$ | — | — | A Cr(CN)$_2$ | — |
| Co | W Co(—)$_2$ | W CoCl$_2$ | A Co(—) | w Co$_3$(—)$_2$ | A Co(CN)$_2$ | I Co$_3$(—)$_2$ |
| Cu | W Cu(—)$_2$ | W CuCl$_2$ | — | — | A Cu(CN)$_2$ | I Cu$_3$(—)$_2$ |
| Au' | — | w AuCl | — | — | W AuCn | — |
| Au''' | — | W AuCl$_3$ | — | — | W Au(CN)$_3$ | — |
| H | W HClO$_3$ | W HCl | — | W C$_6$H$_8$O$_7$ | W HCN | W H$_3$(—) |
| Fe'' | W Fe(—)$_2$ | W FeCl$_3$ | — | — | A Fe(CN)$_2$ | — |
| Fe''' | W Fe(—)$_3$ | W FeCl$_3$ | A Fe$_2$(—)$_3$ | W Fe(—) | — | — |
| Ga | — | D GaCl$_2$ W GaCl$_4$ | — | — | — | — |
| Ge | — | D GeCl$_2$ GeCl$_4$ | — | — | — | — |
| Ir | — | W IrCl$_2$ D IrCl$_3$ W IrCl$_4$ | — | — | — | — |
| Pb | W Pb(—)$_2$ | W PbCl$_3$ | A Pb(—) | W Pb$_3$(—)$_2$ | W Pb(CN)$_2$ | W Pb$_3$(—)$_2$ |
| Li | W Li(—) | W LiCl | W Li(—) | W Li(—) | — | — |
| Mg | W Mg(—)$_2$ | W MgCl$_2$ | W Mg(—) | W Mg$_3$(—)$_2$ | W Mg(CN)$_2$ | W Mg$_3$(—)$_2$ |
| Mn | W Mn(—)$_2$ | W MnCl$_2$ | — | W MnH(—) | — | — |
| Mo | — | D MoCl$_3$ MoCl$_4$ MoCl$_5$ | — | — | — | — |
| Hg' | W Hg(—) | A HgCl | W Hg$_3$(—) | W Hg$_3$(—) | A HgCN | — |
| Hg'' | W Hg(—)$_2$ | W HgCl$_2$ | W Hg(—) | — | A Hg(CN)$_2$ | — |
| Ni | W Ni(—)$_2$ | W NiCl$_2$ | A Ni(—) | W Ni$_3$(—)$_2$ | A Ni(CN)$_2$ | I Ni$_3$(—)$_2$ |
| K | W K(—) | W KCl | W K$_2$(—) | W K$_3$(—) | W KCN | W K$_3$(—) |
| Rh | — | I RhCl$_3$ | — | — | — | — |
| Ru | — | I RuCl$_3$ W RuCl$_4$ | — | — | — | — |
| Ag | W Ag(—) | A AgCl | W Ag$_2$(—) | W Ag$_3$(—) | A AgCN | I Ag$_3$(—) |

CHART S1-continued

SOLUBILITY OF SELECTED ELEMENTS AND COMPOUNDS

| | | | | | | |
|---|---|---|---|---|---|---|
| Na | W<br>Na(—) | W<br>NaCl | W<br>Na$_2$(—) | W<br>Na$_3$(—) | W<br>NaCN | W<br>Na$_3$(—) |
| Os | — | I<br>OsCl$_2$<br>OsCl$_3$<br>OsCl$_4$ | — | — | — | — |
| Pd | — | I<br>PdCl$_2$ | — | — | I<br>Pd(CN)$_2$ | — |
| Pt | — | w<br>PtCl$_4$ | — | — | I<br>Pt(CN)$_2$ | — |
| Sn"" | — | W<br>SnCl$_4$ | W<br>Sn(—)$_2$ | — | — | — |
| Sn" | W<br>Sn(—)$_2$ | W<br>SnCl$_2$ | A<br>Sn(—) | — | — | A<br>Sn$_3$(—)$_2$ |
| Sr | W<br>Sr(—)$_2$ | W<br>SrCl$_2$ | w<br>Sr(—) | A<br>SrH(—) | W<br>Sr(CN)$_2$ | W<br>Sr$_3$(—)$_2$ |
| Zn | W<br>Zn(—)$_2$ | W<br>ZnCl$_2$ | w<br>Zn(—) | w<br>Zn$_3$(—)$_2$ | A<br>Zn(CN)$_2$ | A<br>Zn$_3$(—)$_2$ |

| Element/<br>Compound | Ferrocyanide<br>—(Fe(CN)$_6$) | Fluoride | Formate<br>—(CHO$_2$) | Hydroxide | Iodide | Nitrate |
|---|---|---|---|---|---|---|
| Al | W<br>Al$_4$(—)$_3$ | W<br>AlF$_3$ | W<br>Al(—)$_3$ | A<br>Al(OH)$_3$ | W<br>AlI$_3$ | W<br>Al(NO$_3$)$_3$ |
| NH$_4$ | W<br>(NH$_4$)$_4$(—) | W<br>NH$_4$F | W<br>NH$_4$(—) | W<br>NH$_4$OH | W<br>NH$_4$I | W<br>NH$_4$NO$_3$ |
| Sb | — | W<br>SbF$_3$ | — | — | D<br>SbI$_3$ | — |
| Ba | W<br>Ba$_2$(—) | w<br>BaF$_2$ | W<br>Ba(—)$_2$ | W<br>Ba(OH)$_2$ | W<br>BaI$_2$ | W<br>Ba(NO$_3$)$_2$ |
| Be | — | W<br>BeF$_2$ | — | — | D<br>BeI$_2$ | W<br>Be(NO$_2$)$_2$ |
| Bi | — | W<br>BiF$_3$ | W<br>Bi(—)$_3$ | A<br>Bi(OH)$_3$ | A<br>BiI$_3$ | D<br>Bi(NO$_3$)$_3$ |
| B | — | W<br>BF$_3$ | — | — | D<br>BI$_3$ | — |
| Cd | A<br>Cd$_2$(—) | W<br>CdF$_2$ | W<br>Cd(—)$_2$ | A<br>Cd(OH)$_2$ | W<br>CdI$_2$ | W<br>Cd(NO$_3$)$_2$ |
| Ca | W<br>Ca$_2$(—) | w<br>CaF$_2$ | W<br>Ca(—)$_2$ | W<br>Ca(OH)$_2$ | W<br>CaI$_2$ | W<br>Ca(NO$_3$)$_2$ |
| Cr | — | W<br>CrF$_3$ | — | A<br>Cr(OH)$_3$ | W<br>CrI$_2$ | W<br>Cr(NO$_3$)$_3$ |
| Co | I<br>Co$_2$(—) | W<br>CoF$_2$ | W<br>Co(—)$_2$ | A<br>Co(OH)$_2$ | W<br>CoI$_2$ | W<br>Co(NO$_3$)$_2$ |
| Cu | I<br>Cu$_2$(—) | w<br>CuF$_2$ | W<br>Cu(—)$_2$ | A<br>Cu(OH)$_2$ | A<br>CuI | W<br>Cu(NO$_3$)$_2$ |
| Au' | — | — | — | A<br>AuOH | A<br>AuI | — |
| Au''' | — | — | — | W<br>Au(OH)$_3$ | A<br>AuI$_3$ | — |
| H | W<br>H4(—) | W<br>HF | W<br>CH$_2$O$_2$ | — | W<br>HI | W<br>HNO$_3$ |
| Fe" | I<br>Fe$_2$(—) | w<br>FeF$_2$ | W<br>Fe(—)$_2$ | A<br>Fe(OH)$_2$ | W<br>FeI$_2$ | W<br>Fe(NO$_3$)$_2$ |
| Fe''' | A<br>Fe$_4$(—)$_3$ | w<br>FeF$_3$ | W<br>Fe(—)$_3$ | A<br>Fe(OH)$_3$ | W<br>FeI$_3$ | W<br>Fe(NO$_3$)$_3$ |
| Ga | — | I<br>GaF$_3$ | — | I<br>Ga(OH)$_3$ | D<br>GaI$_3$ | — |
| Ge | — | W<br>GeF$_2$<br>D<br>GeF$_4$ | — | — | I<br>GeI$_2$<br>GeI$_4$ | — |
| Ir | — | D<br>IrF$_6$ | — | — | I<br>IrI$_3$<br>IrI$_4$ | — |
| Pb | A<br>Pb(—)$_2$ | w<br>PbF$_2$ | W<br>Pb(—)$_2$ | W<br>Pb(OH)$_2$ | W<br>PbI$_2$ | W<br>Pb(NO$_3$)$_2$ |
| Li | — | w<br>LiF | W<br>Li(—) | W<br>LiOH | W<br>LiI | W<br>LiNO$_3$ |
| Mg | W<br>Mg$_2$(—) | W<br>MgF$_2$ | W<br>Mg(—)$_2$ | A<br>Mg(OH)$_2$ | W<br>MgI$_2$ | W<br>Mg(NO$_3$)$_2$ |
| Mn | A<br>Mn$_2$(—) | W<br>MnF$_2$ | W<br>Mn(—)$_2$ | A<br>Mn(OH)$_2$ | W<br>MnI$_2$ | W<br>Mn(NO$_3$)$_2$ |
| Hg' | — | D<br>HgF | W<br>Hg(—) | — | A<br>HgI | W<br>HgNO3 |
| Hg" | I<br>Hg$_2$(—) | D<br>HgF$_2$ | W<br>Hg(—)$_2$ | A<br>Hg(OH)$_2$ | W<br>HgI$_2$ | W<br>Hg(NO$_3$)$_2$ |

CHART S1-continued

SOLUBILITY OF SELECTED ELEMENTS AND COMPOUNDS

| | | | | | | |
|---|---|---|---|---|---|---|
| Ni | I<br>Ni$_2$(—) | w<br>NiF$_2$ | W<br>Ni(—)$_2$ | W<br>Ni(OH)$_2$ | W<br>NiI$_2$ | W<br>Ni(NO$_3$)$_2$ |
| K | W<br>K$_4$(—) | W<br>KF | W<br>K(—) | W<br>KOH | W<br>KI | W<br>KNO$_3$ |
| Rh | — | I<br>RhF$_3$ | — | — | I<br>RhI$_3$ | W<br>Rh(NO$_3$)$_2$ |
| Ru | — | D<br>RuF$_5$ | — | — | — | — |
| Ag | I<br>Ag$_4$(—) | W<br>AgF | W<br>Ag(—) | — | I<br>AgI | W<br>AgNO$_3$ |
| Na | W<br>Na$_4$(—) | W<br>NaF | W<br>Na(—) | W<br>NaOH | W<br>NaI | W<br>NaNO$_3$ |
| Os | — | D<br>OsF$_4$<br>OsF$_6$ | — | — | W<br>OsI$_4$ | — |
| Pd | — | I<br>PdF$_2$<br>PdF$_3$ | — | — | I<br>PdI$_3$ | W<br>Pd(NO$_3$)$_2$ |
| Pt | — | — | — | A<br>Pt(OH)$_4$ | — | W<br>Pt(NO$_3$)$_4$ |
| Sn'''' | — | W<br>SnF$_4$ | — | W<br>Sn(OH)$_4$ | D<br>SnI$_4$ | — |
| Sn'' | A<br>Sn$_2$(—) | W<br>SnF$_2$ | — | A<br>Sn(OH)$_2$ | W<br>SnI$_2$ | D<br>Sn(NO$_3$)$_2$ |
| Sr | A<br>Sr$_2$(—) | w<br>SrF$_2$ | W<br>Sr(—)$_2$ | W<br>Sr(OH)$_2$ | W<br>SrI$_2$ | W<br>Sr(NO$_3$)$_2$ |
| Zn | I<br>Zn$_2$(—) | w<br>ZnF$_2$ | W<br>Zn(—)$_2$ | A<br>Zn(OH)$_2$ | W<br>ZnI$_2$ | W<br>Zn(NO$_3$)$_2$ |

| Element/<br>Compound | Oxalate<br>(C$_2$O$_4$) | Oxide | Phosphate | Silicate<br>(SiO$_3$) | Sulfate | Sulfide |
|---|---|---|---|---|---|---|
| Al | A<br>Al$_2$(—)$_3$ | A<br>Al$_2$O$_3$ | A<br>AlPO$_4$ | I<br>Al$_2$(—)$_3$ | W<br>Al$_2$(SO$_4$)$_3$ | D<br>Al$_2$S$_3$ |
| NH$_4$ | W<br>(NH$_4$)$_2$(—) | — | W<br>NH$_4$H$_2$PO$_4$ | — | W<br>(NH$_4$)$_2$SO$_4$ | W<br>(NH$_4$)$_2$S |
| Sb | — | W<br>SbO$_3$ | — | — | A<br>Sb$_2$(SO$_4$)$_3$ | A<br>Sb$_2$S$_3$ |
| Ba | W<br>Ba(—) | W<br>BaO | A<br>Ba$_3$(PO$_4$)$_2$ | W<br>Ba(—) | A<br>BaSO$_4$ | D<br>BaS |
| Be | W<br>Be(—) | I<br>BeSO$_4$ | W<br>Be$_3$(—)$_4$ | — | I<br>Be(—) | D<br>BeS |
| Bi | A<br>Bi$_2$(—)$_3$ | A<br>Bi$_2$O$_3$ | A<br>BiPO$_4$ | — | D<br>Bi$_2$(SO$_4$)$_3$ | A<br>Bi$_2$S$_3$ |
| B | — | W<br>B$_2$O$_3$ | — | — | — | D<br>B$_2$S$_3$<br>B$_2$S$_5$ |
| Cd | W<br>Cd(—) | A<br>CdO | A<br>Cd$_3$(PO$_4$)$_2$ | A<br>Cd(—) | W<br>CdSO$_4$ | A<br>CdS |
| Ca | A<br>Ca(—) | w<br>CaO | w<br>Ca$_3$(PO$_4$) | W<br>Ca(—) | W<br>CaSO$_4$ | W<br>CaS |
| Cr | W<br>Cr(—) | A<br>Cr$_2$O$_3$ | w<br>Cr$_3$(PO$_4$)$_2$ | — | W<br>Cr$_2$(SO$_4$)$_3$ | D<br>Cr$_2$S$_3$ |
| Co | A<br>Co(—) | A<br>CoO | A<br>Co$_3$(PO$_4$)$_2$ | A<br>CoSiO$_4$ | W<br>CoSO$_4$ | A<br>CoS |
| Cu | A<br>Cu(—) | A<br>CuO | A<br>Cu$_3$(PO$_4$)$_2$ | A<br>Cu(—) | W<br>CuSO$_4$ | A<br>CuS |
| Au' | — | A<br>Au$_2$O | — | — | — | I<br>Au$_2$S |
| Au''' | — | A<br>Au$_2$O$_3$ | — | — | — | I<br>Au$_2$S$_3$ |
| H | W<br>C$_2$H$_2$O$_4$ | W<br>H$_2$O$_2$ | W<br>H$_3$PO$_4$ | I<br>H$_2$SiO$_3$ | W<br>H$_2$SO$_4$ | W<br>H$_2$S |
| Fe'' | A<br>Fe(—) | A<br>FeO | A<br>Fe$_3$(PO$_4$)$_2$ | — | W<br>FeSO$_4$ | A<br>FeS |
| Fe''' | W<br>Fe$_3$(—)$_2$ | A<br>Fe$_2$O$_3$ | w<br>FePO$_4$ | — | W<br>Fe$_2$(SO$_4$)$_3$ | D<br>Fe$_2$S$_3$ |
| Ga | — | I<br>Ga$_2$O<br>Ga$_2$O$_3$ | — | — | W<br>Ga$_2$(SO$_4$)$_3$ | I<br>GaS<br>D<br>Ga$_2$S |
| Ge | — | I<br>GeO<br>GeO$_2$ | — | — | — | — |
| Ir | W<br>H$_3$[Ir(C$_2$O$_4$)$_3$] | I<br>Ir$_2$O$_3$<br>Ir$_2$O$_2$ | — | — | — | — |
| Pb | A<br>Pb(—) | w<br>PbO | A<br>Pb$_3$(PO$_4$)$_2$ | A<br>Pb(—) | W<br>PbSO$_4$ | A<br>PbS |

CHART S1-continued

SOLUBILITY OF SELECTED ELEMENTS AND COMPOUNDS

| | | | | | | |
|---|---|---|---|---|---|---|
| Li | w<br>Li(—) | W<br>$Li_2O$ | W<br>$LiH_2PO_4$ | I<br>Li(—) | W<br>$LiSO_4$ | W<br>$Li_2S$ |
| Mg | W<br>Mg(—) | A<br>MgO | w<br>$Mg_3(PO_4)_2$ | A<br>Mg(—) | W<br>$MgSO_4$ | A<br>MgS |
| Mn | W<br>Mn(—) | A<br>MnO | w<br>$Mn_3(PO_4)_2$ | I<br>Mn(—) | W<br>$MnSO_4$ | A<br>MnS |
| Hg' | A<br>$Hg_2$(—) | A<br>$Hg_2O$ | A<br>$Hg_2PO_4$ | — | W<br>$Hg_2SO_4$ | I<br>$Hg_2S$ |
| Hg" | A<br>Hg(—) | w<br>HgO | A<br>$Hg_3(PO_4)_2$ | — | D<br>$HgSO_4$ | I<br>HgS |
| Ni | A<br>Ni(—) | A<br>Ni(—) | A<br>$Ni_3(PO_4)_2$ | — | W<br>$NiSO_4$ | A<br>NiS |
| K | W<br>$K_2$(—) | W<br>$K_2O$ | W<br>$K_3PO_4$ | W<br>$K_2$(—) | W<br>$K_2SO_4$ | W<br>$K_2S$ |
| Ag | A<br>$Ag_2$(—) | W<br>$Ag_2O$ | A<br>$Ag_3PO_4$ | — | W<br>$Ag_2SO_4$ | A<br>$Ag_2S$ |
| Na | W<br>$Na_2$(—) | D<br>$Na_2O$ | W<br>$Na_3PO_4$ | W<br>$Na_2$(—) | W<br>$Na_2SO_4$ | W<br>$Na_2S$ |
| Os | — | I<br>$Os_2O_2$<br>$Os_2O$<br>$Os_2O_3$<br>$Os_2O_4$ | — | — | — | I<br>$OsS_2$ |
| Pd | — | I<br>PdO<br>$PdO_2$ | — | — | W<br>$PdSO_4$ | I<br>PdS<br>$PdS_2$<br>$Pd_2S$ |
| Pt | — | A<br>PtO | — | — | W<br>$Pt(SO_4)_2$ | I<br>PtS |
| Sn"" | — | A<br>$SnO_2$ | — | — | W<br>$Sn(SO_4)_2$ | A<br>$SnS_2$ |
| Sn" | A<br>Sn(—) | A<br>SnO | A<br>Sn3(PO4)2 | — | W<br>$SnSO_4$ | A<br>SnS |
| Sr | W<br>Sr(—) | w<br>Sr(—) | Zn3(PO4)2 | A<br>Sr(—) | W<br>$SrSO_4$ | W<br>SrS |
| Zn | A<br>Zn(—) | w<br>ZnO | Zn3(PO4)2 | A<br>Zn(—) | W<br>$ZnSO_4$ | A<br>ZnS |

| Element/Compound | Tartrate —$(C_4H_4O_6)$ | Thiocyanate |
|---|---|---|
| Al | W<br>$Al_2$(—)$_3$ | — |
| $NH_4$ | W<br>$(NH_4)_2$(—)$_3$ | W<br>$NH_4CNS$ |
| Sb | W<br>$Sb_2$(—)$_3$ | — |
| Ba | W<br>Ba(—) | W<br>$Ba(CNS)_2$ |
| Be | — | — |
| Bi | A<br>$Bi_2$(—)$_3$ | — |
| B | — | — |
| Cd | A<br>Cd(—) | — |
| Ca | W<br>Ca(—) | W<br>$Ca(CNS)_2$ |
| Cr | — | — |
| Co | W<br>Co(—) | W<br>$Co(CNS)_2$ |
| Cu | W<br>Cu(—) | D<br>CuCNS |
| Au' | — | — |
| Au''' | — | — |
| H | W<br>$C_4H_6O_6$ | W<br>CNSH |
| Fe" | W<br>Fe(—) | W<br>$Fe(CNS)_2$ |
| Fe''' | W<br>$Fe_2$(—)$_3$ | W<br>$Fe(CNS)_2$ |
| Ga | — | — |
| Ge | — | — |
| Ir | — | — |
| Li | W<br>Li(—) | W<br>LiSCN |
| Pb | A<br>Pb(—) | W<br>$Pb(CNS)_2$ |

CHART S1-continued

SOLUBILITY OF SELECTED ELEMENTS AND COMPOUNDS

| | | |
|---|---|---|
| Mg | w | W |
| | Mg(—) | Mg(CNS)$_2$ |
| Mn | w | W |
| | Mn(—) | Mn(CNS)$_2$ |
| Hg' | I | A |
| | Hg2(—) | HgCNS |
| Hg" | — | Hg(CNS)$_2$ |
| Ni | A | — |
| | Ni(—) | |
| K | W | W |
| | K$_2$(—) | KCNS |
| Ag | w | I |
| | Ag$_2$(—) | AgCNS |
| Na | W | W |
| | Na$_2$(—) | NaCNS |
| Os | — | — |
| Pd | — | — |
| Pt | — | — |
| Sn"" | — | — |
| Sn" | W | — |
| | Sn(—) | |
| Sr | w | W |
| | Sr(—) | Sr(CNS)$_2$ |
| Zn | w | W |
| | Zn(—) | Zn(CNS)$_2$ |

Although the present embodiments to the invention have been described with reference to preferred embodiments, workers skilled in the art will recognize that changes may be made in form and detail without departing from the spirit and scope of the embodiments to the invention.

Since other modifications and changes varied to fit particular operating requirements and environments will be apparent to those skilled in the art, the embodiments to the invention is not considered limited to the examples chosen for purposes of disclosure, and covers all changes and modifications which do not constitute departures from spirit and scope of these embodiments or modifications to the invention.

What is claimed is:

1. A method for purifying a methane containing stream, the method comprising:
   introducing a raw methane stream into a mixing zone through an inlet, the raw methane stream including methane and one or more contaminants selected from the group consisting of carbon dioxide, ammonia, hydrogen sulfide and combinations thereof;
   introducing a water stream into the mixing zone through a separate water inlet such that the water stream is commingled with the raw methane stream upon both streams entering the mixing zone;
   passing the commingled streams through a venturi so as to homogenize the streams such that one or more contaminants within the raw methane stream are dispersed within the water stream, forming a contaminant isolation stream including the one or more contaminants and a purified methane stream;
   wherein the water stream is chilled to below ambient temperature to increase dissolution of the one or more contaminants therein.

2. A method as recited in claim 1, wherein the raw methane stream includes carbon dioxide, the carbon dioxide dissolving into the chilled water stream, so as to remove the carbon dioxide from the raw methane stream, the method further comprising capturing the carbon dioxide and conveying it one or more storage tanks for use as a plant metabolite.

3. A method as recited in claim 1, wherein the raw methane stream includes hydrogen sulfide, the hydrogen sulfide dissolving into the chilled water stream, so as to remove the hydrogen sulfide from the raw methane stream, the dissolved hydrogen sulfide forming hydrogen gas and precipitated elemental sulfur, the method further comprising collecting the precipitated sulfur for use as a value added product.

4. A method as recited in claim 1, wherein an ante-chamber is provided, the raw methane stream being introduced into the antechamber before introduction into the mixing zone, the ante-chamber comprising a packing material therein for retarding flow of the raw methane stream through the ante-chamber.

5. A method as recited in claim 1, wherein a retention chamber is provided downstream from an outlet of the venturi so as to extend a residence time of the contaminant isolation stream and the purified methane stream.

6. A method as recited in claim 5, wherein the inlets, the venturi, and the retention chamber are insulated.

7. A method for purifying a biogas stream containing methane using a PPH, the method comprising:
   introducing a raw biogas stream into a mixing zone through an inlet of the PPH, the raw biogas stream including methane, carbon dioxide, and hydrogen sulfide;
   introducing a chilled water stream into the mixing zone through a separate water inlet such that the water stream is commingled with the raw biogas stream upon both streams entering the mixing zone;
   passing the commingled streams through a venturi of the PPH so as to homogenize the streams such that the carbon dioxide and hydrogen sulfide are dissolved into the chilled water stream and removed from the raw biogas stream, forming a purified methane stream and an aqueous contaminant isolation stream;
   wherein the water stream is chilled to below ambient temperature to increase dissolution of the carbon dioxide and hydrogen sulfide therein.

8. A method as recited in claim 7, wherein the chilled water is oxygenated, and the raw biogas stream further comprises ammonia, wherein the hydrogen sulfide is converted to water and elemental sulfur in the presence of the chilled oxygenated water, and the carbon dioxide and ammonia are converted to ammonium carbonate in the presence of the chilled oxygenated water.

9. A method as recited in claim 8, further comprising introducing oxygen into a chilled water stream to produce the chilled oxygenated water stream prior to its introduction into the mixing zone, the introduction of the oxygen into the chilled water stream being accomplished within an upstream PPH.

10. A method as recited in claim 9, wherein oxygen is dissolved within the chilled oxygenated water stream at a concentration from about 8 ppm to about 12 ppm.

11. A method as recited in claim 9, wherein oxygen is dissolved within the chilled oxygenated water stream at a concentration above that that would be provided by sparging.

12. A method as recited in claim 8, wherein the hydrogen sulfide that is converted to hydrogen and elemental sulfur in the oxygenated water results from the hydrogen sulfide dissolving in the water to form dissolved hydrogen and the elemental sulfur, the dissolved hydrogen reacting with oxygen in the chilled oxygenated water to produce the water and elemental sulfur that the hydrogen sulfide is converted to.

13. A method as recited in claim 8, wherein the carbon dioxide is converted to carbonic acid in the chilled oxygenated water, the ammonia reacting with the carbonic acid in the chilled oxygenated water to produce the ammonium carbonate that the carbon dioxide and ammonia are converted to.

14. A method as recited in claim 7, wherein the raw biogas stream further includes water vapor, the water vapor condensing to form liquid water that is removed from the raw biogas stream, and which enters the aqueous contaminant isolation stream.

15. A method as recited in claim 7, wherein the raw biogas stream further includes volatile organic compounds (VOCs) including free fatty acids (FFAs), the method further comprising contacting the FFAs with an oleophilic mesh or a chilled metal surface to remove them from the raw biogas stream.

16. A method as recited in claim 7, wherein the raw biogas stream further includes particulate matter (PM), wherein the PM settles with elemental sulfur in the aqueous contaminant isolation stream.

17. A method as recited in claim 7, wherein the chilled water stream is chilled to a temperature within a range of 60° F. to 75° F.

18. A method as recited in claim 7, wherein the purified methane stream is conveyed to an internal combustion engine or burner for use as fuel.

* * * * *